United States Patent
Turturro et al.

(10) Patent No.: US 7,297,121 B2
(45) Date of Patent: *Nov. 20, 2007

(54) BIOPSY INSTRUMENT HAVING IRRIGATION AND ASPIRATION CAPABILITIES

(75) Inventors: Vincent Turturro, Miramar, FL (US); Jose L. Francese, Miami Springs, FL (US); Saul Gottlieb, Miramar, FL (US); Juergen Kortenbach, Miami Springs, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 256 days.

This patent is subject to a terminal disclaimer.

(21) Appl. No.: 11/150,328

(22) Filed: Jun. 13, 2005

(65) Prior Publication Data
US 2005/0245841 A1 Nov. 3, 2005

Related U.S. Application Data

(60) Continuation of application No. 09/977,289, filed on Oct. 16, 2001, now Pat. No. 6,926,676, which is a division of application No. 09/079,168, filed on May 15, 1998, now Pat. No. 6,331,165, which is a continuation-in-part of application No. 08/756,260, filed on Nov. 25, 1996, now Pat. No. 5,897,507.

(51) Int. Cl.
*A61B 10/00* (2006.01)
(52) U.S. Cl. .................................................. 600/563
(58) Field of Classification Search ........ 600/562–568; 606/205–207, 127, 170
See application file for complete search history.

(56) References Cited

U.S. PATENT DOCUMENTS 2,708,437 A   5/1955  Hutchins (Continued)

FOREIGN PATENT DOCUMENTS

EP   0 317 526 A1   5/1989

(Continued)

OTHER PUBLICATIONS

Notice of Reasons for Rejection mailed Sep. 12, 2006 in Japanese Patent Application No. 10-526709.

(Continued)

*Primary Examiner*—Max F. Hindenburg
*Assistant Examiner*—Brian Szmal
(74) *Attorney, Agent, or Firm*—Finnegan, Henderson, Farabow, Garrett and Dunner, LLP

(57) ABSTRACT

The invention may include a biopsy instrument having a proximal end and a distal end. The biopsy instrument may include a distal assembly for performing a surgical operation, an elongate flexible member connected to and extending in a proximal direction from the distal assembly, the flexible member including a conduit thereth rough, a proximal actuation handle coupled to a proximal end of the flexible member, the proximal actuation handle including an access opening in fluid connection with the conduit, and a sample collector including a catcher handle and a catcher body. The catcher body may be configured for insertion into the access opening and is removably attached to the catcher handle.

22 Claims, 37 Drawing Sheets

U.S. PATENT DOCUMENTS

| | | |
|---|---|---|
| 3,173,414 A | 3/1965 | Guillant |
| 3,289,669 A | 12/1966 | Dwyer et al. |
| 3,401,684 A | 9/1968 | Dremann |
| 3,590,808 A | 7/1971 | Muller |
| 3,732,858 A | 5/1973 | Banko |
| 3,964,468 A | 6/1976 | Schulz |
| 3,980,086 A | 9/1976 | Kletschka et al. |
| 3,989,033 A | 11/1976 | Halpern et al. |
| 3,989,049 A | 11/1976 | Yoon |
| 3,992,565 A | 11/1976 | Gatfield |
| 4,014,333 A | 3/1977 | McIntyre |
| 4,200,111 A | 4/1980 | Harris |
| 4,282,884 A | 8/1981 | Boebel |
| 4,445,517 A | 5/1984 | Feild |
| 4,519,385 A | 5/1985 | Atkinson et al. |
| 4,522,206 A | 6/1985 | Whipple et al. |
| 4,617,013 A | 10/1986 | Betz |
| 4,632,110 A | 12/1986 | Sanagi |
| 4,644,951 A | 2/1987 | Bays |
| 4,646,751 A | 3/1987 | Maslanka |
| 4,651,753 A | 3/1987 | Lifton |
| 4,662,371 A | 5/1987 | Whipple et al. |
| 4,681,123 A | 7/1987 | Valtchev |
| 4,693,257 A | 9/1987 | Markham |
| 4,712,545 A | 12/1987 | Honkanen |
| 4,759,349 A | 7/1988 | Betz et al. |
| 4,763,668 A | 8/1988 | Macek et al. |
| 4,776,840 A | 10/1988 | Freitas et al. |
| 4,785,825 A | 11/1988 | Romaniuk et al. |
| 4,881,550 A | 11/1989 | Kothe |
| 4,909,782 A | 3/1990 | Semm et al. |
| 4,915,688 A | 4/1990 | Bischof, deceased et al. |
| 4,919,152 A | 4/1990 | Ger |
| 4,924,851 A | 5/1990 | Ognier et al. |
| RE33,258 E | 7/1990 | Onik et al. |
| 4,944,093 A | 7/1990 | Falk |
| 4,950,278 A | 8/1990 | Sachse et al. |
| 4,953,559 A | 9/1990 | Salerno |
| 4,966,162 A | 10/1990 | Wang |
| 4,971,067 A | 11/1990 | Bolduc et al. |
| 4,973,311 A | 11/1990 | Iwakoshi et al. |
| 4,976,723 A | 12/1990 | Schad |
| 4,986,825 A | 1/1991 | Bays et al. |
| 5,035,688 A | 7/1991 | Inui |
| 5,082,000 A | 1/1992 | Picha et al. |
| 5,085,658 A | 2/1992 | Meyer |
| 5,106,364 A | 4/1992 | Hayafuji et al. |
| 5,112,346 A | 5/1992 | Hiltebrandt et al. |
| 5,125,910 A | 6/1992 | Freitas |
| 5,147,292 A | 9/1992 | Kullas et al. |
| 5,152,780 A | 10/1992 | Honkanen et al. |
| 5,160,319 A | 11/1992 | Emery et al. |
| 5,160,343 A | 11/1992 | Brancel et al. |
| 5,171,255 A | 12/1992 | Rydell |
| 5,172,700 A | 12/1992 | Bencini et al. |
| 5,176,629 A | 1/1993 | Kullas et al. |
| 5,186,714 A | 2/1993 | Boudreault |
| 5,195,533 A | 3/1993 | Chin et al. |
| 5,195,958 A | 3/1993 | Phillips |
| 5,195,959 A | 3/1993 | Smith |
| 5,197,963 A | 3/1993 | Parins |
| 5,197,968 A | 3/1993 | Clement |
| 5,209,747 A | 5/1993 | Knoepfler |
| 5,217,460 A | 6/1993 | Knoepfler |
| 5,219,357 A | 6/1993 | Honkanen et al. |
| 5,230,704 A | 7/1993 | Moberg et al. |
| 5,244,459 A | 9/1993 | Hill |
| 5,251,641 A | 10/1993 | Xavier |
| 5,285,795 A | 2/1994 | Ryan et al. |
| 5,286,255 A | 2/1994 | Weber |
| 5,300,087 A | 4/1994 | Knoepfler |
| 5,312,327 A | 5/1994 | Bales et al. |
| 5,312,400 A | 5/1994 | Bales et al. |
| 5,314,406 A | 5/1994 | Arias et al. |
| 5,325,866 A | 7/1994 | Krzyzanowski |
| 5,336,238 A | 8/1994 | Holmes et al. |
| 5,344,428 A | 9/1994 | Griffiths |
| 5,417,709 A | 5/1995 | Slater |
| 5,419,774 A | 5/1995 | Willard et al. |
| 5,431,645 A | 7/1995 | Smith et al. |
| 5,456,689 A | 10/1995 | Kresch et al. |
| 5,471,992 A | 12/1995 | Banik et al. |
| 5,505,210 A | 4/1996 | Clement |
| 5,526,822 A | 6/1996 | Burbank et al. |
| 5,527,331 A | 6/1996 | Kresch et al. |
| 5,527,332 A | 6/1996 | Clement |
| 5,538,008 A | 7/1996 | Crowe |
| 5,542,432 A | 8/1996 | Slater et al. |
| 5,551,448 A | 9/1996 | Matula et al. |
| 5,562,102 A | 10/1996 | Taylor |
| 5,562,640 A | 10/1996 | McCabe et al. |
| 5,562,702 A | 10/1996 | Huitema et al. |
| 5,569,299 A | 10/1996 | Dill et al. |
| 5,573,008 A | 11/1996 | Robinson et al. |
| 5,575,293 A | 11/1996 | Miller et al. |
| 5,593,416 A | 1/1997 | Donahue |
| 5,595,185 A | 1/1997 | Erlich |
| 5,599,345 A | 2/1997 | Edwards et al. |
| 5,601,572 A | 2/1997 | Middleman et al. |
| 5,601,585 A | 2/1997 | Banik et al. |
| 5,601,601 A | 2/1997 | Tal et al. |
| 5,603,724 A | 2/1997 | O'Connor |
| 5,607,391 A | 3/1997 | Klinger et al. |
| 5,620,415 A | 4/1997 | Lucey et al. |
| 5,636,639 A | 6/1997 | Turturro et al. |
| 5,638,827 A | 6/1997 | Palmer et al. |
| 5,645,075 A | 7/1997 | Palmer et al. |
| 5,649,547 A | 7/1997 | Ritchart et al. |
| 5,683,359 A | 11/1997 | Farkas et al. |
| 5,683,388 A | 11/1997 | Slater et al. |
| 5,715,832 A | 2/1998 | Koblish et al. |
| 5,730,717 A | 3/1998 | Gelbfish |
| 5,766,134 A | 6/1998 | Lisak et al. |
| 5,775,333 A | 7/1998 | Burbank et al. |
| 5,779,648 A | 7/1998 | Banik et al. |
| 5,810,876 A | 9/1998 | Kelleher |
| 5,823,971 A | 10/1998 | Banik et al. |
| 5,840,044 A | 11/1998 | Dassa et al. |
| 5,871,453 A | 2/1999 | Banik et al. |
| 5,897,507 A | 4/1999 | Kortenbach et al. |
| 5,928,164 A | 7/1999 | Burbank et al. |
| 5,961,534 A | 10/1999 | Banik et al. |
| 5,980,469 A | 11/1999 | Burbank et al. |
| 6,017,316 A | 1/2000 | Ritchart et al. |
| 6,032,673 A | 3/2000 | Savage et al. |
| 6,050,955 A | 4/2000 | Bryan et al. |
| 6,053,877 A | 4/2000 | Banik et al. |
| 6,083,150 A | 7/2000 | Aznoian et al. |
| 6,142,957 A | 11/2000 | Diamond et al. |
| 6,331,165 B1 | 12/2001 | Turturro et al. |
| 6,428,486 B2 | 8/2002 | Ritchart et al. |
| 6,926,676 B2 * | 8/2005 | Turturro et al. ............. 600/562 |
| 2001/0007925 A1 | 7/2001 | Ritchart et al. |
| 2002/0016555 A1 | 2/2002 | Ritchart et al. |
| 2002/0120212 A1 | 8/2002 | Ritchart et al. |
| 2004/0019299 A1 | 1/2004 | Ritchart et al. |
| 2006/0167377 A1 | 7/2006 | Ritchart et al. |

FOREIGN PATENT DOCUMENTS

| | | |
|---|---|---|
| EP | 0 526 115 A1 | 2/1993 |
| EP | 0 890 339 A1 | 1/1999 |
| JP | S59-186548 A | 10/1984 |
| JP | S62-164010 U | 10/1987 |

| | | |
|---|---|---|
| JP | H01-157714 U | 10/1989 |
| JP | 4135554 AA | 5/1992 |
| JP | H06-503502 A | 4/1994 |
| JP | H09-503404 A | 4/1997 |
| JP | H09-503942 A | 4/1997 |
| JP | H09-510638 A | 10/1997 |
| WO | WO 92/07516 A1 | 5/1992 |
| WO | WO 93/07917 A1 | 4/1993 |
| WO | WO 95/08945 A2 | 4/1995 |
| WO | WO 95/10981 A1 | 4/1995 |
| WO | WO 95/25465 A2 | 9/1995 |
| WO | WO 96/22056 A1 | 7/1996 |

OTHER PUBLICATIONS 510K application communications between Department of Health & Human Services and William Z. Kolozsi, M.D., relating to Triton Technologies Multiple Biopsy Device, dated Mar. 11, 1991 through May 1, 1991, 27 pages.

Quinton, "Model 4.7mm Multipurpose Biopsy Tube" operator manual, 10 pages.

* cited by examiner

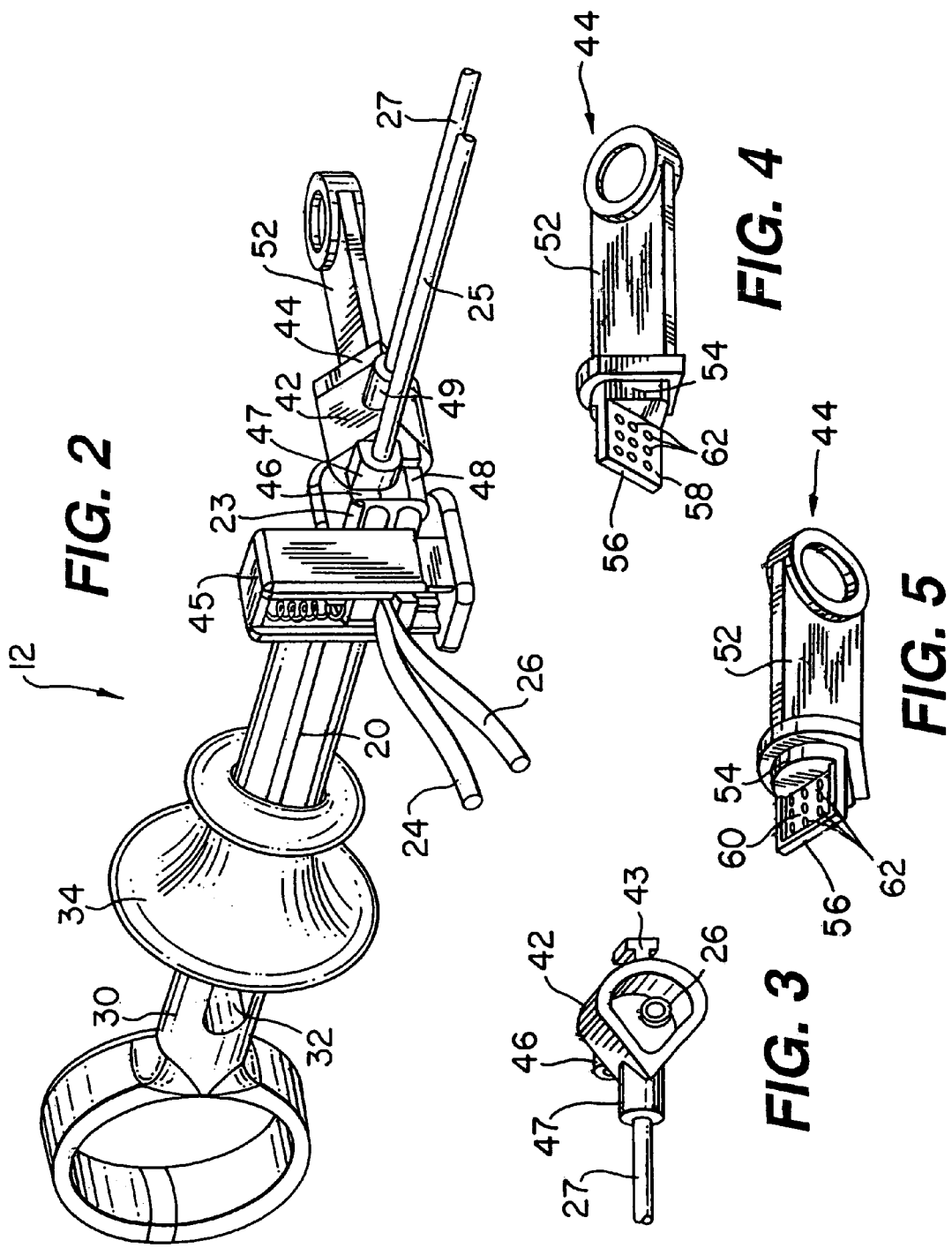

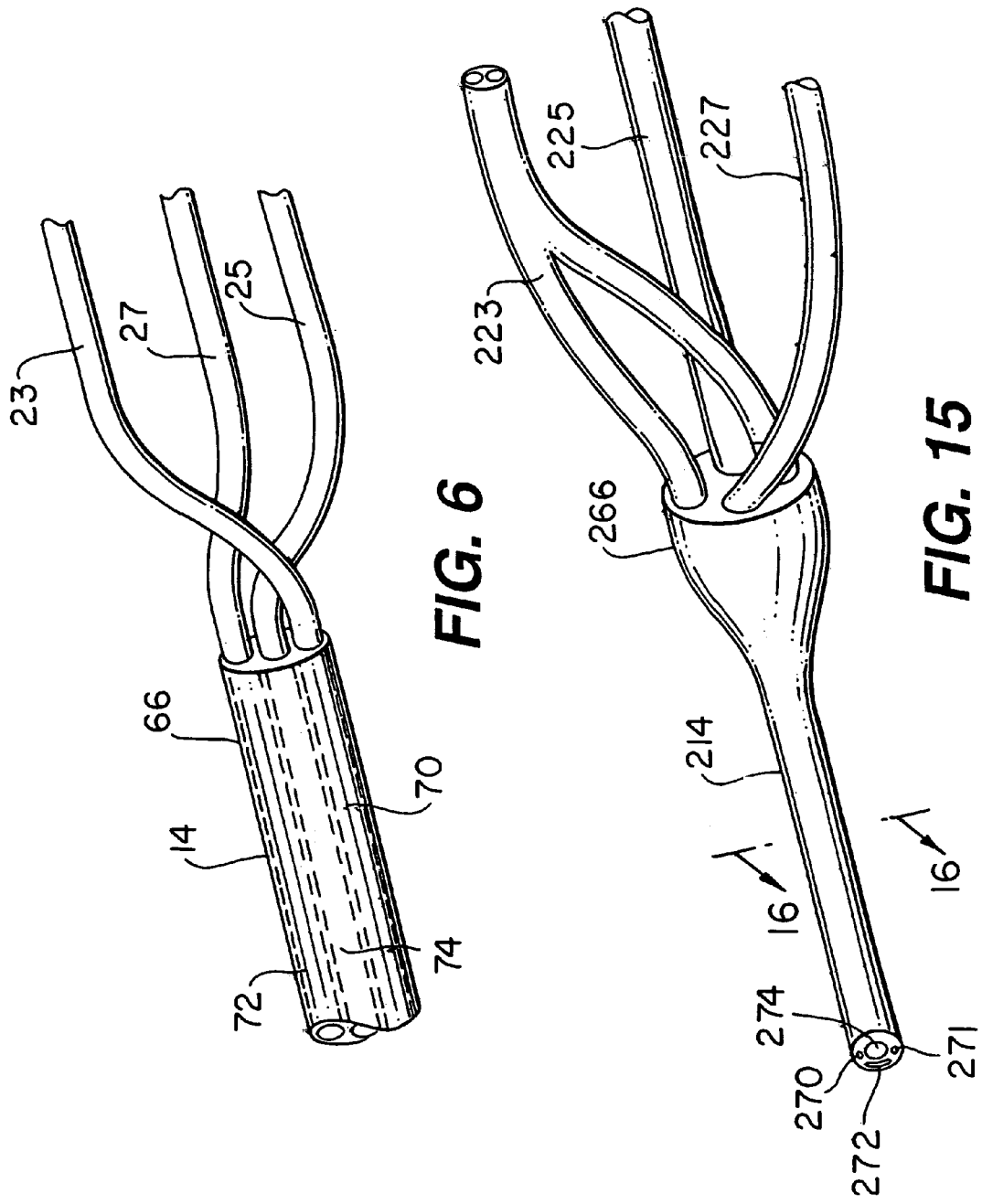

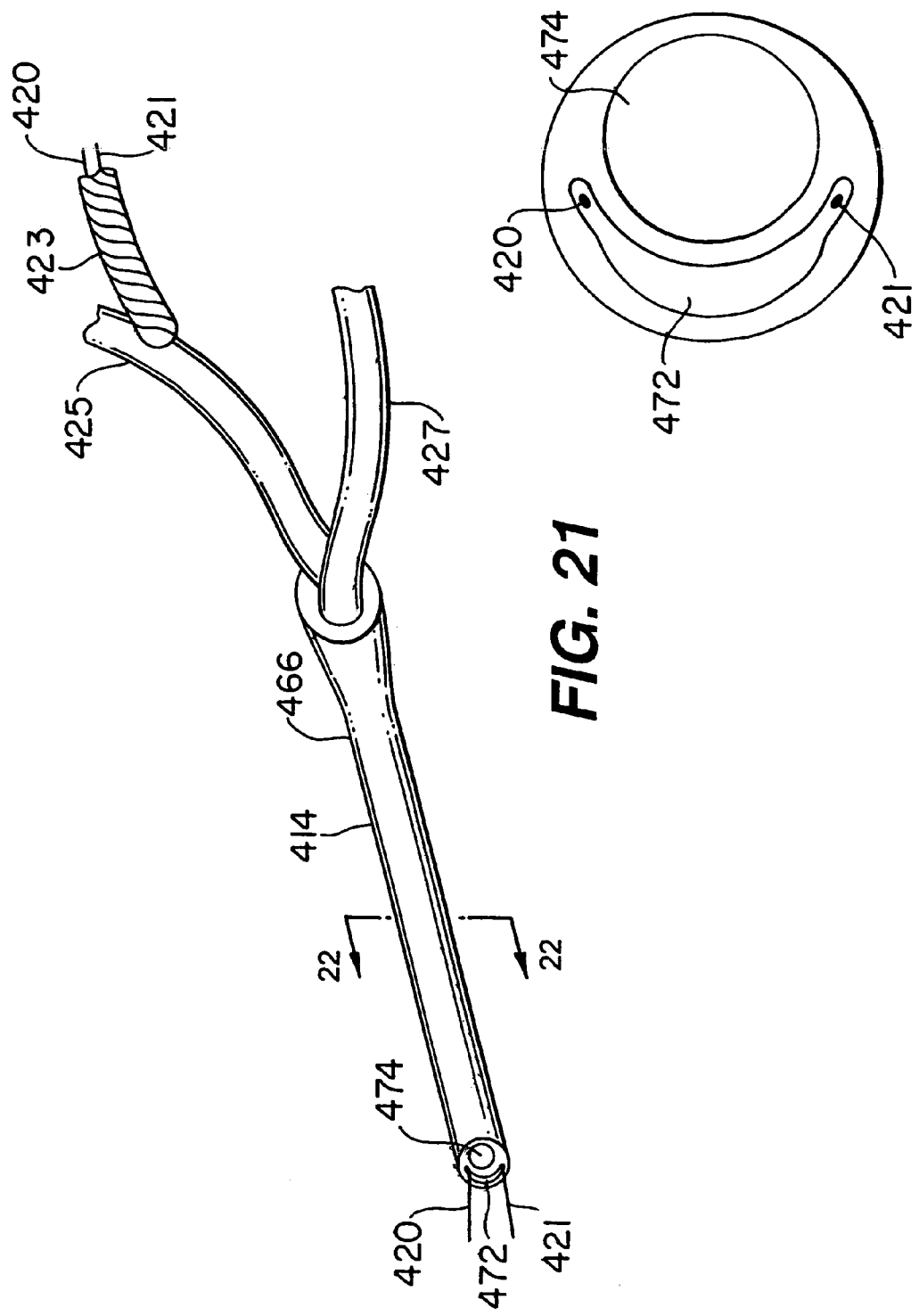

BIOPSY INSTRUMENT HAVING IRRIGATION AND ASPIRATION CAPABILITIES

This application is a continuation of U.S. patent application Ser. No. 09/977,289 filed Oct. 16, 2001, now U.S. Pat. No. 6,926,676, which is a divisional of U.S. patent application Ser. No. 09/079,168 filed May 15, 1998, now U.S. Pat. No. 6,331,165, which is a continuation-in-part of U.S. patent application Ser. No. 08/756,260 filed Nov. 25, 1996, now U.S. Pat. No. 5,897,507, the entirety of all of which are incorporated herein by reference.

BACKGROUND OF THE INVENTION

1. Field of the Invention

This invention relates broadly to endoscopic surgical instruments. More particularly, this invention relates to an endoscopic biopsy instrument with means for facilitating sample removal without withdrawal of the biopsy instrument from an endoscope.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and U.S. Pat. No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that dry suctioning tissue samples (i.e., without the use of an irrigating fluid) through a long narrow flexible bioptome is virtually impossible.

Efforts have been made to provide multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade for moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

The device of the Lifton patent suffers from several recognizable drawbacks. First, it is often difficult to obtain a tissue sample laterally of the device. Second, in order to expedite the obtaining of a lateral sample, a syringe is used to help draw the tissue into the lateral opening. However, this causes what was once a two-step procedure (position and cut), to become a three-step procedure (position, suction, cut). In addition, the use of a syringe requires an additional hand. Third, the Lifton patent adds a fourth step to the biopsy procedure by requiring that the tissue sample be pushed into the storage space. Thus, in all, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. No. 5,171,255 to Rydell. Rydell provides a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. While the device of Rydell is effective in providing a multiple sample tool where each sample is obtained with a traditional two-step procedure (position and cut), it is still limited to lateral cutting which is often problematic. Traditional biopsy forceps provide jaws which can grasp tissue frontally or laterally. Even as such, it is difficult to position the jaws about the tissue to be sampled. Lateral sampling is even more difficult.

A multiple sample biopsy forceps of a more traditional form is disclosed-in co-owned U.S. Pat. No. 5,542,432 to Slater et al. Slater et al. discloses an endoscopic multiple sample biopsy forceps having a jaw assembly which includes a pair of opposed toothed jaw cups each of which is coupled by a resilient arm to a base member. The base member of the jaw assembly is mounted inside a cylinder and axial movement of one of the jaw assembly and cylinder relative to the other draws the arms of the jaws into the cylinder or moves the cylinder over the arms of the jaws to bring the jaw cups together in a biting action. The arms of the jaws effectively form a storage chamber which extends proximally from the lower jaw cup and prevents accumulated biopsy samples from being squeezed laterally out from between the jaws during repeated opening and closing of the jaws and the lower jaw cup enhances movement of the biopsy samples into the storage chamber. The device can hold up to four samples before it must be retrieved out of the endoscope. However, in some biopsy procedures it is sometimes desirous to retrieve more. In addition, it has been found that samples within the chamber can stick together and make determinations of which sample came from which biopsy site somewhat difficult.

U.S. Pat. No. 5,538,008 to Crowe discloses a multiple sample bioptome which purports to take several samples and to transfer each sample by water pressure through a duct to the proximal end of the instrument, where each sample can be individually retrieved. The device includes a plastic jaw set biased in an open position and coupled to the distal end of an elongate tube, up to seven feet long. The tube defines a duct. A sleeve extends over the tube and a water flow passage is provided between the tube and the sleeve. An aperture is provided in the tube to permit the water flow passage to meet the duct at the distal end of the tube. Withdrawing the tube into the sleeve is disclosed to force the jaws closed and enable a sample to be cut from tissue and lodge in the duct. The water flow passage is disclosed to enable water to flow under pressure from the proximal end of passage to the distal end of the passage, through the aperture and into the distal end of the duct and to be aspirated to the proximal end of the duct, thereby transferring with it any sample contained in the duct to the proximal end where the sample can be retrieved.

While on paper the Crowe device is appealing, in practice the design is impractical and flawed. For example, it would be very difficult, if not impossible, to slide the elongate tube, up to seven feet in length, relative to a sleeve of substantially the same length. It would also be difficult to maintain an unobstructed water flow passage between the tube and sleeve as the tube and sleeve curve and bend through the body. Furthermore, in order for the jaws to cut a tissue sample, the tube and jaws must be drawn into the sleeve, thereby undesirably pulling the jaws away from the tissue to be sampled.

SUMMARY OF THE INVENTION

An endoscopic biopsy instrument is provided and generally includes a proximal actuation handle, a distal forceps assembly, a control member coupled to the proximal actuation handle and the distal forceps assembly, and a flexible multi-lumen tubular member having an aspiration conduit, and a control conduit which receives the control member.

According to a first aspect of the invention, the proximal actuation handle includes a shaft and a spool slidably mounted on the shaft. The actuation handle is also provided with a proximal irrigation passage, a sample chamber, a sample catch member, and a pinch valve which regulates irrigation and aspiration. The proximal irrigation passage is coupled to the irrigation conduit and to an irrigation coupling tube. The sample chamber is coupled to the aspiration conduit and to an aspiration coupling tube. The sample catch member includes a screen which is inserted into the sample chamber and filters out tissue samples from the aspirated fluid. The irrigation coupling tube and the aspiration coupling tube extend through the pinch valve which operates to control the flow of fluid through the tubes. The actuation handle is coupled to the proximal ends of both the flexible tubular member and the control member and moves the control member relative to the tubular member.

The distal assembly is coupled to the distal end of the tubular member and includes a hollow stationary jaw coupled over the distal end of the aspiration conduit and a hollow movable jaw pivotably coupled adjacent the irrigation conduit. The stationary jaw, preferably formed from a hard plastic or stainless steel, has a blunt edge, while the movable jaw is preferably a metal jaw with a sharp cutting edge. The movable jaw is further coupled to the control member, such that actuation of the actuation handle moves the movable jaw relative to the stationary jaw, and thereby moves the jaw from an open position to a closed position. Moving the hollow jaw to a closed position provides a substantially fluidtight coupling between the irrigation and aspiration conduits.

It will be appreciated that the distal end of the instrument is brought into contact with tissue of which a sample is required and the actuation handle is actuated to close the jaws and cut off a tissue sample. With the jaws in a closed position, water is irrigated through the irrigation conduit to the jaws at the distal end of the instrument and aspirated from the jaws to the proximal end of the instrument through the aspiration conduit, such that the sample cut by the jaws is aspirated with the water. As the water is aspirated it passes through the chamber and the sample is filtered onto the screen. The screen may easily be removed to retrieve the sample. It will be further appreciated that the entire procedure of cutting a sample and retrieving the sample may be performed without removing the endoscopic biopsy instrument from its location within the body.

According to a further aspect of the invention, a biopsy instrument is provided having a proximal end and a distal end. The biopsy instrument includes a distal assembly, an elongate flexible member connected to and extending in a proximal direction from the distal assembly, and a proximal actuation handle coupled to the proximal end of the flexible member. The flexible member includes an irrigation conduit and an aspiration conduit. The proximal actuation handle includes an irrigation port in fluid connection with the proximal end of the irrigation conduit and an aspiration port in fluid connection with the proximal end of the aspiration conduit. The irrigation port is for fluid connection with a fluid source; the aspiration port is for fluid connection with a suction device.

In another aspect, the invention may include a control member connected to and extending from the distal assembly to the proximal actuation handle. The proximal actuation handle may include means for actuating the control member and the distal assembly. Furthermore, the distal assembly may include a stationary jaw and a movable jaw. The movable jaw is pivotable relative to the stationary jaw. The movable jaw is in fluid connection with either the irrigation conduit or the aspiration conduit; the stationary jaw is in fluid connection with the other. The distal assembly forms a fluid passageway between the irrigation conduit and the aspiration conduit when the movable jaw and the stationary jaw are in a closed position.

In a still further aspect of the present invention, the biopsy instrument includes a proximal actuation handle, and an elongate flexible member connected to and extending from the proximal actuation handle and having an irrigation conduit for fluid connection with a fluid source and for supplying a fluid to the distal end of the biopsy instrument. The biopsy instrument further includes a distal assembly for use in a surgical operation, and a means for permitting an operator to selectively increase fluid pressure in the irrigation conduit thereby causing a surge in fluid flow through the biopsy instrument. The distal assembly is attached to the distal end of the flexible member. The means for permitting an operator to selectively increase fluid pressure in the irrigation conduit may include a fluid pressure device in fluid connection with the irrigation conduit. The fluid pressure device may include a contractible fluid accumulating chamber.

The invention may include an aspiration conduit for fluid connection with a vacuum source and for permitting the flow of fluid from the distal end to the proximal end of the biopsy instrument. The biopsy instrument may also include an actuator on the proximal actuation handle, a control conduit on the elongate flexible member, and a control member extending through the control conduit. The control member is connected to and extends from the actuator to the distal assembly. Furthermore, the distal assembly may include a stationary jaw and a movable jaw. The movable jaw is pivotable relative to the stationary jaw. The movable jaw is in fluid connection with either the irrigation conduit or the aspiration conduit; the stationary jaw is in fluid connection with the other. The distal assembly may form a fluid passageway between the irrigation conduit and the aspiration conduit when the movable jaw and the stationary jaw are in a closed position. A sample collector assembly may be provided in-line with the aspiration conduit and the vacuum source and located therebetween. An irrigation valve in fluid connection with the irrigation conduit and the fluid source may be provided. The irrigation valve is configured to start and stop a fluid flow in the irrigation conduit. A suction valve in fluid connection with the aspiration conduit and the vacuum source may also be provided. The suction valve is configured to start and stop a vacuum effect in the aspiration conduit.

According to a further aspect of the invention, a method is provided for retrieving a biopsy tissue sample using the biopsy instrument having irrigation and aspiration capabilities in conjunction with a fluid pressure device. The biopsy instrument includes a proximal actuation handle, an elongate flexible member extending from the proximal actuation handle and having an irrigation conduit, a distal assembly located at the distal end of the biopsy instrument, and a fluid pressure device in fluid connection with the irrigation conduit. The method comprises the steps of: inserting the distal end of the biopsy instrument into a patient; positioning the distal assembly proximate to a tissue to be sampled; detaching the tissue sample from a surrounding tissue using the distal assembly; introducing a flow of fluid through the fluid pressure device and the irrigation conduit; actuating the fluid pressure device to cause a surge in fluid flow through the distal end of the biopsy instrument to flush the tissue sample through an aspiration conduit configured for fluid connection with a vacuum source and for permitting fluid to flow from the distal end to the proximal end of the biopsy instrument; and recovering the tissue sample.

The method may include the steps of: manipulating an actuator connected to a control member which is connected to a movable jaw of the distal assembly, whereby manipulating the actuator opens the distal assembly; moving the open distal assembly so as to encompass the tissue to be sampled; and re-manipulating the actuator to close the distal assembly and detach the tissue sample. Additionally, method may include initiating a vacuum effect in the aspiration conduit after the detaching step. Furthermore, the method may include repeating the steps of positioning, detaching, introducing, actuating, and recovering for subsequent tissue samples.

According to another aspect, the invention comprises a sample collector having a catcher handle and a catcher body. The sample collector is for use with a biopsy instrument having a suction passageway with a proximal end access opening. The catcher handle has a securing end for insertion into the access opening. The securing end of the catcher handle may complement the access opening to provide a seal therewith. The catcher body has a screen, may be removably attached to the securing end of the catcher handle, and is positionable within the suction passageway upon insertion of the securing end into the access opening. The catcher body may fit a pathology processing cartridge. The sample collector may be provided with a cover. The cover is positionable between an open position displaced from the catcher body and a closed position overlaying the catcher body.

In an additional aspect of the invention, a biopsy instrument with aspiration capabilities is provided having a distal assembly for use in a surgical operation, an elongate flexible member connected to and extending from the distal assembly to the proximal end, a proximal actuation handle with a suction passageway having an access opening, and a sample collector. The flexible member includes an aspiration conduit for fluid connection with a vacuum source and for permitting the passage of matter from the distal end to the proximal end. The suction passageway of the proximal actuation handle is in fluid connection with the aspiration conduit and capable of fluid connection with the vacuum source. The sample collector includes a catcher handle having a securing end for insertion into the access opening and a catcher body with a screen. The catcher body is positionable within the suction passageway upon insertion of the securing end into the access opening. Furthermore, the catcher body may be removably attached to the securing end of the catcher handle; the securing end may complement the access opening to provide a seal therewith; and the sample collector may include a cover positionable between an open position displaced from the catcher body and a closed position overlaying the catcher body. The flexible member of the biopsy instrument may include an irrigation conduit in fluid connection with a fluid source and for supplying fluid to the distal end of the biopsy instrument.

Additionally, the objects and purpose of the invention are obtained by a method of retrieving a biopsy sample using a biopsy instrument with aspiration capabilities in conjunction with an irrigation endoscope. The biopsy instrument includes a distal assembly, an elongate flexible member with an aspiration conduit, a proximal actuation handle, a vacuum source, and a sample collector. The proximal actuation handle includes a suction passageway in fluid connection with the aspiration conduit and having an access opening. The vacuum source is in fluid connection with the suction passageway. The sample collector has a catcher handle and a catcher body with a screen. The method comprises the steps of: introducing the remote end of the endoscope into a patient; engaging the sample collector into the access opening of the proximal actuation handle; inserting the distal end of the biopsy instrument through the working channel of the endoscope until the distal assembly is proximate the tissue to be sampled; obtaining the tissue sample using the distal assembly; initiating a vacuum effect in the suction passageway and the aspiration conduit to draw the tissue sample into the catcher body; and disengaging the sample collector from the proximal actuation handle.

In a further aspect of the invention, the method may include the step of establishing a temporary vacuum effect in the aspiration conduit to pull the tissue to be severed into the distal assembly. The method may also include the step of positioning a cover over the catcher body to entrap the tissue sample and of disconnecting the catcher body from the catcher handle. The method may further include the step of squirting irrigation fluid from the remote end of the irrigation endoscope. The initiated vacuum effect draws the squirted irrigation fluid and tissue sample through the aspiration conduit and suction passageway to the screen of the catcher body. Finally, the introducing, engaging, inserting, obtaining, initiating, and disengaging steps of the method may be repeated for subsequent tissue samples.

According to a still further aspect of the invention, the biopsy instrument includes a proximal actuation handle, an elongate flexible member, and a distal end effector assembly for use with an irrigation endoscope in a surgical operation. The elongate flexible member, connected to and extending from the proximal actuation handle, has an aspiration conduit for fluid connection with a vacuum source and for permitting the flow of fluid from the distal end to the proximal end of the biopsy instrument. The biopsy instrument may include a sample chamber, a sample catch member, and a valve which regulates the vacuum in the aspiration conduit.

The distal end effector assembly, comprised of first and second hollow movable jaws, is coupled to the distal end of the tubular member. The first and second hollow movable jaws are pivotably coupled adjacent the aspiration conduit to the tubular member. With the jaws in a closed position, the end effector assembly provides a substantially fluidtight passageway at the distal end of the aspiration conduit. The movable jaws may be made from metal or plastic and may have sharp cutting edges, teeth for grasping, or other matching profiles. The movable jaws are further coupled to the control member, such that actuation of the actuation handle moves the movable jaws relative to the tubular member, thereby opening and closing the distal end effector assembly.

It will be appreciated that with both jaws of the distal end effector assembly being capable of opening and closing, the biopsy instrument may be better positioned around the tissue to be sampled.

Additional objects and advantages of the invention will become apparent to those skilled in the art upon reference to the detailed description taken in conjunction with the provided Figures.

BRIEF DESCRIPTION OF THE DRAWINGS

FIG. 2 is a broken perspective view of the proximal end of the biopsy instrument of FIG. 1;

FIG. 3 is a broken perspective view of the sample chamber of the biopsy instrument of FIG. 1;

FIG. 4 is a perspective view of the front side of the sample catch member of the biopsy instrument of FIG. 1;

FIG. 5 is a perspective view of the back side of the sample catch member of the biopsy instrument of FIG. 1;

FIG. 6 is an enlarged broken perspective view of the tubular member of the biopsy instrument of FIG. 1;

FIG. 15 is an enlarged broken transparent perspective view of the tubular member of the biopsy instrument of FIG. 14;

FIG. 21 is an enlarged broken transparent perspective view of the tubular member of another embodiment of the invention;

FIG. 22 is an enlarged cross-section across line 22-22 of FIG. 21;

DETAILED DESCRIPTION OF THE PREFERRED EMBODIMENTS

Figure 1:
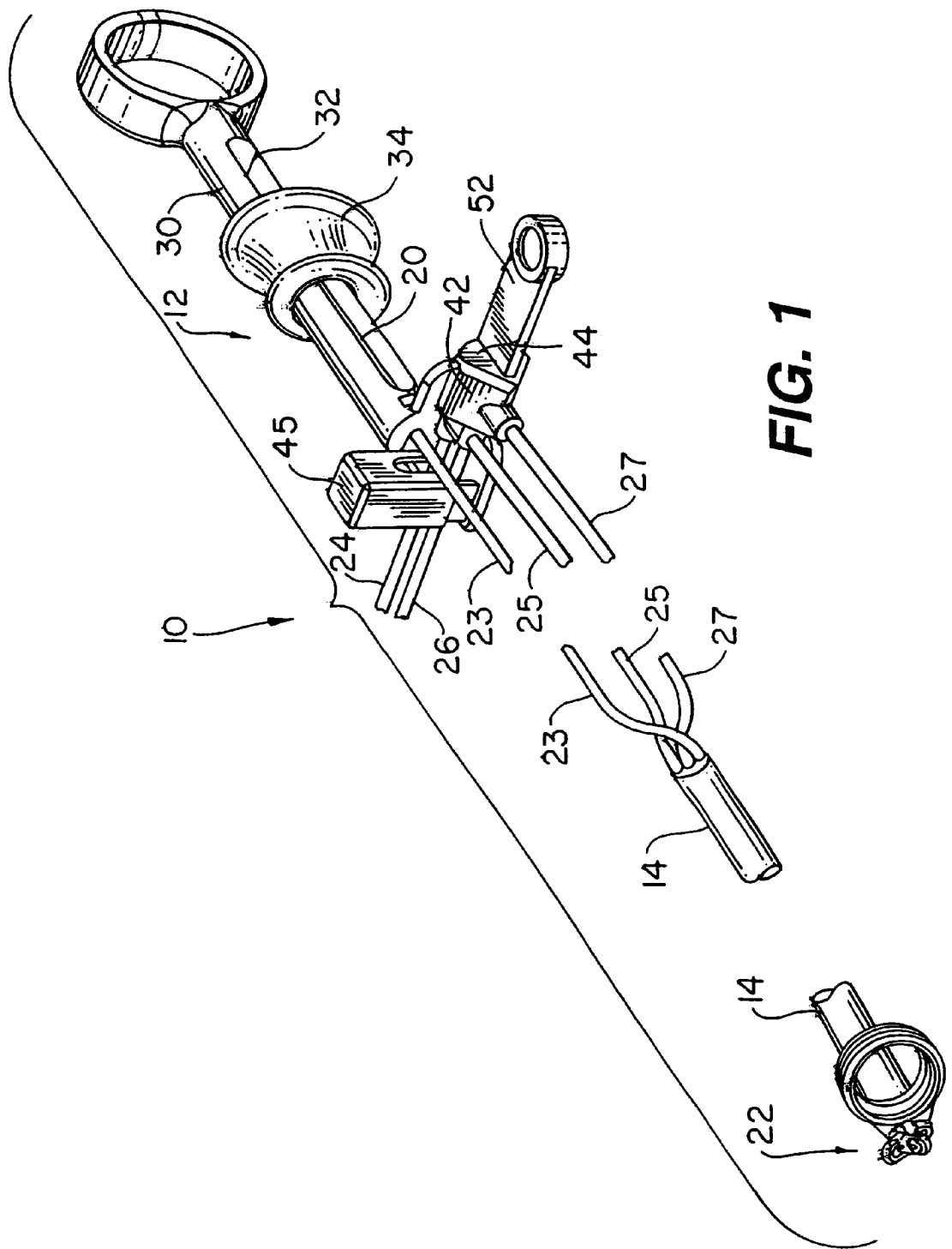
FIG. 1 is a broken perspective view of a first embodiment of an endoscopic biopsy instrument according to the invention.

Turning now to FIG. 1, a multiple sample biopsy instrument 10 is shown. The biopsy instrument generally includes a proximal actuation handle 12, a flexible multi-lumen tubular member 14, a pull wire 20, and a distal assembly 22. Several coupling tubes are preferably provided to couple the proximal actuation handle 112 to the tubular member 14 and to irrigation and aspiration means. In particular, a control coupling tube 23, first and second irrigation coupling tubes 24, 25 and first and second aspiration coupling tubes 26, 27 are provided.

The proximal actuation handle 12 includes a shaft 30 having a transverse slot 32 and a spool 34 slidably mounted on the shaft 30 and having a transverse bar (not shown) extending through the slot 32, as is common in the art. The actuation handle 12 is provided with a sample chamber 42, a sample catch member 44, and a pinch valve 45 which regulates irrigation and aspiration. Turning to FIG. 2, the sample chamber 42 includes irrigation connectors 46, 47 which couple the first irrigation coupling tube 24 to the second irrigation coupling tube 25. The sample chamber 42 also includes first and second aspiration connectors 48, 49 which couple the first aspiration coupling tube 26 to the second aspiration coupling tube 27. Referring to FIGS. 3-5, the sample catch member 44 includes a handle portion 52, an engagement portion 54 which removably engages the sample catch member 44 to the sample chamber 42, and a screen 56. The screen 56 extends through the sample chamber 42 between the first and second aspiration connectors 48, 49. The screen 56 includes a front side 58 and a back side 60 and is provided with a plurality of perforations 62 which are preferably frustoconical in shape and expand from the front side 58 to the back side 60. The first irrigation coupling tube 26 and the first aspiration coupling tube 27 extend through the pinch valve 45 which operates to control the flow of fluid through the tubes 26, 27. The pinch valve is biased to clamp closed the first irrigation coupling tube 26 and the first aspiration coupling tube 27, i.e, to collapse the tubes on top of each other. Pressing downward on the pinch valve 45 with a practitioner's finger counters the bias of the pinch valve to permit fluid flow through the first irrigation coupling tube 26 and the first aspiration coupling tube 27.

Figure 7:
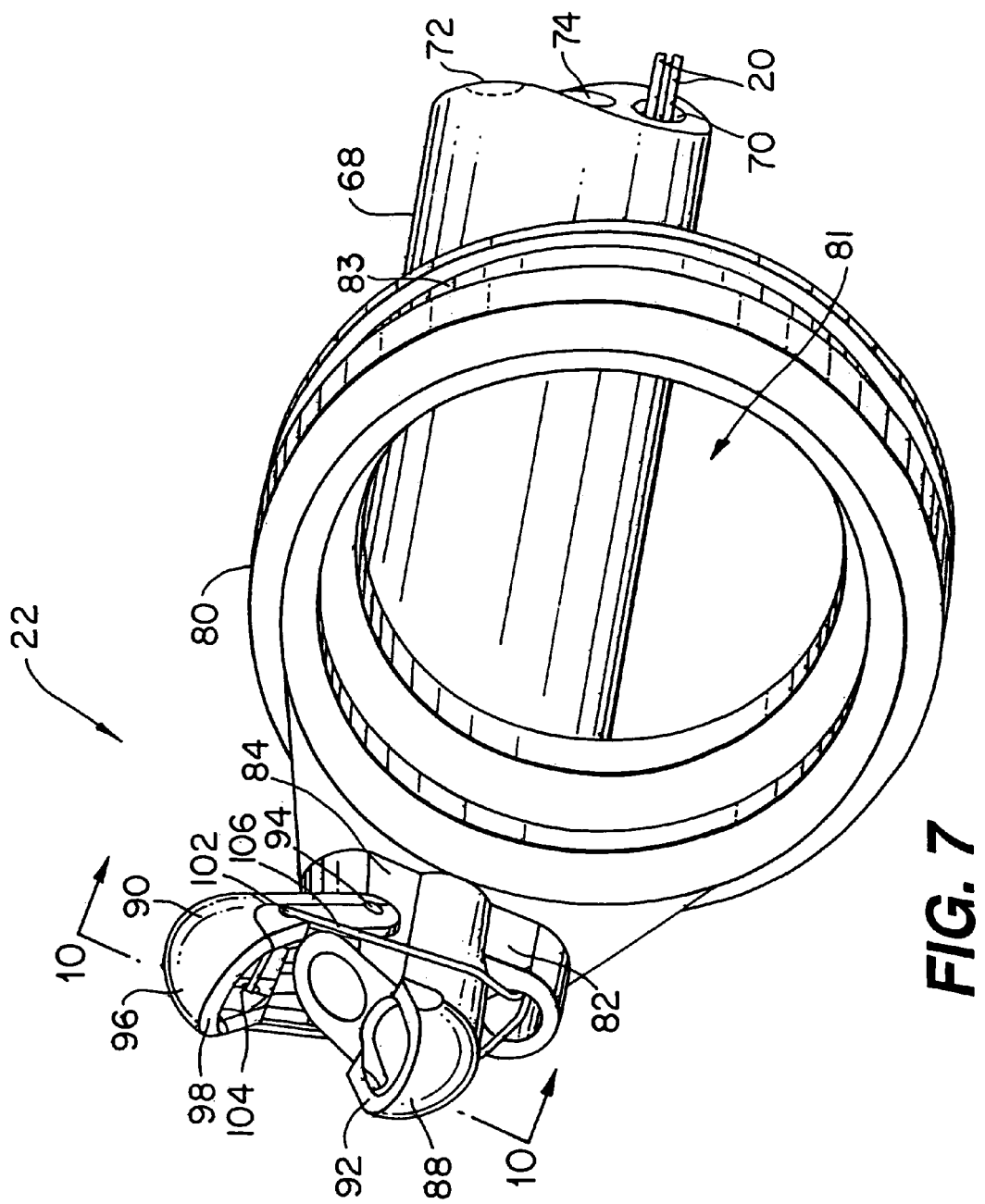
FIG. 7 is an enlarged broken perspective view of the distal assembly of the biopsy instrument of FIG. 1 with the jaws in an open position.

Turning to FIGS. 6 and 7, and in accord with the first embodiment of the invention, the tubular member 14 is preferably an ovoid multi-lumen extrusion. The tubular member includes a proximal end 66, a distal end 68, a control conduit 70 an irrigation conduit 72, and an aspiration conduit 74, each of which extends through the tubular member to the distal assembly 22. At the proximal end 66 of the tubular member, the control conduit 70 is coupled to the control coupling tube 23, the irrigation conduit 72 is coupled to the second irrigation coupling tube 25 and the aspiration conduit 74 is coupled to the second aspiration coupling tube 27.

Figure 9:
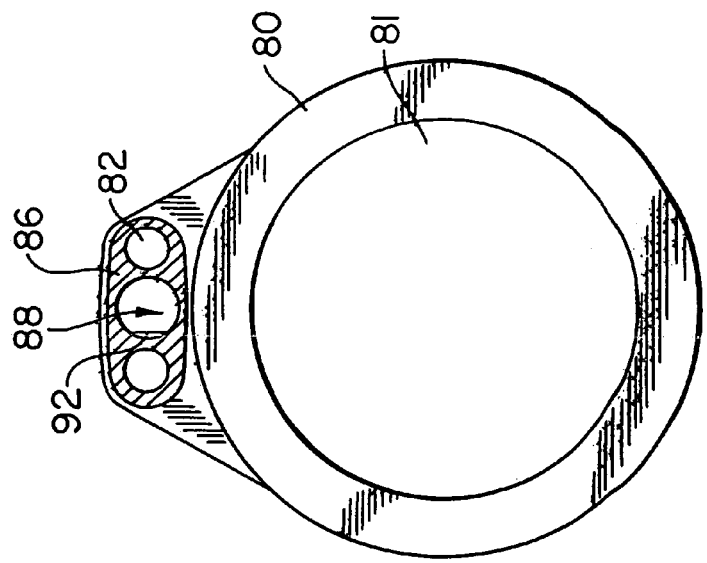
FIG. 9 is a bottom end view of FIG. 8.
Figure 8:
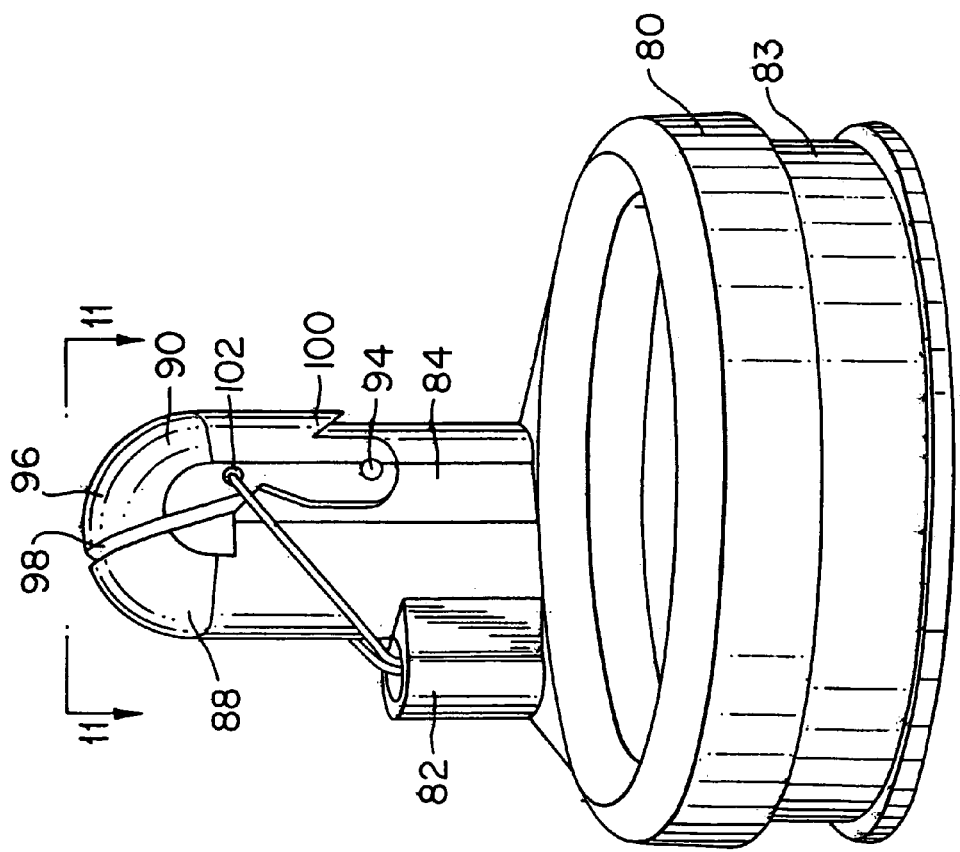
FIG. 8 is an enlarged broken perspective view of the distal assembly of the biopsy instrument of FIG. 1 with the jaws in a closed position.

Referring to FIGS. 7 through 9, the distal assembly 22 includes a substantially rigid molded collar 80 and a hollow movable jaw 90. The collar 80 is preferably made from a unitary piece of polycarbonate, a glass-filled polycarbonate, a hard grade styrene, or other plastic, while the movable jaw 90 is preferably made from cast metal. The collar includes a central opening 81, a circumferential channel 83, a distally extending control passage 82, a distally extending hollow jaw mount 84, a distally extending hollow stationary jaw 88, and a proximal socket 86. The central opening 81 of the collar 80 is of similar diameter to the outer diameter of the endoscope and is designed to couple the collar to the outside of the distal end of an endoscope. The circumferential channel 81 receives a portion of a silicone rubber sock (not shown), which is used to secure collar 80 to the endoscope.

Stationary jaw 88 preferably includes blunt edge or lip 92. Movable jaw 90 is pivotably mounted at pivot pin 94 on jaw mount 84 and is pivotable relative to stationary jaw 88. The movable jaw 90 is preferably provided with a sharp cutting edge 98, a stop 100 for limiting the extent to which the movable jaw pivots away from the stationary jaw 88, and two jaw holes 102, 104, for receiving a pull wire 20, as described below.

Figure 11:
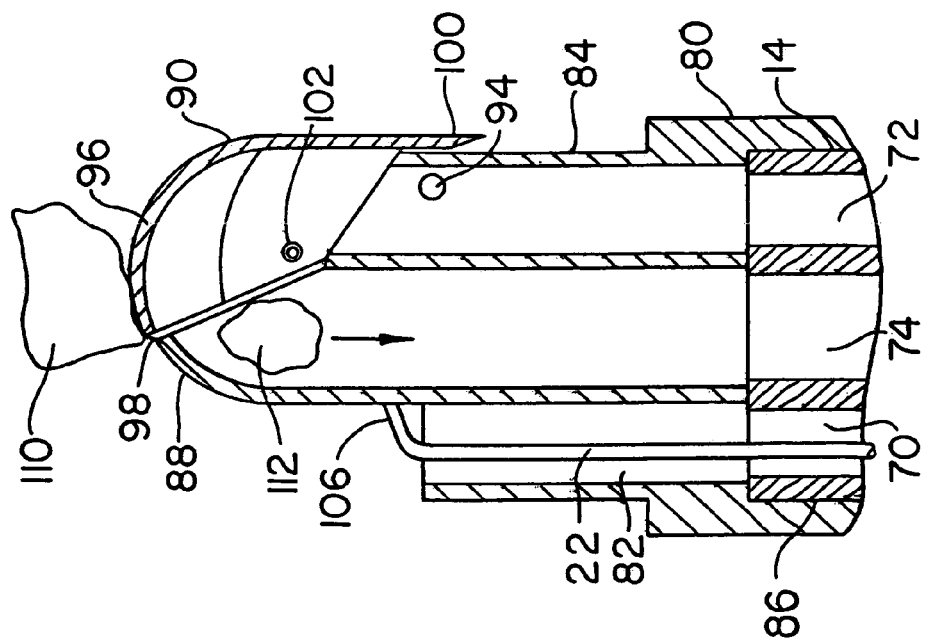
FIG. 11 is cross section across line 11-11 of FIG. 8.
Figure 10:
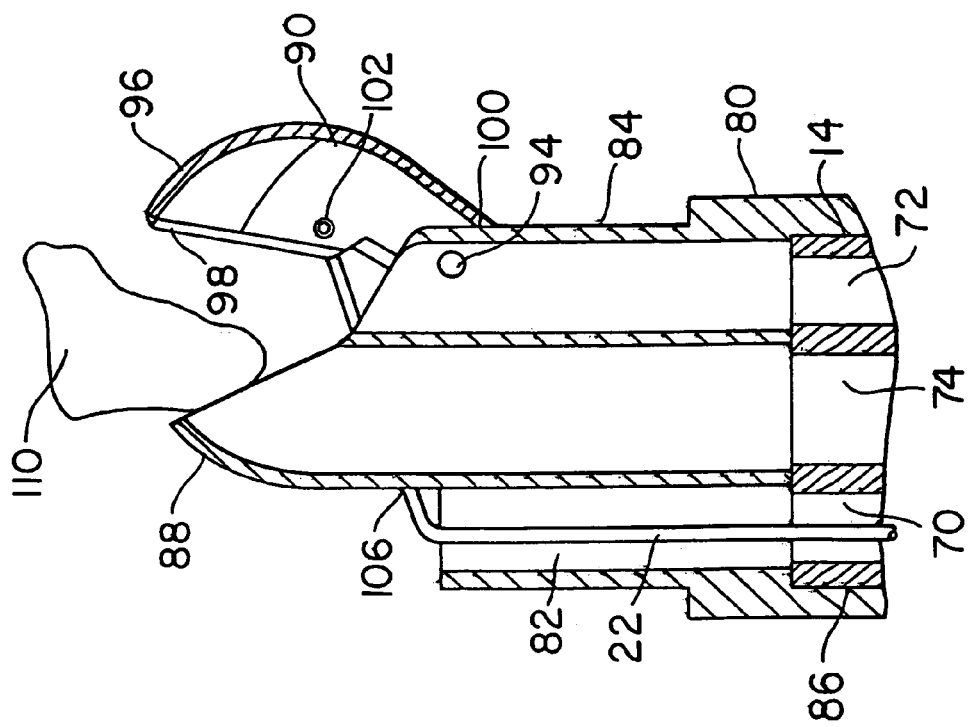
FIG. 10 is a cross section across line 10-10 of FIG. 7.

Referring to FIGS. 9 through 11, the proximal socket 86 is aligned with the control passage 82, the jaw mount 84 and the stationary jaw 88, and is designed to receive the distal end 68 of the flexible tubular member 14. The distal end 68 of the tubular member is secured in the proximal socket 86, preferably using an adhesion bonding agent, such that the control passage 82 is coupled to the control conduit 70, the jaw mount 84 is coupled substantially fluidtight to the irrigation conduit 72, and the stationary jaw 88 is coupled substantially fluidtight to the aspiration conduit 74.

Figure 13:
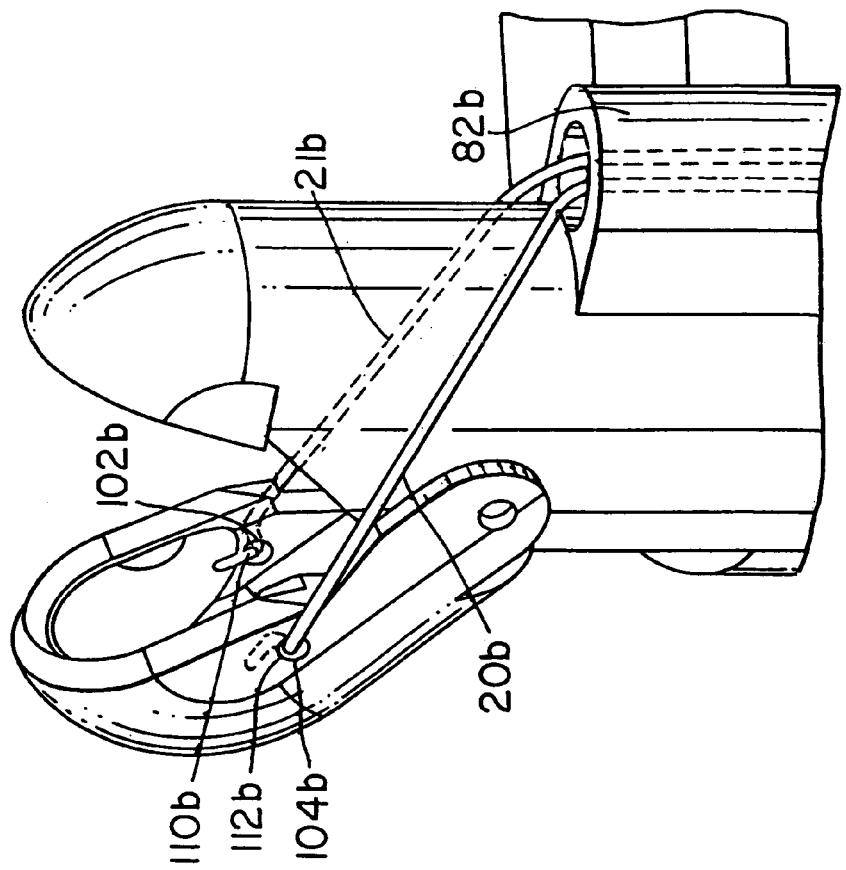
FIG. 13 is a broken perspective view of the distal assembly of the biopsy instrument of FIG. 1 illustrating another alternative control member configuration.
Figure 12:
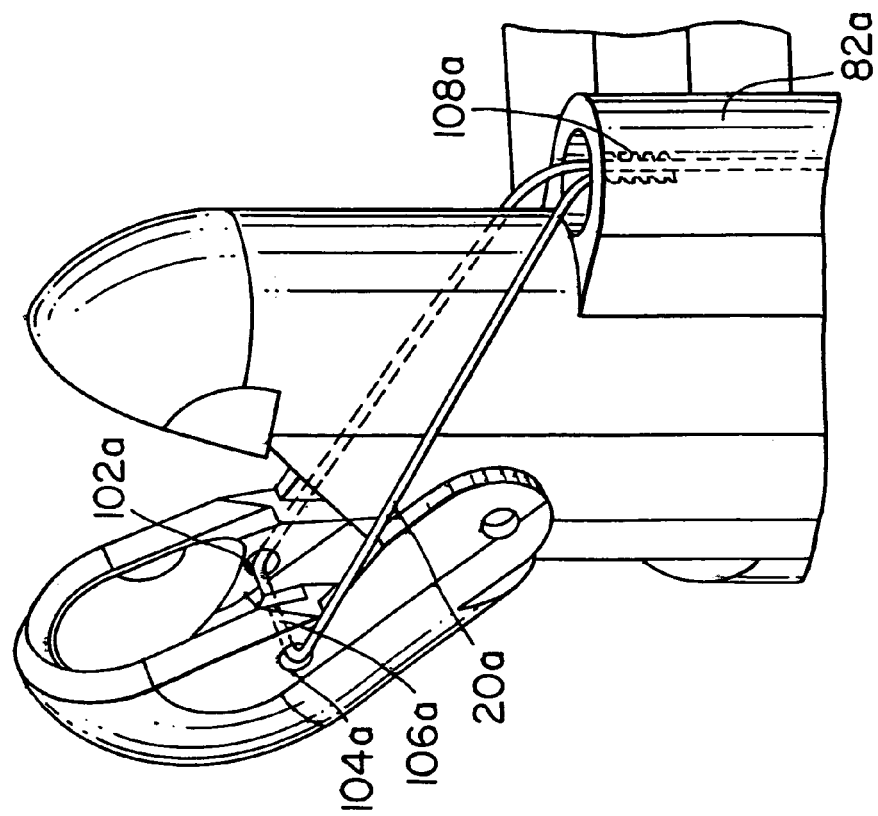
FIG. 12 is a broken perspective view of the distal assembly of the biopsy instrument of FIG. 1 illustrating an alternative control member configuration.

Turning back to FIGS. 1, 6, 7 and 10, a central portion of the pull wire 20 extends through the jaw holes 102, 104 and the ends of the pull wire 20 extend through the control passage 82, the control conduit 74, and the control coupling tube 23 to the spool 34. Referring to FIG. 12, alternatively the pull wire 20a forms a secure loop 106a through the jaw holes 102a, 104a by doubling back on itself and forming a twist 108a. Referring to FIG. 13, in yet another alternative, two pull wires 20b, 21b may be used, the distal end of each pull wire being coupled to a jaw hole 102b, 104b by a Z-bend 110b, 112b and extending through the control passage 82b.

Referring to FIGS. 1, 7, and 8, it will be appreciated that movement of the spool 34 relative to the shaft 30 results in movement of the pull wire 20 relative to the tubular member 14 and consequently moves the movable jaw 90 relative to the stationary jaw 88 such that the jaws open (FIG. 7) and close (FIG. 8). Referring to FIGS. 7 through 11, when the stationary and movable jaws 88, 90 are in a closed position a substantially fluidtight passage is formed therebetween. Because the stationary jaw 88 is coupled to the aspiration conduit 74 and the movable jaw 90 is coupled over the irrigation conduit 72, a substantially fluidtight coupling of the irrigation and aspiration conduits is achieved.

In use, it will be appreciated that the distal end of the endoscope to which the collar 80 is coupled is maneuvered adjacent the desired tissue for sampling and the distal assembly is brought into contact with tissue 110 (FIGS. 10 and 11). The actuation handle 12 is actuated to close the jaws 88, 90 and cut off a tissue sample 112. When the jaws 88, 90 are in a closed position the irrigation means and the aspiration means are activated and the first proximal irrigation coupling tube and the first proximal aspiration coupling tube 24, 26 are released from the clamping action of the pinch valve 45 by depressing the pinch valve. Irrigating fluid is thereby permitted to flow through the first and second proximal irrigation coupling tubes 24, 26, through the irrigation conduit 72 and the hollow jaw mount 84, and to the jaws 88, 90 at the distal end of the instrument. The fluid flows through the jaws and is aspirated back to the proximal end of the instrument such that the sample held within the jaws is aspirated with the water. Turning back to FIGS. 2-6, as the water is aspirated through the aspiration conduit 74 and into the sample chamber 42, the sample is filtered onto the screen 58. The frustoconical shape of the perforations 62 permits increased fluid flow through the perforate screen while preventing the tissue sample from passing through the screen. Irrigation and aspiration means are interrupted by releasing the pinch valve 45 such that the pinch valve clamps down on the first proximal irrigation and aspiration coupling tubes 24, 26 and causes the tubes to collapse on top of each other. The screen 58 may easily be removed to retrieve the sample by gripping the handle portion 52 of the sample catch member 44 and pulling the sample catch member from the sample chamber 42. The sample is recovered from the screen, and the sample catch member is reinserted into the sample chamber to continue the procedure. It will be further appreciated that the entire procedure of cutting a sample and retrieving the sample may be performed without removing the endoscopic multiple sample biopsy forceps instrument from its location within the body. Unlimited subseguent samples may be obtained in an identical manner.

Figure 14:
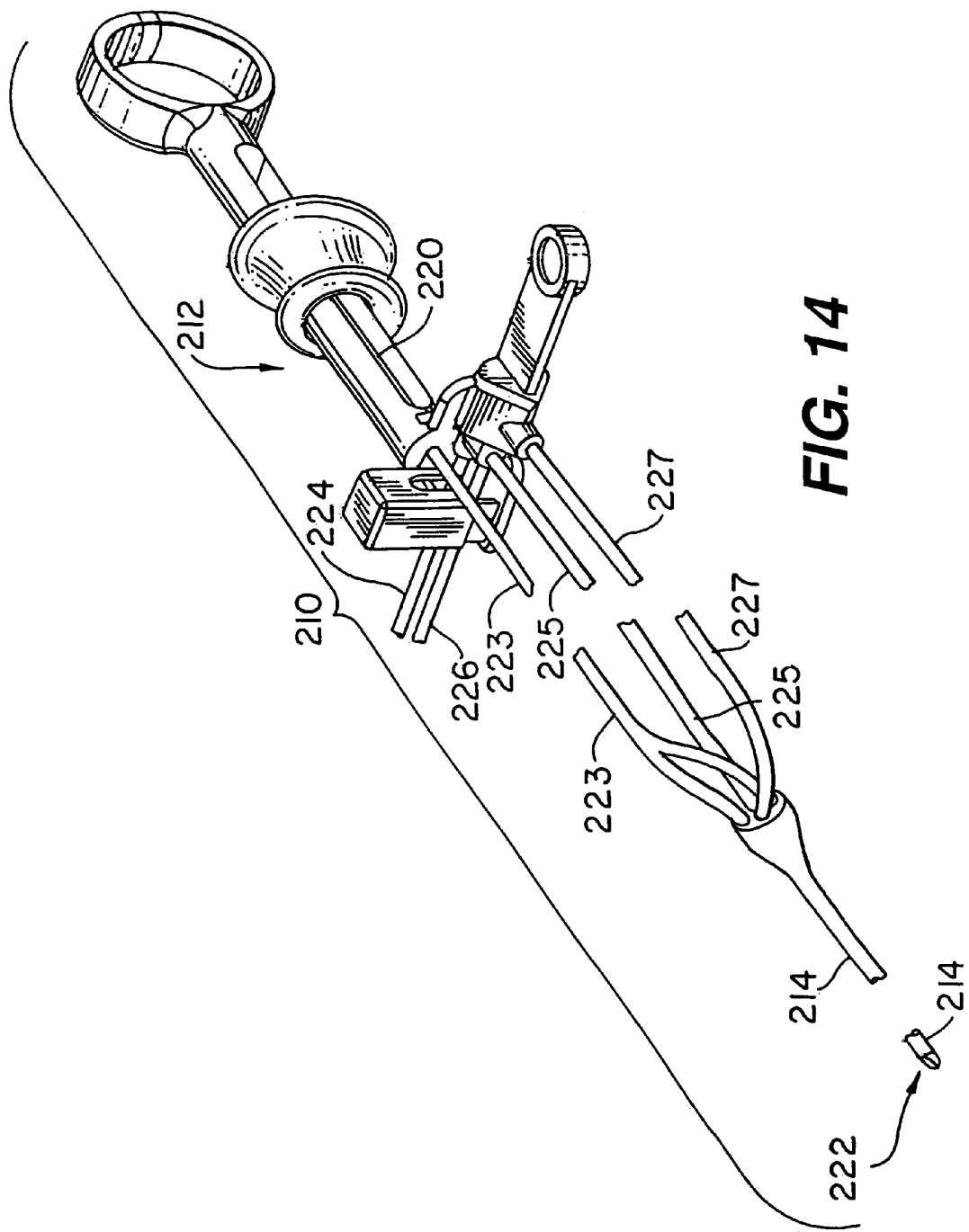
FIG. 14 is a broken perspective view of an alternative embodiment of an endoscopic biopsy instrument of the invention.

Turning to FIGS. 14 and 15, a second embodiment of a multiple sample biopsy forceps instrument 210 is shown. The instrument includes a proximal actuation hande 212, a flexible multi-lumen tubular member 214, a pull wire 220, and a distal assembly 222. Several coupling tubes are preferable provided to couple the proximal actuation handle 212 to the tubular member 214 and to irrigation and aspiration means. In particular, a Y-shaped control coupling tube 223, first and second irrigation coupling tubes 224, 225, and first and second aspiration coupling tubes 226, 227 are provided.

Figure 16:
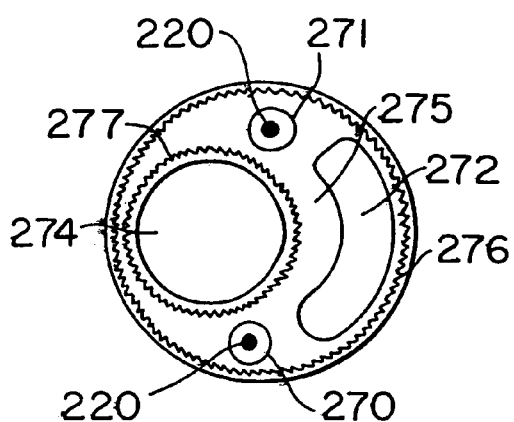
FIG. 16 is an enlarged cross section across line 16-16 of FIG. 15.
Figure 17:
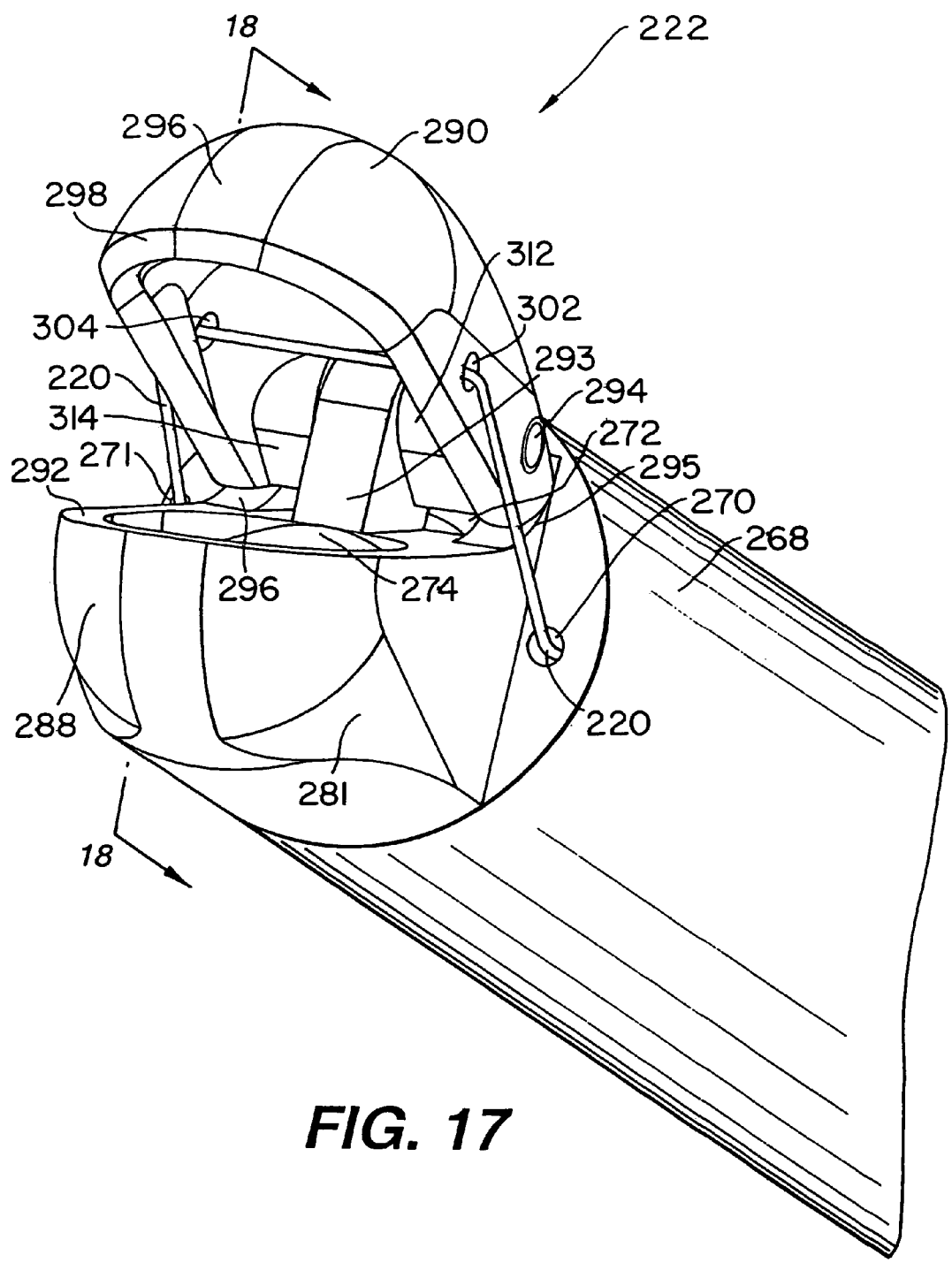
FIG. 17 is an enlarged broken perspective view of the distal assembly of the biopsy instrument of FIG. 14 with the jaws in an open position.
Figure 19:
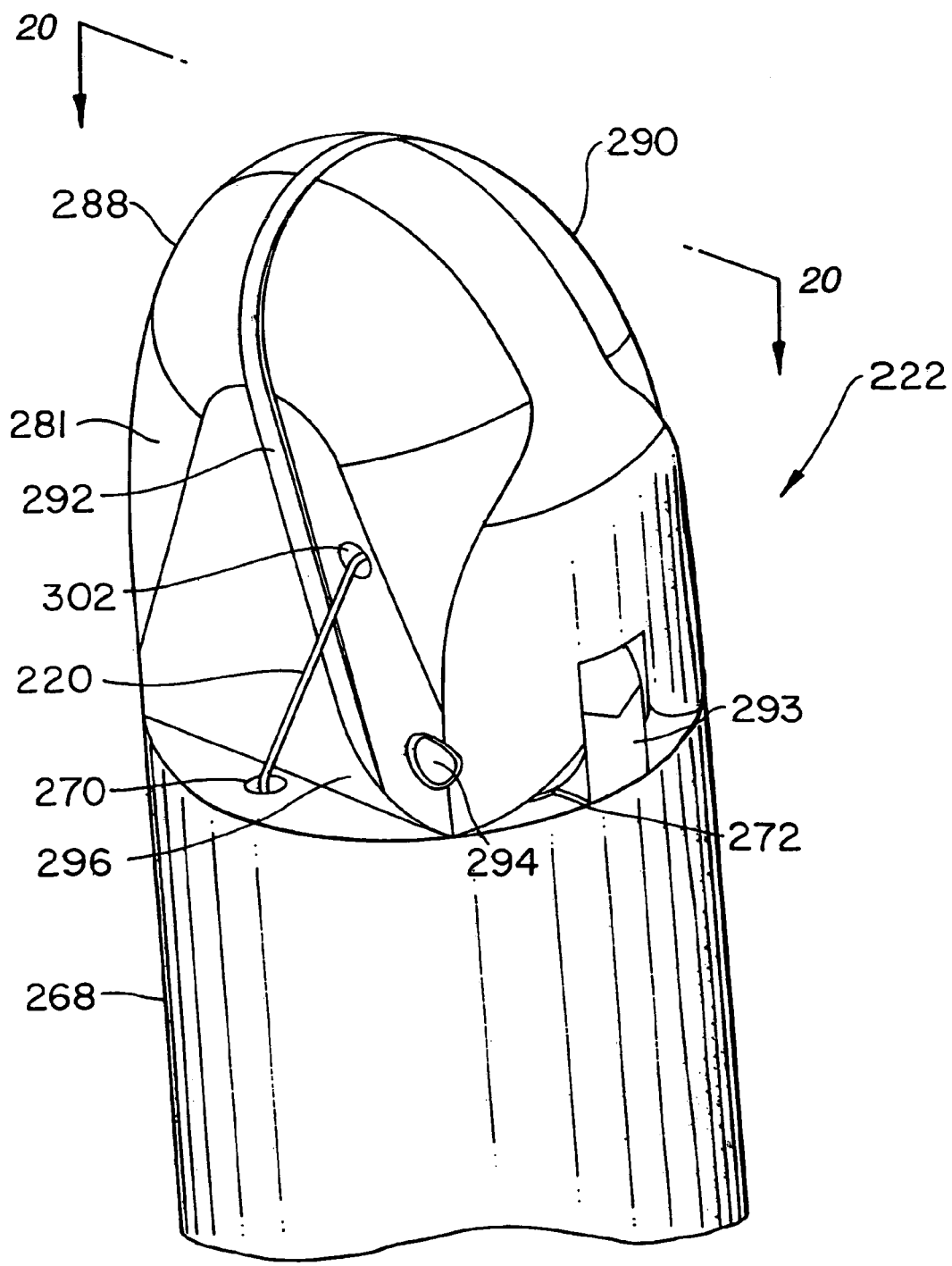
FIG. 19 is an enlarged broken perspective view of the distal end of the biopsy instrument of FIG. 14 with the biopsy jaws in a closed-position.

The proximal actuation handle 212 is substantially similar to the first embodiment (with like parts having numbers incremented by 200). Referring to FIGS. 15, 16 and 17, the tubular member 214 is preferably a multi-lumen multi-layer extrusion, and preferably includes a first metal braid 276 beneath the outermost layer to add desired stiffness to the tubular member. If desired, a second metal braid 277 may be additionally provided around the aspiration conduit 274 to stiffen and support the aspiration conduit 274. The tubular member 214 has a proximal end 266, distal end 268, two control conduits 270, 271, an irrigation conduit 272, and an aspiration conduit 274, each of the conduits 270, 271, 272, 274 extending through the tubular member to the distal assembly 222. The aspiration conduit 274 has a substantially circular cross section. The irrigation conduit 272 has a generally kidney-shaped cross section and is separated from the aspiration conduit 274 by a membrane 275. The control conduits 270, 271 are preferably situated one on either end of the membrane 275.

Referring to FIGS. 17-20, the distal assembly 222 according to a second embodiment of the invention includes a stationary jaw 281 coupled, preferably by adhesion bonding, to the distal end 268 of the tubular member. The stationary jaw 281, preferably made of plastic includes a jaw cup 288, an integral central clevis 293 and integral proximal ramps 295, 296. The jaw cup 288 is located over the aspiration conduit 274 and preferably has a blunt cutting surface or lip 292. The central clevis 293 and proximal ramps 295, 296 extend from the stationary jaw 281 and abut and partially cover the irrigation conduit. A movable jaw 290, preferably made of metal, is provided with a sharp cutting edge 298, defines two jaw holes 302, 304 for receiving a pull wire 220, and is provided with two bosses 312, 314 for mounting the jaw. The bosses 312, 314 loosely engage the central lug 293 and a pivot pin 294 extends through the bosses and the central lug. The ramps 295, 296 of the stationary jaw 281 guide the movable jaw 290 when opening and closing and assist to form a substantially fluidtight passage between the movable jaw 290 and the stationary jaw cup 288 when the jaws are in a closed position. A central portion of the pull wire 220 which is perpendicular to the longitudinal axis of the instrument extends through the jaw holes 302, 304 and the ends of the pull wire extend into the control conduits 270, 271. Turning back to FIG. 15, the Y-shaped coupling tube 223 facilitates alignment of the ends of the pull wire 220 for coupling the pull wire to the proximal actuation handle. The pull wire 220 may be coated, e.g., in a plastic, to inhibit the pull wire from cutting into the tubular member.

Figure 20:
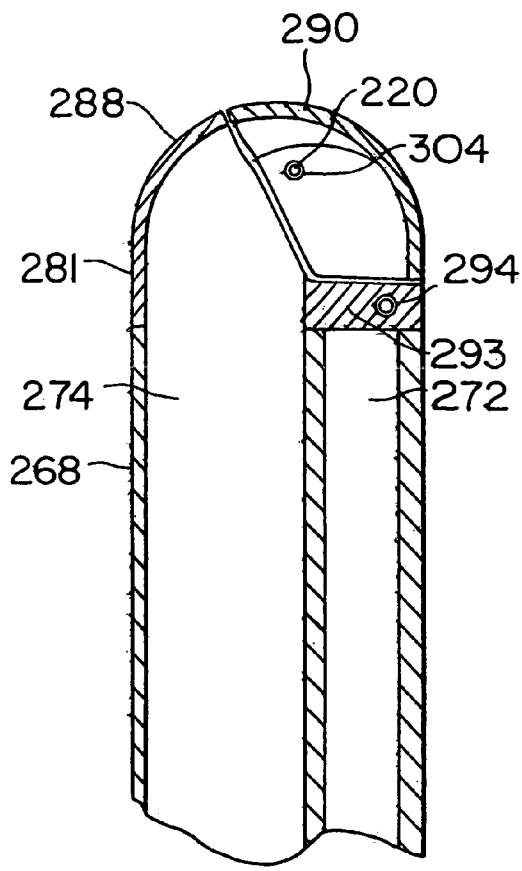
FIG. 20 is a cross section across line 20-20 of FIG. 19.
Figure 18:
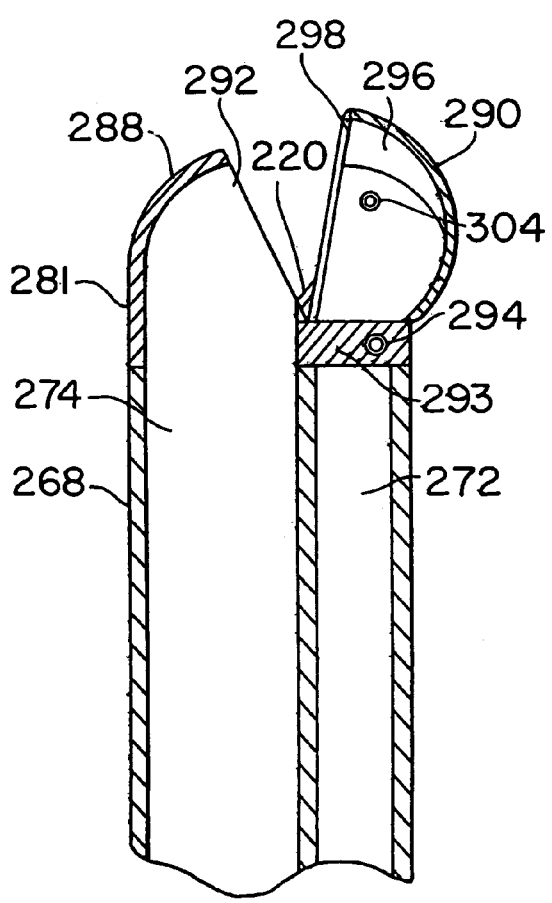
FIG. 18 is a cross section across line 18-18 of FIG. 17.

Referring to FIGS. 18 and 20, the distal end 268 of the tubular member is inserted through the lumen of an endoscope to a biopsy site. The jaws 281, 290 are moved into a closed position cutting off a tissue sample and further providing a substantially fluidtight coupling between the irrigation and aspiration conduits 272, 274. While it appears from the illustrations of FIGS. 18 and 20 that the irrigation conduit 272 is obstructed at the distal end by clevis 293, it will be appreciated that the irrigation conduit 272 is substantially wider than the clevis and that fluid may flow around the clevis to the aspiration conduit 274.

Figure 23:
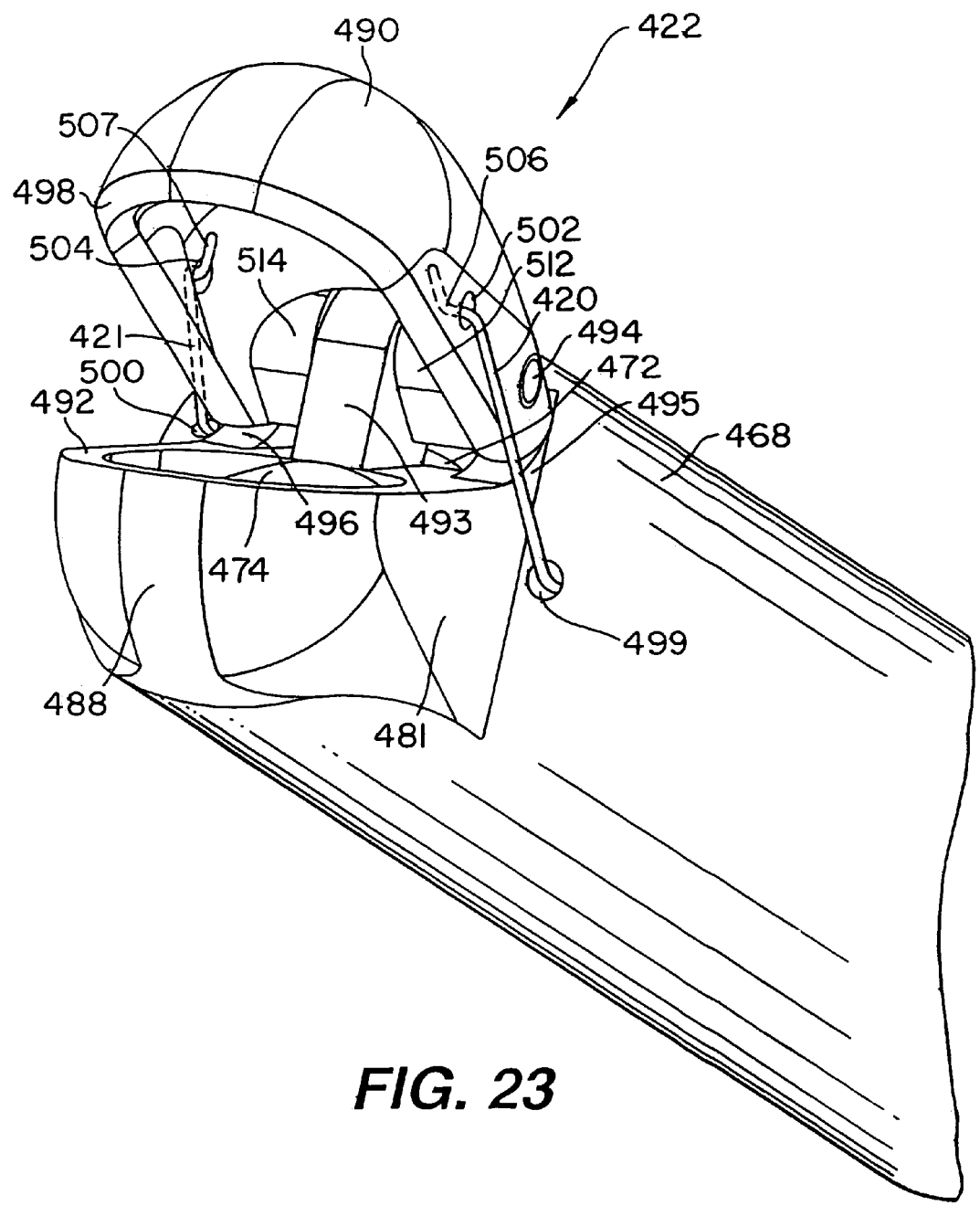
FIG. 23 is a enlarged broken perspective view of the distal end of the biopsy instrument of FIG. 21 with the jaws in an open position.

Turning now to FIGS. 21-23, a third embodiment of a multiple sample biopsy forceps, substantially similar to the second embodiment (with like parts having numbers incremented by another 200) is shown. The tubular member 414 has a proximal end 466, a distal end 468, an irrigation conduit 472, and an aspiration conduit 474. The aspiration conduit 474 has a substantially circular cross section, while the irrigation conduit 472 has a generally crescent-shaped cross section. A control coupling tube 423 is coupled to the second irrigation coupling tube 425. Two pull wires 420, 421 extend through the control coupling tube 423, pass through a substantially fluidtight valve (not shown) coupling the control coupling tube 423 and the second irrigation coupling tube 425, enter into the second irrigation coupling tube 425, and extend through the irrigation conduit 472 to the distal end 468 of the tubular member. An aspiration coupling tube 427 is coupled to the aspiration conduit 474.

Referring to FIG. 23, the distal assembly 422 of the third embodiment of the invention includes a stationary jaw 481 bonded to the distal end 468 of the tubular member, and a movable jaw 490 coupled thereto. The stationary jaw 481 includes a jaw cup 488, an integral central clevis 493, and ramps 495, 496. The jaw cup abuts the distal end of the tubular member and is positioned over the aspiration conduit 474 and preferably has a blunt cutting surface or lip 492. The central clevis 493 and ramps 495, 496 extend from the stationary jaw 481 and abut and partially cover the irrigation conduit 474. A movable jaw 490, preferably made or metal, is provided with a sharp cutting edge 498, defines two jaw holes 402, 404 for receiving a pull wire 420, and is provided with two bosses 512, 514 for mounting the jaw. The bosses 512, 514 loosely engage the central clevis 493 and a pivot pin 494 extends through the bosses and the central clevis. By partially covering the irrigation conduit, the ramps form entrances 499, 500 for the pull wires, as described below. The movable jaw 490 rides on the proximal ramps 495, 496 when moving from an open to a closed position. The pull wires 420, 421 are coupled to the jaw holes 502, 504 by a Z-bend 506, 507 and extend through the entrances 499, 500 into the irrigation conduit 472, through a portion of the second irrigation coupling tube 425, and further into a control coupling tube 423 coupled thereto. The entrances 499, 500 are sufficiently small that only an insubstantial amount of fluid exits from the irrigation conduit when the jaws are in a closed position and irrigant is forced through the irrigation conduit 474 to the distal assembly.

There have been described and illustrated herein several embodiments of a multiple sample endoscopic biopsy instrument. While particular embodiments of the invention have been described, it is not intended that the invention be limited thereto, as it is intended that the invention be as broad in scope as the art will allow and that the specification be read likewise. Therefore, while a particular manner of coupling the proximal actuation handle to the distal assembly has been disclosed for the several embodiments, it will be appreciated that other manners of coupling the proximal and distal assemblies may be used as well. Furthermore while the stationary jaw is disclosed as preferably being made of plastic and the movable jaw is disclosed as being made of metal it will be appreciated both the stationary jaw and the movable jaw may be made from plastic, metal, or another material. Moreover, while the movable jaw is disclosed as preferably being made from cast metal, it will be appreciated that the movable jaw, when made of metal, may alternatively be made by machining or M.I.M. Further, while both jaws are shown without teeth, one or both of the jaws may include teeth along their mating surface. In fact, the teeth may be arranged radially as disclosed in co-owned U.S. Pat. No. 5,507,296. Also, while one or two pull wires are disclosed with respect to certain embodiments, it will be appreciated that in each embodiment either one or two pull wires may be used, in manners described herein. Furthermore, while the stationary jaw is disclosed as being coupled to the aspiration conduit and the movable jaw is disclosed as being coupled to the irrigation conduit, it will be appreciated that the stationary jaw may be coupled to the irrigation conduit and the movable jaw may be coupled to the aspiration conduit. Moreover, it will be appreciated that both the jaws may be movable about the distal end of the tubular member. In addition, while particular configurations have been disclosed in reference to coupling the proximal actuation handle to the tubular member, it will be appreciated that other configurations can be used as well. It will therefore be appreciated by those skilled in the art that yet other modifications could be made to the provided invention without deviating from its spirit and scope as so claimed.

The present invention, therefore, is not limited to the particular embodiments described in connection with FIGS. 1-23. The following description provides still further embodiments of a biopsy instrument having irrigation and aspiration capabilities. For example, the embodiment of a biopsy instrument according to the present invention and shown in FIG. 24 generally relates to a biopsy instrument having irrigation and aspiration capabilities and including irrigation and aspiration ports.

Figure 24:
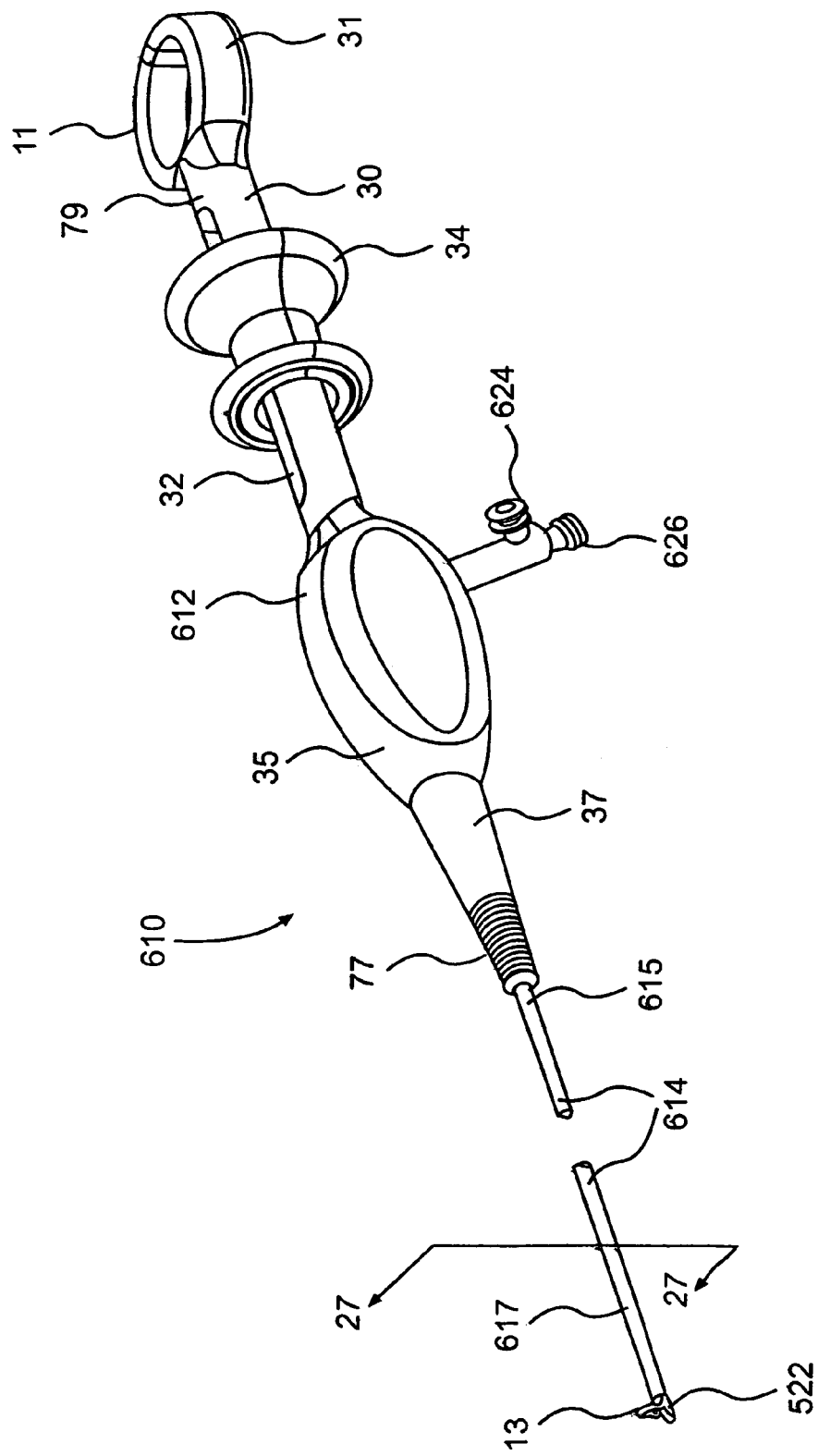
FIG. 24 is a perspective view of a biopsy instrument in accordance with a further embodiment of the present invention.

A biopsy instrument according to the embodiment of FIG. 24 generally includes a proximal actuation handle, a distal assembly, and an elongate flexible member connecting the proximal actuation handle to the distal assembly. The elongate flexible member includes an irrigation conduit and an aspiration conduit, both extending from the distal to the proximal end. The proximal actuation handle includes an irrigation port and an aspiration port. The irrigation port, located at the proximal end of the irrigation conduit, is removably connectable to various fluid sources. The aspiration port, located at the proximal end of the aspiration conduit, is removably connectable to a vacuum source or to a variety of suction retrieval devices. These general portions of the biopsy instrument will now be more specifically described. The operation of the biopsy instrument will be described thereafter.

In accordance with the embodiment of FIG. 24, there is provided a biopsy instrument having a proximal end and a distal end. A multiple sample biopsy instrument 610 is shown with proximal end 11 and distal end 13. Biopsy instrument 610 generally includes a distal assembly 522 at distal end 13, a proximal actuation handle 612 at proximal end 11, and an elongate flexible member 614 connecting distal assembly 522 to proximal actuation handle 612. During a surgical procedure, proximal end 11 remains external to a patient's body and under the direct physical control of the surgeon. Distal end 13 is inserted into a passageway or cavity of the patient's body and is positioned proximate to the remote internal operation site. In the preferred embodiment, distal end 13 of biopsy instrument 610 is inserted into and threaded through an endoscope (not shown) which has previously been inserted into the patient's body and positioned proximate to the operation site.

The biopsy instrument according to the embodiment of FIG. 24 includes a distal assembly for use in a surgical operation. Distal assembly 522 is connected to flexible member 614 at distal end 13 of biopsy instrument 610.

Figure 25:
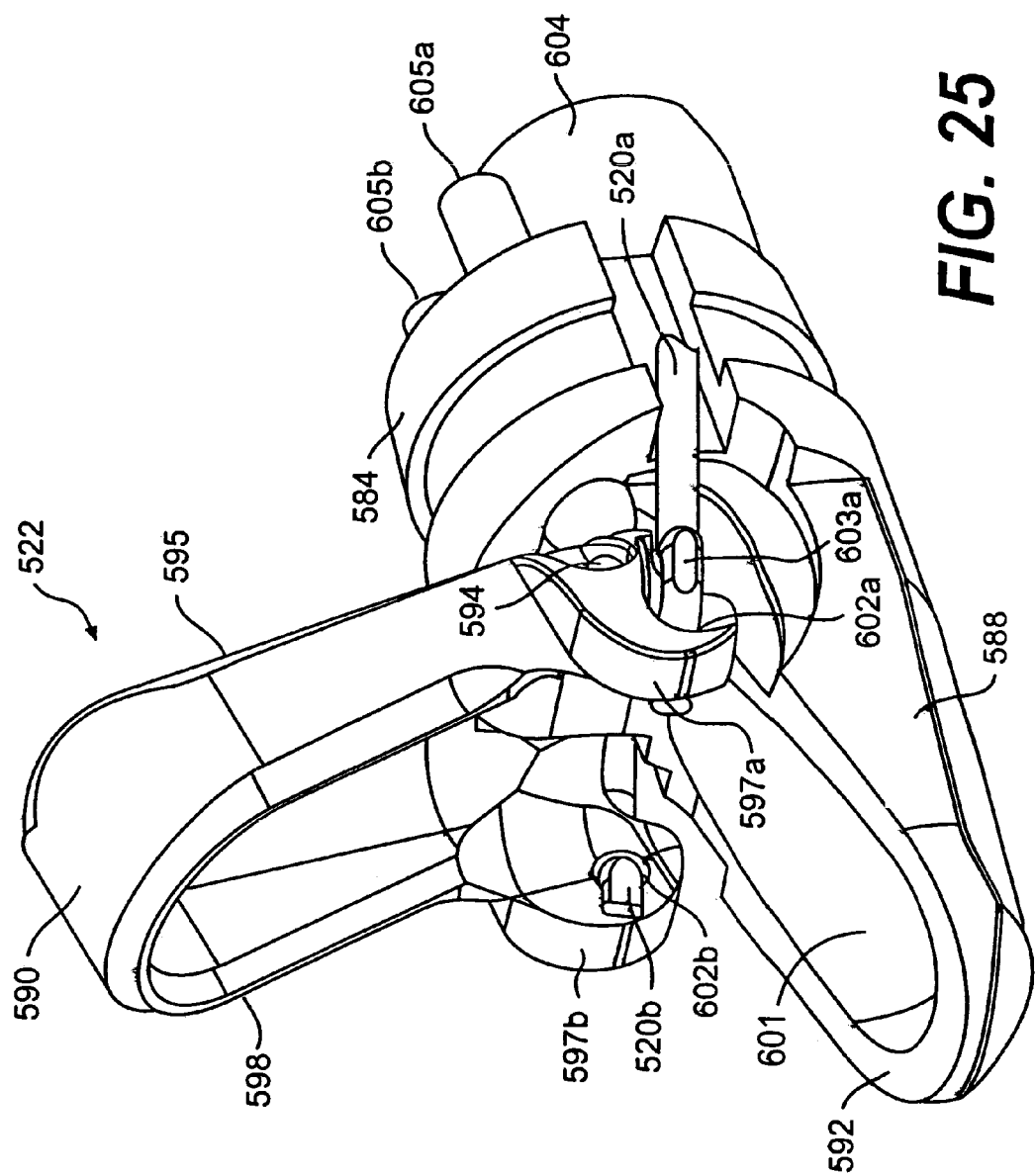
FIG. 25 is a perspective view of a distal portion of the biopsy instrument of FIG. 24.
Figure 26:
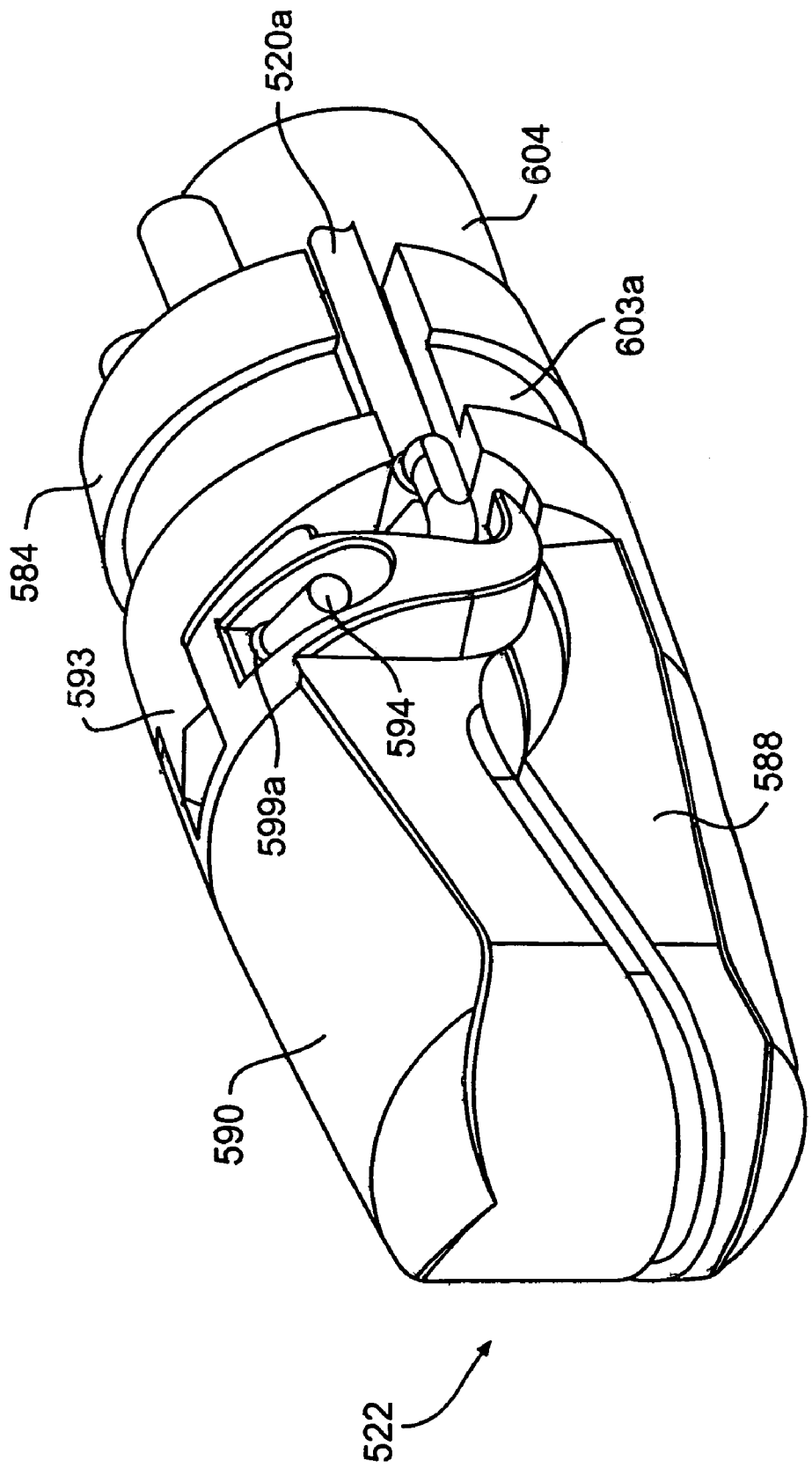
FIG. 26 is a perspective view of a distal portion of the biopsy instrument of FIG. 24.

In a preferred embodiment and as illustrated in FIGS. 25 and 26, distal assembly 522 includes jaw mount 584, movable jaw 590, opposing stationary jaw 588 and pivot pin 594. Distal assembly 522 is shown in an opened configuration in FIG. 25 and in a closed configuration in FIG. 26. As shown in FIG. 26, jaw mount 584 includes a flange 593 for retaining pivot pin 594 and a conduit mounting stub 604 for facilitating attachment to flexible member 614, as described below. As shown in FIG. 25, movable jaw 590 includes cup-like body 595, sharp cutting edge 598, pivot holes 599a, 599b for receiving pivot pin 594, and two opposing clevis flanges 597a, 597b with holes 602a, 602b for receiving pull wires 520a, 520b, respectively. Stationary jaw 588 includes concave cavity 601 and blunt edge 529.

Stationary jaw 588 is fixedly connected to jaw mount 584. Stationary jaw 588 may be integrally formed with jaw mount 584, or stationary jaw 588 may be welded, bonded, screwed or otherwise fixedly attached to jaw mount 584.

As shown in FIGS. 25 and 26, movable jaw 590 is pivotably mounted to jaw mount 584. Movable jaw 590 pivots about pivot pin 594 and relative to jaw mount 584 and stationary jaw 588 to open and close distal assembly 522. Distal assembly 522 is in a closed configuration when cutting edge 598 abuts blunt edge 592. Movable jaw 590 may be provided with a stop (not shown) for limiting the extent to which jaw 590 pivots away from stationary jaw 588. Alternatively, such a stop could be located on jaw mount 584.

Referring to FIG. 25, movable jaw 590 is pivotably attached to distal ends of pull wires 520a, 520b. The distal ends of pull wires 520a, 520b are bent at right angles, inserted through holes 602a, 602b, respectively, and then further bent at right angles to provide a retention feature. Thus, no additional parts are required to attach pull wires 520a, 520b to the distal assembly. Pull wires 520a, 520b might also be provided with a U-shaped portion 603a, 603b, respectively, proximate the distal end for accommodating a portion of the clevis flange 597a, 597b.

Pull wires 520a, 520b extend in a proximal direction to proximal actuation handle 612. As described below, the proximal ends of pull wires 520a, 520b are connected, directly or indirectly, to actuation spool 34. This configuration allows a surgeon to cut a biopsy sample at the distal end of the biopsy instrument by manipulating actuation spool 34 at the proximal end of the biopsy instrument. Other embodiments with various control configurations are discussed above in connection with FIGS. 1-23. It is to be understood that the principles of these control configurations also may be applied to the biopsy instrument of FIG. 24.

In addition, it should be understood that while the previously described distal assembly of FIGS. 25 and 26 may be used in connection with the biopsy instrument of FIG. 24, other manipulable and non-manipulable distal assemblies may also be used without departing from the scope or spirit of the invention. For example, alternative distal assemblies include single and dual actuating jaws having cutting edges, teeth, matching projections for grasping enhancement, or combinations thereof. Furthermore, the principle and details of the distal assemblies shown in FIGS. 1-23 also may be applied to the biopsy instrument of FIG. 24.

The biopsy instrument according to the embodiment of FIG. 24 also includes an elongate flexible member connected to and extending from the distal assembly. Flexible member 614 has a proximal end 615 and a distal end 617. As described below, at proximal end 615, flexible member 614 is connected to the end of proximal actuation handle 612 opposite thumb ring 31. Also as described below, at distal end 617, flexible member 614 is attached to jaw mount 584.

Figure 27:
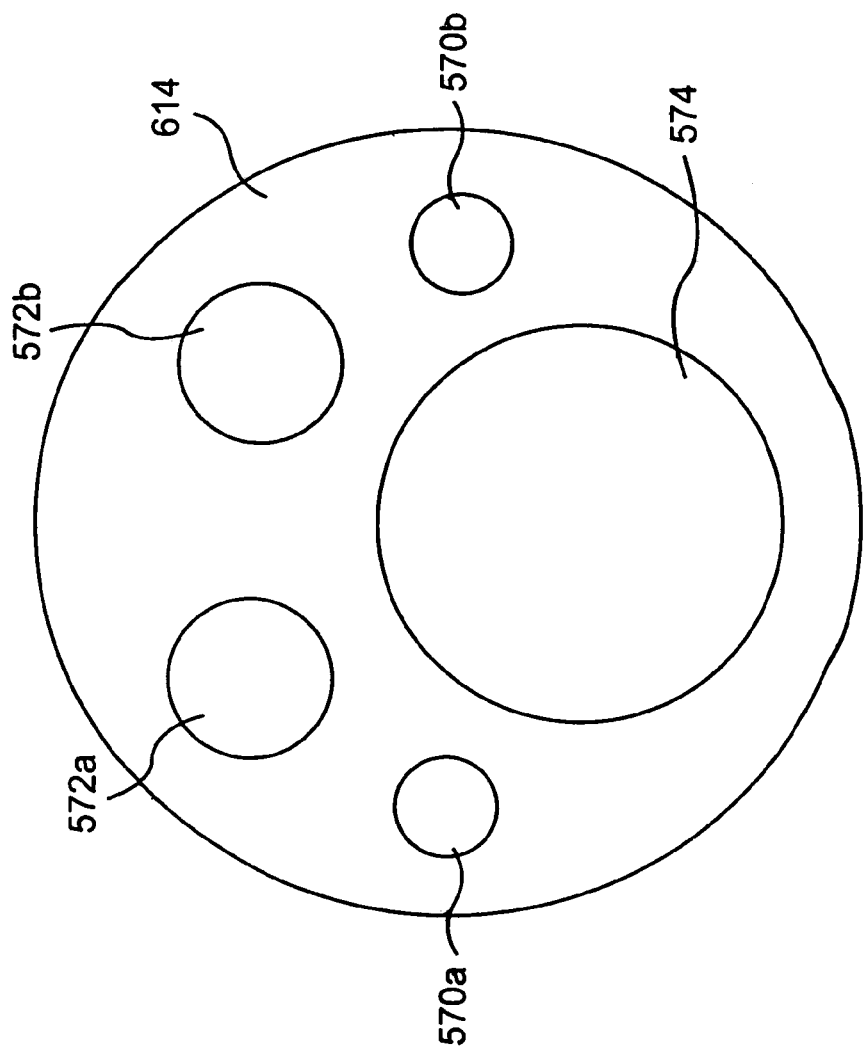
FIG. 27 is an enlarged cross-section across line 27-27 of FIG. 24.

In accordance with the embodiment of FIG. 24, the flexible member includes an irrigation conduit and an aspiration conduit. As best shown in FIG. 27, flexible member 614 has a generally cylindrical body with a pair of irrigation conduits 572a, 572b, an aspiration conduit 574, and a pair of control 11 cable conduits 570a and 570b. Irrigation conduits 572a, 572b and aspiration conduit 574, have generally circular cross sections and extend longitudinally through flexible member 614. Preferably, aspiration conduit 574 is of a diameter sufficient to retrieve biopsy samples from the distal end of the instrument. Control cable conduits 570a, 570b have generally circular cross sections, are diametrically opposed to each other, and extend longitudinally through flexible member 614. Conduits 570a, 570b provide channels through which pull wires 520a, 520b extend.

Flexible member 614 is preferably made of nylon, but any flexible, biologically compatible material may be used. Additionally, flexible member 614 may be surrounded by an elongate cylindrical sheath (not shown). It is to be understood that although the preferred embodiment of the flexible member has a circular cross section, and each of the irrigation, aspiration and control conduits has a circular cross section, the invention is not so limited. Furthermore, the invention is not limited by the number of individual irrigation, aspiration, or control conduits.

Distal end 617 of flexible member 614 is secured to jaw mount 584 of distal assembly 522. Aspiration conduit mounting stub 604 of jaw mount 584 may be inserted into the distal end opening of aspiration conduit 574 of flexible member 614. Flexible member 614 could be adhesively bonded to jaw mount 584, or a crimp band, or other mechanical attachment means could be used. In this way, aspiration of a biopsy tissue sample occurs through stub 604 to aspiration conduit 574. In addition, irrigation conduit mounting stubs 605a, 605b of jaw mount 584 may be inserted into the distal end opening of irrigation conduits 572a, 572b, respectively. Irrigation fluid is provided to the distal end of biopsy instrument 610 via irrigation conduits 572a, 572b, and irrigation conduit mounting stubs 605a, 605b.

In accordance with the embodiment of FIG. 24, the biopsy instrument includes a proximal actuation handle 612 located at proximal end 11 of biopsy instrument 610 and coupled to proximal end 615 of flexible member 614. Proximal actuation handle 612 has a front end 77 and a back end 79.

Figure 28:
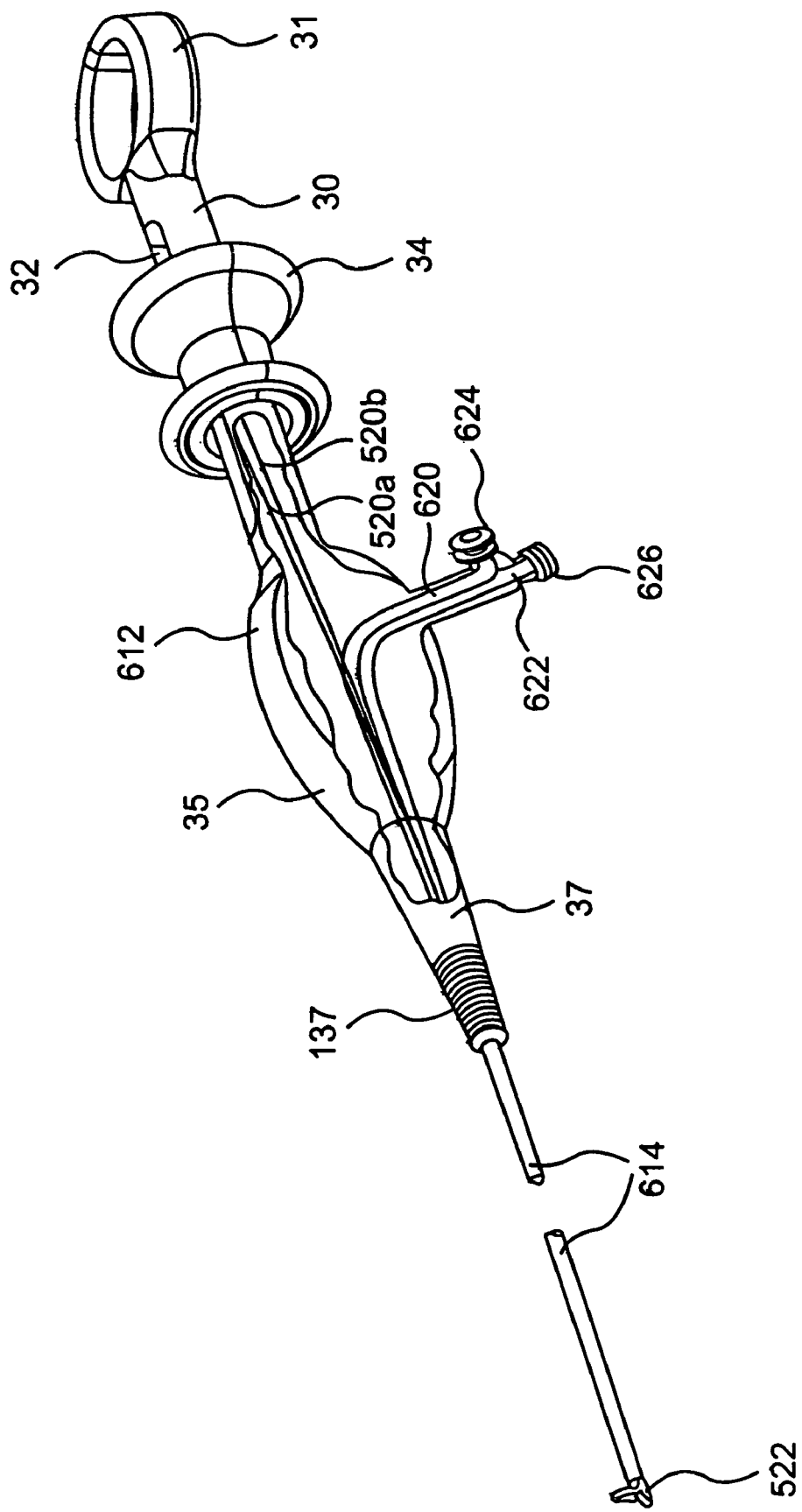
FIG. 28 is a perspective, partial cut-away view of the biopsy instrument of FIG. 24.
Figure 29:
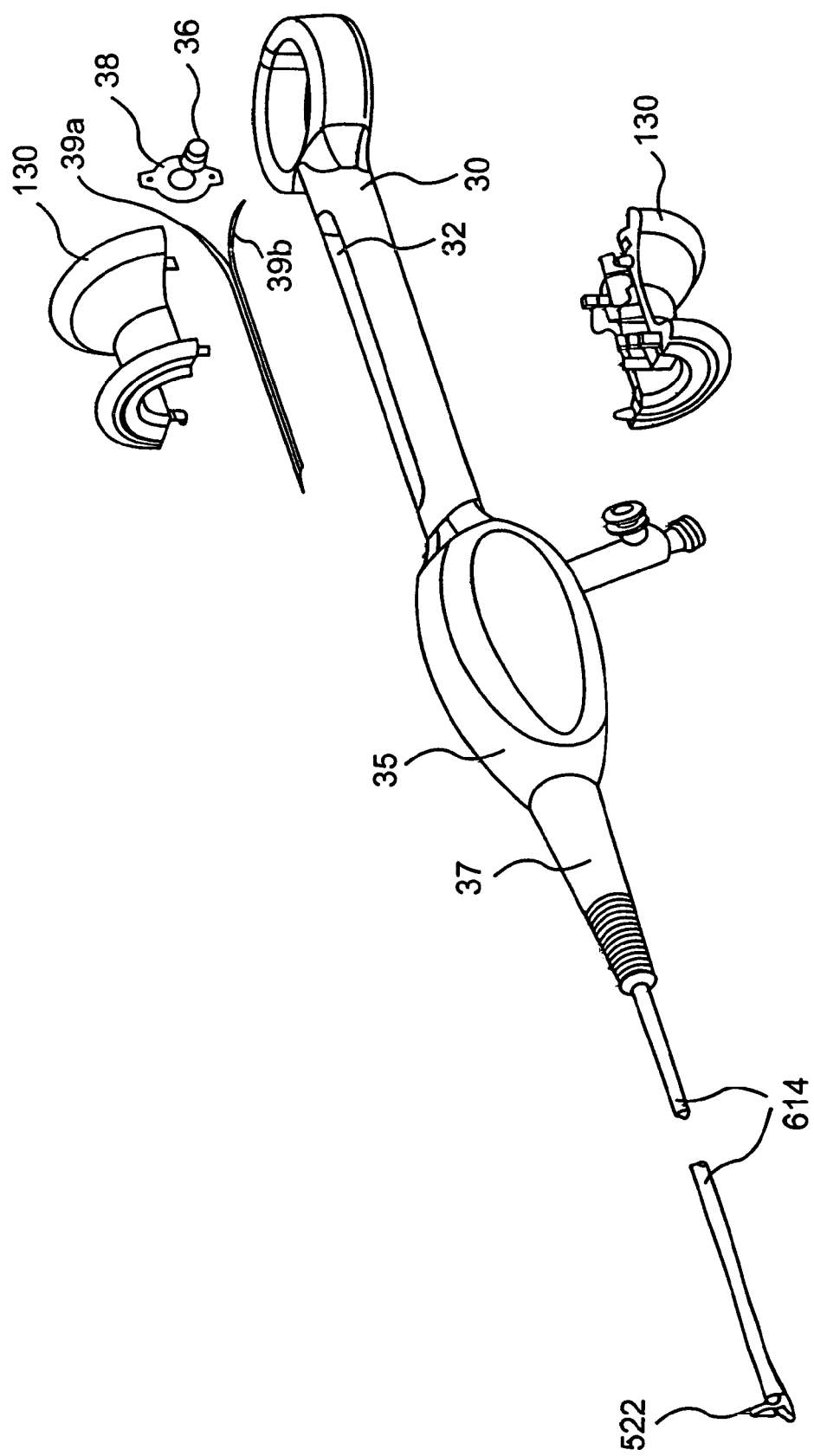
FIG. 29 is a partially exploded perspective view of the biopsy instrument of FIG. 24.

The proximal actuation handle 612 includes an elongate shaft, a thumb ring, an actuation spool, and a front end nose portion. As embodied herein and as shown in FIGS. 28 and 29, proximal actuation handle 612 includes shaft 30, thumb ring 31, actuation spool 34, body portion 35, and nose portion 37. Shaft 30 has a transverse through slot 32 extending most of the longitudinal length of shaft 30.

Thumb ring 31 is affixed to back end 79 of shaft 30. Ring 31 enables a surgeon to better grip and control biopsy instrument 610. Ring 31 is connected to the end of proximal actuation handle 612 opposite the end connected to flexible member 614.

Figure 30:
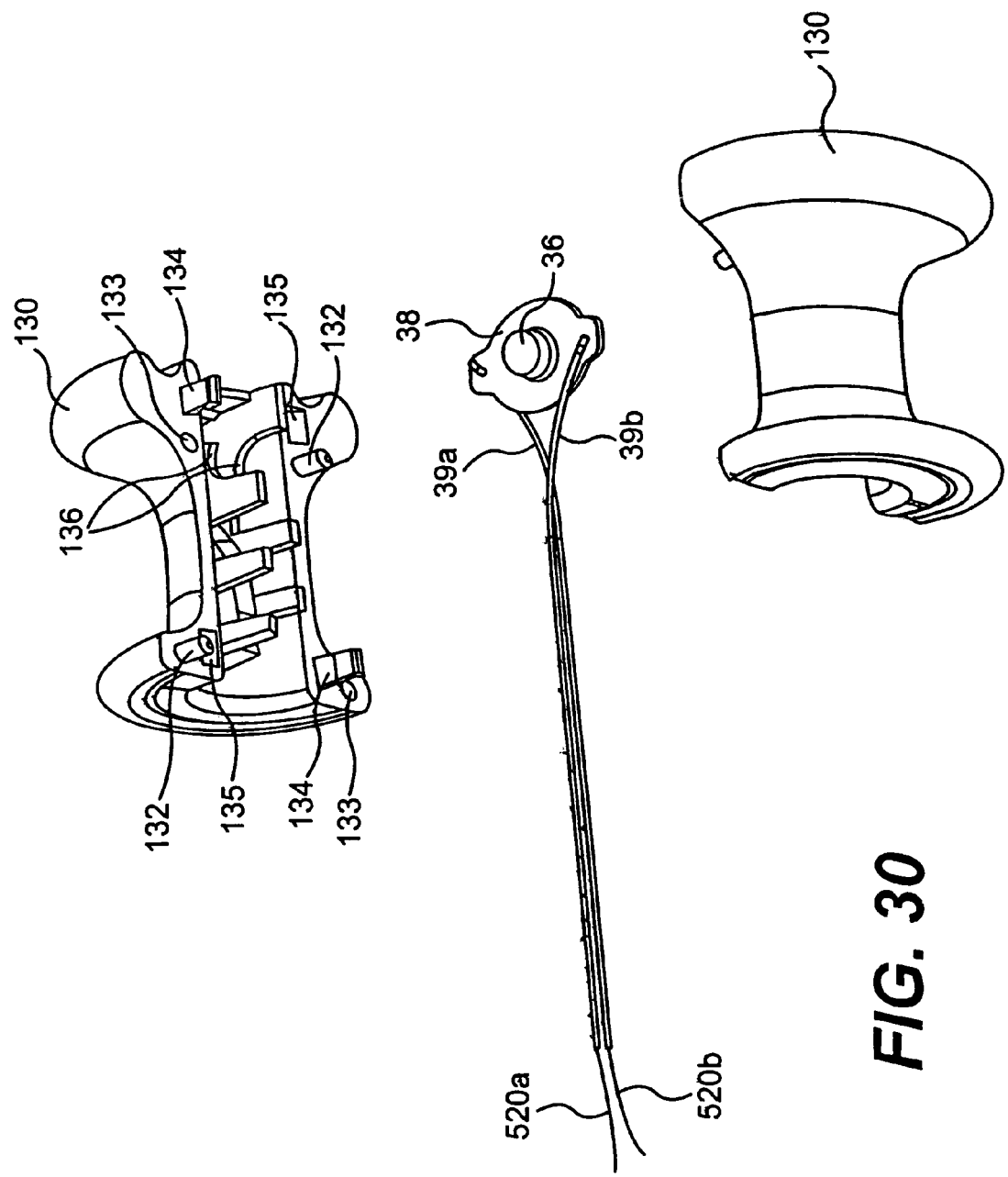
FIG. 30 is a partially exploded perspective view of a portion of the biopsy instrument of FIG. 24.

Actuation spool 34 slidably mounts on shaft 30. Actuation spool 34 includes a central hole through which shaft 30 extends. This permits spool 34 to slide back and forth along the length of shaft 30. As shown in FIG. 29, actuation spool 34 may be assembled from two hermaphroditic spool halves 130. As best shown in FIG. 30, each spool half 130 has guide posts 132 for mating with holes 133, and tangs 134 for mating with slots 135.

Figure 31A:
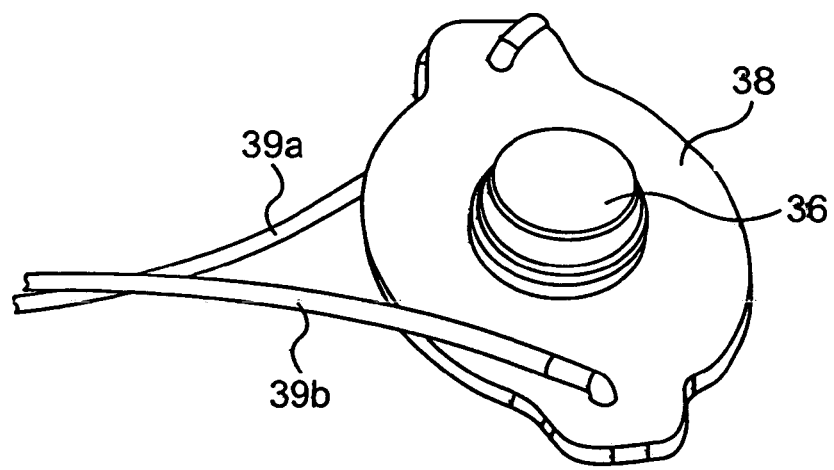
FIG. 31*a* is a perspective view of a portion of the biopsy instrument of FIG. 24.
Figure 31B:
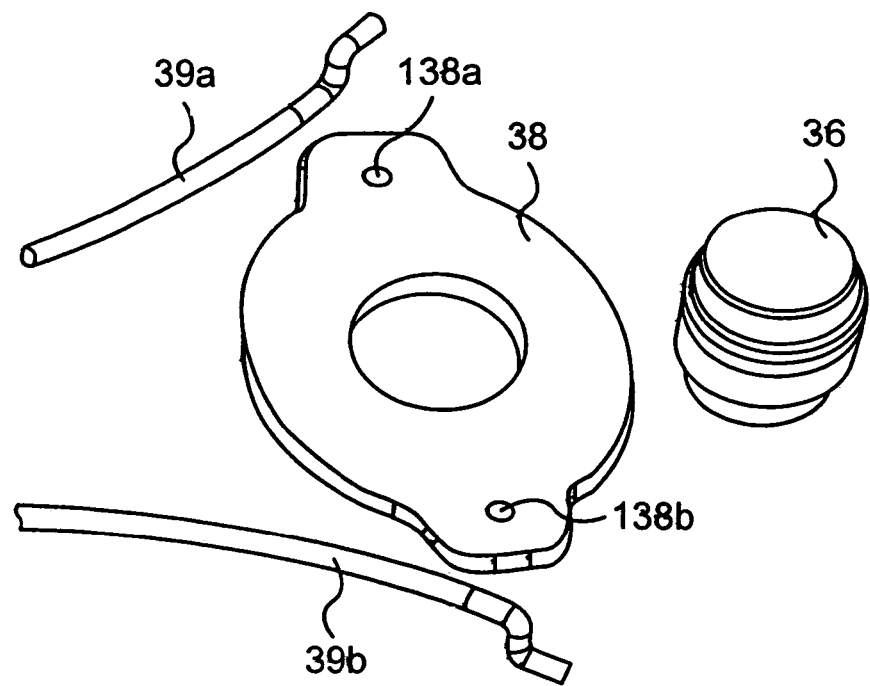
FIG. 31b is an exploded perspective view of a portion of the biopsy instrument of FIG. 24.

Pull wires 520a, 520b extend from movable jaw 590 of distal assembly 522 through control conduits 570a, 570b of flexible member 614, through nose member 37 and body portion 35 of proximal actuation handle 612, and longitudinally within slot 32 to actuation spool 34. In a preferred configuration and as shown in FIGS. 30-31b, pull wires 520a, 520b are coupled to actuation spool 34 via swash plate 38 and swash plate axle 36. Swash plate 38 freely pivots about axle 36 to accommodate uneven loading of pull wires 520a, 520b caused by bending of flexible member 612 that occurs as the biopsy instrument is positioned at the surgical site. The proximal ends of pull wires 520a, 520b are inserted through hypotubes 39a, 39b, respectively. Hypotubes 39a, 39b are provided to prevent pull wires 520a, 520b from buckling or kinking along their unsupported length within slot 32 when actuation spool 34 is moved in a distal direction. Typically, hypotubes 39a, 39b are formed from tubing similar to that used to manufacture hypodermic needles, but any tubing with sufficient anti-buckling capabilities may be used. The proximal ends of hypotubes 39a, 39b, with pull wires 520a, 520b inside, are inserted through holes 138a, 138b in swash plate 38 and bent substantially flat against swash plate 38. Pull wires 520a, 520b are thereby securely retained within hypotubes 39a, 39b and hypotubes 39a, 39b are securely retained to swash plate 38 without the necessity of additional parts. Holes 138a, 138b are diametrically opposed. Each spool half 130 has a seat 136 for swash plate axle 36, whereby swash plate 38 is capable of rotating around axle 36 relative to actuation spool 34.

Alternatively, actuation spool 34 may be provided with a transverse bar (not shown) and pull wires 520a, 520b may be connected to this bar. The bar extends transversely through slot 32 and is coupled to the wall of the central hole of actuation spool 34.

It is to be understood that actuation devices, other than a spool on a shaft, that are known to one skilled in the art may be used in connection with biopsy instruments of the present invention and any of the embodiments described herein. For example, as alternatives, the actuator may be embodied as a three-ring shaft/cylinder combination, a pistol grip handle/lever, or any other structure which permits a surgeon to move pull wires 520a, 520b.

It will be appreciated that movement of actuation spool 34 relative to shaft 30 results in movement of pull wires 520a, 520b relative to flexible member 614 and consequently moves movable jaw 590 relative to stationary jaw 588 such that the jaws open (FIG. 25) and close (FIG. 26). Referring to FIG. 26, when movable and stationary jaws 590, 588 are in a closed position, a substantially fluidtight passageway is formed therebetween.

Movable jaw 590 is coupled over irrigation conduits 572a, 572b via jaw mount 584 and irrigation conduit mounting stubs 605a, 605b. Stationary jaw 588 is coupled to aspiration conduit 574 via jaw mount 584 and aspiration conduit mounting stub 604. Thus, when movable and stationary jaws 590, 588 are in a closed position, wherein a substantially fluidtight passageway is formed therebetween, a substantially fluidtight coupling of irrigation conduits 572a, 572b to aspiration conduit 574 is achieved. Irrigation fluid flowing in a distal direction through irrigation conduits 572a, 572b may enter and flow through the passageway formed when movable and stationary jaws 590, 588 are in a closed position. This irrigation fluid may then exit from this passageway and flow in a proximal direction through aspiration conduit 574.

In accordance with the embodiment of FIG. 24, the proximal actuation handle 612 includes a nose portion coupled to the proximal end of the elongate flexible member. As embodied herein and as illustrated in FIG. 28, proximal actuation handle 612 includes body portion 35 and nose portion 37. Proximal end 615 of flexible member 614 is secured to nose portion 37 of proximal actuation handle 612 by any suitable means of connection. For example, an adhesive bonding agent could be used to secure flexible member 614 to nose portion 37. A molded strain relief 137 could be used to avoid overstraining flexible member 614 and pull wires 520a, 520b at the attachment of flexible member 614 to nose portion 37.

An irrigation passageway 620 and an aspiration passageway 622 extend through body portion 35 and nose portion 37. Irrigation conduit 572 is coupled in a substantially fluidtight fashion to irrigation passageway 620, and aspiration conduit 574 is coupled in a substantially fluidtight fashion to aspiration passageway 622.

In accordance with the embodiment of FIG. 24, the proximal actuation handle 612 includes an irrigation port to provide means for flow-connecting a fluid source to the biopsy instrument. As best shown in FIG. 28, body portion 35 includes irrigation port 624. Irrigation port 624 is in fluid connection with irrigation passageway 620. In a preferred embodiment, irrigation port 624 is provided with a Luer lock fitting. The disclosed configuration allows a surgeon to quickly and easily connect and disconnect various fluid sources (not shown) to provide fluid to distal end 13 of biopsy instrument 610.

Similarly, proximal actuation handle 612 includes an aspiration port to provide means for flow-connecting a vacuum source to the biopsy instrument. As best shown in FIG. 28, body portion 35 includes aspiration port 626. Aspiration port 626 is in fluid connection with aspiration passageway 622. In a preferred embodiment, aspiration port 626 is also provided with a Luer lock fitting. Thus a surgeon may quickly and easily connect and disconnect various vacuum devices (not shown) to biopsy instrument 610.

Figure 32:
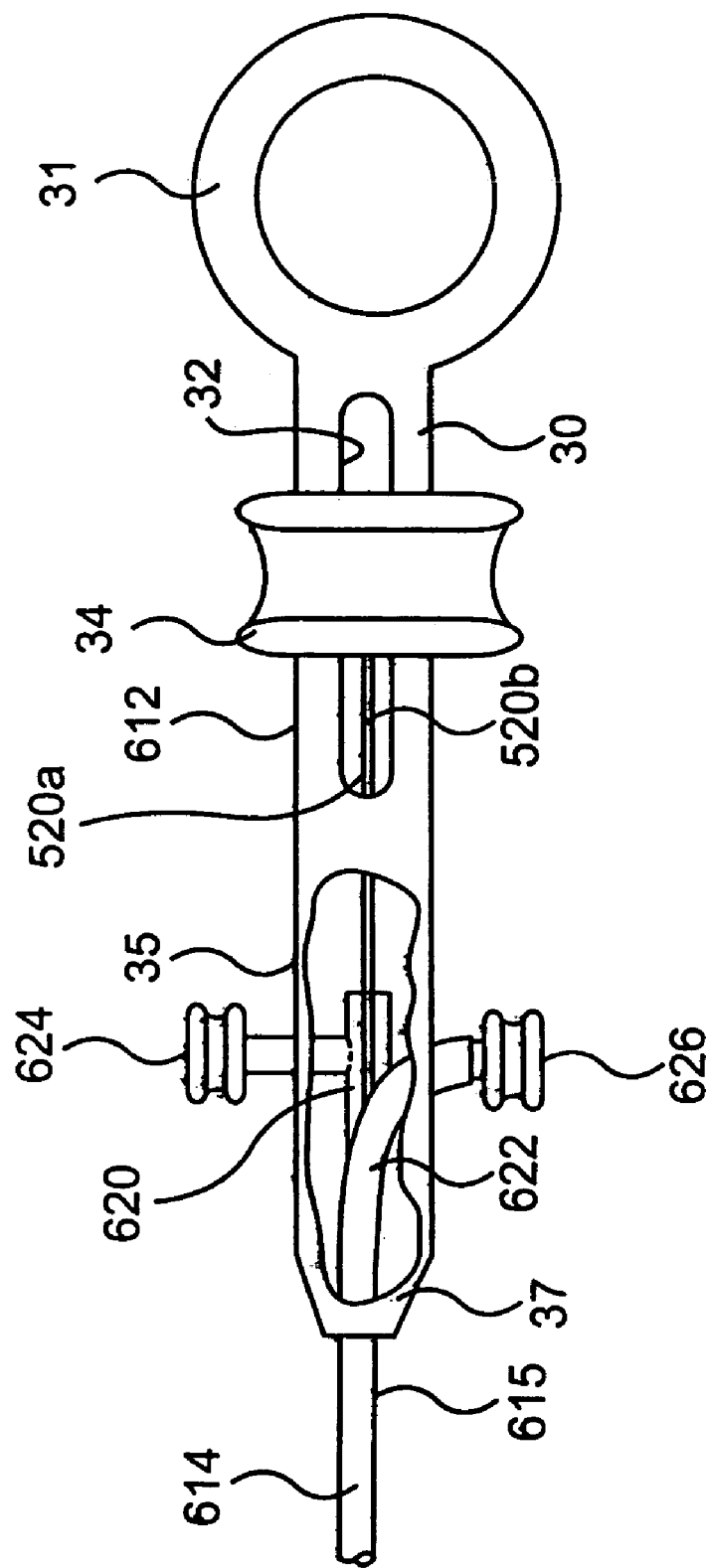
FIG. 32 is a partial cut-away side view of another aspect of a portion of the biopsy instrument of FIG. 24.

In an alternative configuration as shown in FIG. 32, irrigation passageway 620 could extend from the front end of nose portion 37 to irrigation port 624 located on a first side of body portion 35. Similarly, aspiration passageway 622 could extend from the front end of nose portion 37 to aspiration port 626 located on a second side of body portion 35. Irrigation port 624 and aspiration port 626 may be provided with Luer locks. It is to be understood that other positions of irrigation and aspiration ports 624, 626 with respect to the handle 612 are within the scope of the invention.

When not in fluid connection with a fluid or a vacuum source, irrigation port 624 and aspiration port 626, respectively, may be provided with a removable cap (not shown). As is well known to persons skilled in the art, a Luer lock is a standard fitting for fluid connection of medical devices. However, it should be understood that other standard and non-standard fluid connection fittings may also be used without departing from the scope or spirit of the invention.

The fluid source typically contains an irrigation fluid, such as saline solution. A pump (not shown) may be in fluid connection with irrigation port 624 to provide a constant and/or intermittent flow of irrigation fluid from a fluid source to distal end 13 of biopsy instrument 610. Alternatively, a fluid filled syringe (not shown) may be directly or indirectly in fluid connection with irrigation port 624, wherein depressing the plunger of the syringe causes fluid to flow to distal end 13 via irrigation conduit 572. In another alternative, a fluid source may be suspended at an elevation above the patient being operated upon and in fluid connection with irrigation port 624 via a fluid source conduit (not shown) so that gravity causes fluid to flow to distal end 13.

The vacuum source may include a sample collector in fluid connection with a vacuum pump or other suction retrieval devices. Alternatively, the vacuum source may include a waste collection device in fluid connection with a vacuum pump.

Operation of the embodiment of a biopsy instrument shown in FIGS. 24-29 will now be described. When a surgeon desires to take a tissue sample from within a patient's body without invasive surgery, the surgeon inserts distal end 13 of biopsy instrument 610 into an orifice of a patient under treatment. While retaining control of proximal actuation handle 612 at proximal end 11, the surgeon guides distal assembly 522 through the patient's body to a position adjacent a tissue to be sampled. In a preferred embodiment, the surgeon uses endoscopic technology to ensure proper positioning of distal assembly 522. The surgeon inserts distal end 13 of biopsy instrument 610 into an endoscope already inserted and properly located within a patient's body. Distal assembly 522 is threaded through the endoscope until the surgical site is reached.

The tissue to be sampled is then sited within opened movable jaw 590. In order to facilitate siting the tissue within the open distal assembly, the surgeon may actuate the vacuum effect, thereby drawing the tissue into the area between the jaws. Once jaw 590 is properly positioned, the surgeon slides spool 34 along shaft 30 in the proximal direction. This, in turn, axially displaces pull wires 520a, 520b in the proximal direction causing movable jaw 590 to pivot about pivot pin 594. Distal assembly 522 is thereby closed as illustrated in FIG. 26, and the tissue sample is separated from the surrounding tissue when sharp cutting edge 598 of movable jaw 590 comes into contact with blunt edge 592 of stationary jaw 588. The severed tissue sample is enclosed within the fluid passageway formed by cup-like body 595 of movable jaw 590 and concave cavity 601 of stationary jaw 588.

The surgeon then proceeds to initiate flow from a fluid source through irrigation port 624, irrigation passageway 620, and irrigation conduit 572. Fluid flows to distal end 617 of irrigation conduit 572 to flush the surgical region. The surgeon also initiates a vacuum effect in aspiration port 626, aspiration passageway 622, and aspiration conduit 574. This causes fluid flowing through distal end 617 of irrigation conduit 572 to return through aspiration conduit 574. The severed tissue sample will be swept into the flow, and will travel through aspiration conduit 574 from distal end 617 to proximal end 615 under the combined action of the fluid flow and the vacuum effect. Upon exiting aspiration port 626, the severed tissue sample may be collected by a sample collector (not shown) or simply disposed of in a waste collection device (not shown).

As a first alternative method of retrieving a severed tissue sample, the vacuum effect need not be initiated by the surgeon. Without the vacuum effect, the severed tissue sample may be flushed through aspiration conduit 574 under the action of the fluid flow alone. As a second alternative, no fluid need be supplied to distal end 617. Without irrigation fluid, the severed tissue sample is aspirated through aspiration conduit 574 under the action of the vacuum effect alone. A third alternative method of retrieving a tissue sample includes using irrigation fluid supplied by the endoscope, or other fluid available at the surgical site, to aid in the retrieval of the tissue sample through aspiration conduit 574 under the action of the vacuum effect.

After retrieval of a tissue sample, the surgeon may then reposition distal end 13 of biopsy instrument 610 proximate to the next tissue sample to be collected, and proceed to obtain and recover a this other tissue sample by repeating the above process. In this manner, the surgeon may recover multiple tissue samples without the necessity of removing distal end 13 of biopsy instrument 610 from the body of the patient.

Figure 33:
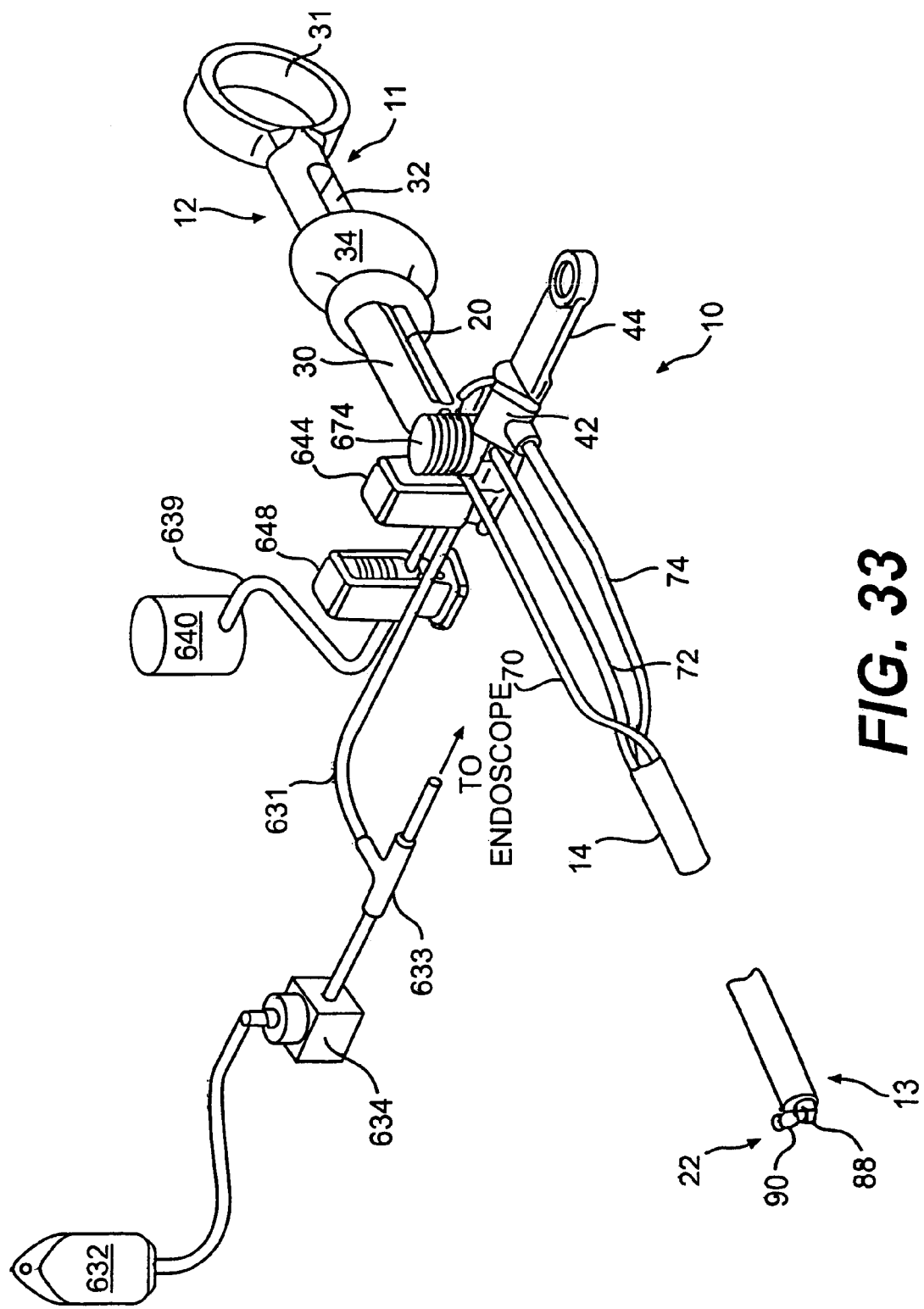
FIG. 33 is a perspective view of an endoscopic biopsy forceps instrument in accordance with still another embodiment of the present invention.

A further embodiment of a biopsy instrument according to the present invention is shown in FIG. 33. This embodiment generally relates to a biopsy instrument having irrigation and aspiration capabilities and including fluid pressure increasing capabilities. The fluid pressure increasing capabilities discussed below and shown in FIGS. 33-37 may be incorporated into any of the several embodiments of a biopsy instrument having irrigation capabilities described herein.

A biopsy instrument according to the embodiment of FIG. 33 generally relates to a method and apparatus for increasing the pressure of fluid flowing through a biopsy instrument. The inventive method and apparatus are shown in connection with an endoscopic biopsy forceps device that retrieves multiple tissue samples from a patient without withdrawal of the device from the patient. The biopsy forceps device provides irrigation at the distal end and aspiration of the samples to the proximal end through fluid pressure and suction. The present embodiment provides a method and apparatus to increase fluid pressure to more effectively retrieve the tissue samples.

A surgical biopsy instrument according to the embodiment shown in FIG. 33 generally includes a proximal actuation handle, a distal assembly, and an elongate flexible member connecting the proximal actuation handle to the distal assembly. A fluid pressure device is in fluid connection with the flexible member to selectively increase the pressure of fluid being supplied to the distal end. These general portions of the biopsy instrument will now be more specifically described. The operation of the biopsy instrument will be described thereafter.

In accordance with the present invention, there is provided a biopsy instrument having a proximal end and a distal end. As illustrated in FIG. 33, biopsy instrument 10 includes proximal end 11 and distal end 13. As with previous embodiments, during a surgical procedure, proximal end 11 remains external to a patient's body and under the direct physical control of the surgeon. Distal end 13 is inserted into a passageway or cavity of the patient's body and is positioned proximate to the remote internal operation site. In the preferred embodiment, distal end 13 of biopsy instrument 10 is inserted into and threaded through an endoscope (not shown) which has previously been inserted in the patient's body and positioned proximate to the operation site.

Figure 34:
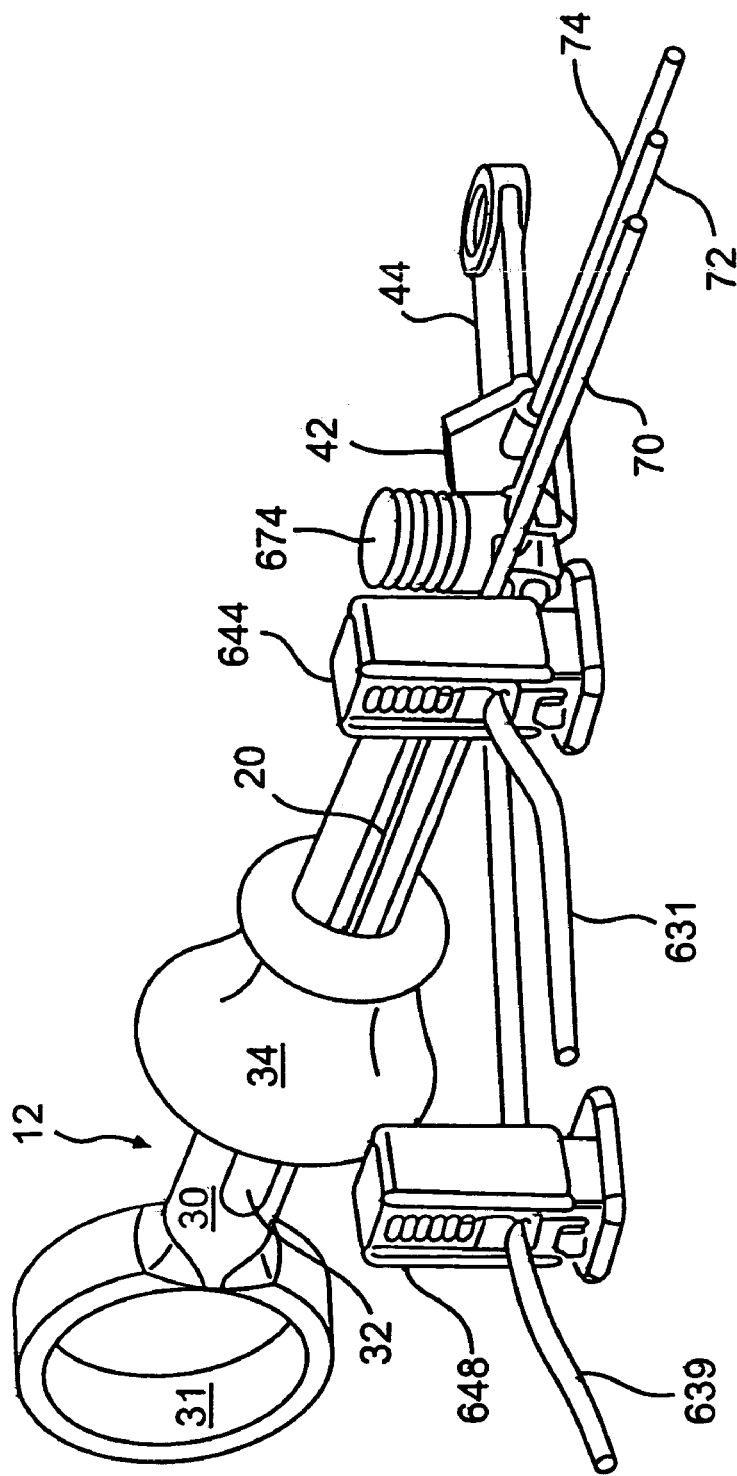
FIG. 34 is a rotated perspective view of a portion of the biopsy instrument of FIG. 33.

In accordance with the embodiment shown in FIGS. 33 and 34, the biopsy instrument includes proximal actuation handle 12 located at proximal end 11 of biopsy instrument 10. Proximal actuation handle 12 includes an elongate shaft 30 having a manipulation thumb ring 31 fixed to the end thereof. Manipulation thumb ring 31 enables a surgeon to better grip and control biopsy instrument 10.

Proximal actuation handle 12 also includes a manipulable actuator spool 34 connected to a distal assembly 22 via a pull wire 20. Distal assembly 22 and its operation will be described further herein. As illustrated in FIGS. 33 and 34, actuator spool 34 includes a hole through which shaft 30 extends. This permits spool 34 to slide back and forth along the length of shaft 30 to manipulate distal assembly 22. Shaft 30 includes an axial control slot 32 through which pull wire 20 extends. As with other embodiments described, it is to be understood that various other suitable actuation devices known to one skilled in the art may be used in connection with the present invention. For example, as alternatives, the actuation device may be embodied as a three-ring cylinder/shaft device, a pistol grip handle/lever or any other structure which permits a surgeon to move the pull wire.

The biopsy instrument according to the embodiment shown in FIG. 33 includes an elongate flexible member connected to and extending from the proximal actuation handle. The flexible member includes an irrigation conduit for fluid connection with a fluid source for supplying a fluid to the distal end of the biopsy instrument. As embodied herein and as illustrated in FIG. 33, elongate flexible member 14 is connected to and extends from an end of proximal actuation handle 12 opposite manipulation thumb ring 31. Flexible member 14 includes irrigation conduit 72 for fluid connection with fluid source 632 to distal end 13 of biopsy instrument 10. A fluid source conduit 631 flow-connects fluid source 632 to the proximal end of irrigation conduit 72. Fluid source 632 typically consists of an irrigation fluid, such as saline solution. In a preferred embodiment, fluid source 632 and fluid source conduit 631 are also in fluid connection with the endoscope (not shown) through which biopsy instrument 10 is threaded. In this preferred embodiment, tee-connector 633 is provided in fluid source conduit 631 for flow-connecting fluid source 632 to both biopsy instrument 10 and the endoscope. Thus, a single fluid source 632 may provide irrigation fluid to the distal end of the endoscope to remove debris (blood, tissue, etc.) from the lens of the endoscope and to distal end 13 of biopsy instrument 10.

A pump 634 may be provided in fluid source conduit 631 to provide a constant and/or intermittent flow of irrigation fluid from source 632 to distal end 13. Alternatively, fluid source 632 may be pressurized, or fluid may flow through fluid source conduit 631 via gravity, by suspending fluid source 632 at an elevation above the patient being operated upon.

In the embodiment shown in FIGS. 33 and 34, fluid flow through irrigation conduit 72 is controlled by a valve 644 located on fluid source conduit 631 adjacent to proximal actuation handle 12. Preferably, valve 644 is a spring-biased pinch valve, such as the one previously described.

Flexible member 14 also includes a control conduit 70. Control conduit 70 is connected to and extends from the end of proximal actuation handle 12 opposite manipulation thumb ring 31. Conduit 70 provides a channel through which pull wire 20 extends.

Flexible member 14 further includes an aspiration conduit 74. As described above and as shown in FIGS. 10 and 11, aspiration conduit 74 cooperates with and is in fluid communication with irrigation conduit 72 at distal end 13 of biopsy instrument 10. Thus, fluid flowing distally through irrigation conduit 72 may return to the proximal end through aspiration conduit 74.

In a preferred embodiment, aspiration conduit 74 is in fluid connection, via a fluid vacuum conduit 639, with a vacuum 11 reservoir 640 towards the proximal end of aspiration conduit 74. Vacuum reservoir 640, under vacuum pressure, facilitates the flow of fluid or other matter through aspiration conduit 74 from distal end 13 towards proximal end 11.

As illustrated in FIGS. 33 and 34, biopsy instrument 10 also includes a sample chamber 42 and a sample catch member 44 in-line with aspiration conduit 74. Preferably, sample chamber 42 and sample catch member 44 are connected or provided proximate to proximal actuation handle 12 for ease of access. Sample chamber 42 acts as a filter to trap material flowing through aspiration conduit 74. Material, such as biopsy samples, trapped by sample chamber 42 assembly may then be retrieved by the surgeon.

As illustrated in FIGS. 33 and 34, an aspiration valve 648 may be provided on fluid vacuum conduit 639, adjacent proximal actuation handle 12, to permit a surgeon to start and stop a vacuum effect in aspiration conduit 74.

The biopsy instrument according to the present invention further includes a distal assembly for use in a surgical operation. The distal assembly is located on the distal end of the flexible member opposite the proximal actuation handle. The distal end assembly used in connection with the embodiment of FIGS. 33 and 34 may be of any of the types described herein. For example, as in the embodiment shown in FIGS. 10 and 11, distal assembly 22 includes movable jaw 90 located at distal end 13 of biopsy instrument 10, on the end portion of flexible member 14 opposite proximal actuation handle 12. Movable jaw 90 includes a cup-like body 95 and a sharp cutting edge 98. Jaw 90 pivots about pivot pin 94 to urge cutting edge 98 against a stationary jaw 88 opposing movable jaw 90. Stationary jaw 88 includes a concave cavity 101 and a blunt edge 92.

Movable jaw 90 is connected to a distal end of pull wire 20 opposite to the proximal end connected to actuator spool 34. As has been described, this configuration allows a surgeon to cut a biopsy sample by manipulating actuator spool 34.

Again, it should be understood that while the previously described manipulable distal assembly 22 may be used with a preferred embodiment of the invention, other manipulable and non-manipulable end effectors may also be used without departing from the scope or spirit of the invention. For example, alternative end effector assemblies include dual actuating jaws, as described below.

The biopsy instrument according to the embodiment illustrated in FIG. 33 further includes means for permitting a surgeon to selectively increase fluid pressure in the irrigation conduit, thereby causing a surge in fluid flow through the distal end of the biopsy instrument. As embodied herein, and as illustrated in FIGS. 33 and 34, means for permitting a surgeon to selectively increase fluid pressure in irrigation conduit 72 may include a fluid pressure device located in-line with the irrigation conduit 72. Activation of the fluid pressure device permits the surgeon to selectively increase fluid pressure in irrigation conduit 72, thereby causing a surge in fluid flow through distal end 13 of biopsy instrument 10.

In the embodiment illustrated in FIG. 33, fluid source 632 provides irrigation fluid to both biopsy instrument 10 and the endoscope. Alternatively, the endoscope power unit (not shown), which supplies water, light and air to the endoscope, also supplies water as the irrigation fluid to biopsy instrument 10. It is expected that typical irrigation fluid pressures at proximal end 11 of biopsy instrument 10 range from 3-5 psia, and that activation of the fluid pressure device may increase the irrigation fluid pressure to 20 psia.

Figure 35:
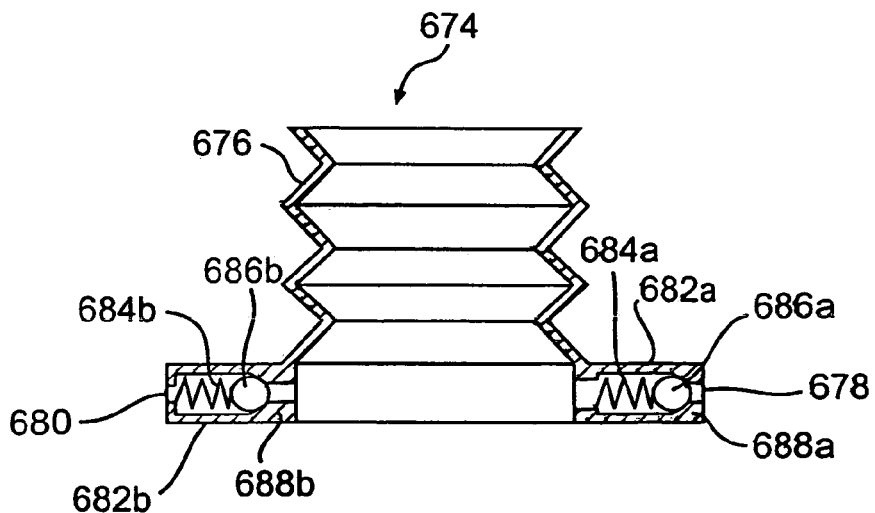
FIG. 35 is a cross-sectional view of the flexible bellows fluid pressure device illustrated in FIG. 33.
Figure 36:
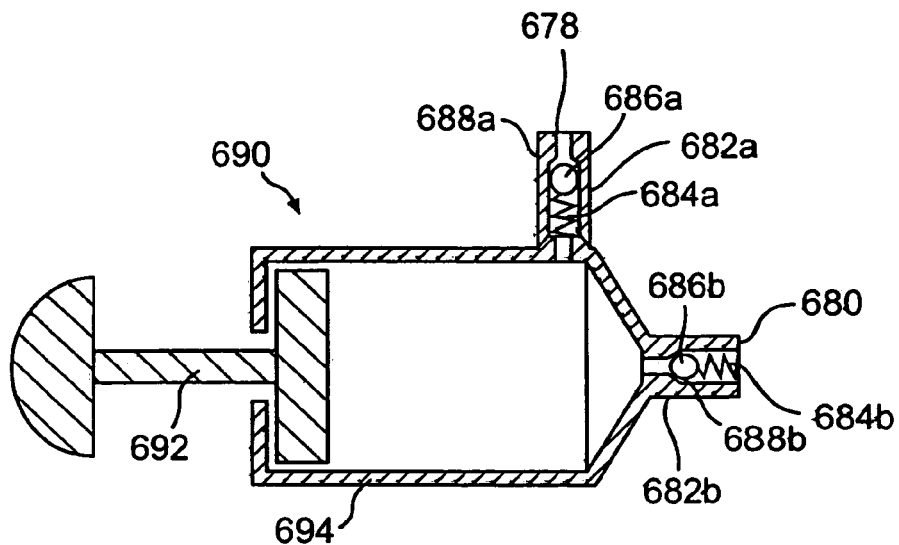
FIG. 36 is a cross-sectional view of a piston-and-cylinder fluid pressure device for use in connection with the endoscopic biopsy forceps instrument of FIG. 33.
Figure 37:
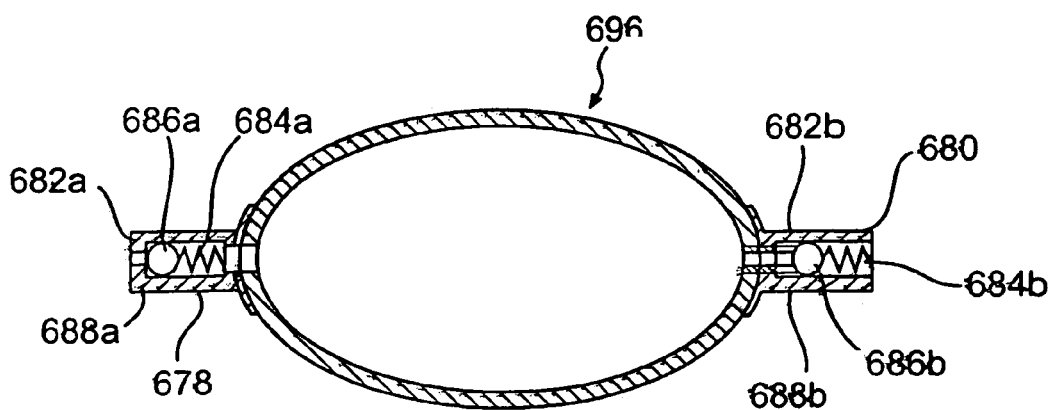
FIG. 37 is a cross-sectional view of a flexible membrane fluid pressure device for use in connection with the endoscopic biopsy forceps instrument of FIG. 33.

As illustrated in FIGS. 35-37, the fluid pressure device may include a contractible fluid accumulating chamber, which can be selectively contracted to cause a pressure surge through irrigation conduit. In a first embodiment of a fluid pressure device shown in FIGS. 33-35, a flexible bellows 674 defines a fluid accumulating chamber therein. A pleated collapsible wall member 676 imparts the contractibility attribute to bellows 674. Collapsible wall member 676 could be made of metal, plastic, or other suitable waterproof material. As illustrated in FIG. 35, the flexible bellows 674 further includes a fluid inlet port 678 and a fluid outlet port 680. Fluid inlet port 678 is in fluid connection with fluid source 632, thereby permitting the accumulating chamber to fill with fluid. Fluid outlet port 680 is in fluid connection with the accumulating chamber and with irrigation conduit 72.

A suitable valve is provided proximate inlet port 678 to permit fluid to flow into the fluid accumulating chamber from fluid source 632 and prohibit fluid from returning thereto. The flexible bellows 674 of FIG. 35 includes a check valve 682a, including a spring 684a, a spring-biased ball 686a, and a valve seat 688a. Check valve 682a is upstream of inlet port 678. In a closed position, spring 684a urges ball 686a against seat 688a. Fluid flowing into fluid inlet port 678 from fluid source 632 forces spring-biased ball 686a against spring 684a. This force compresses spring 684a until ball 686a is no longer held against valve seat 688a, permitting fluid to flow past ball 686a and into the contractible fluid accumulating chamber. Fluid that would tend to flow out of fluid inlet port 678 towards fluid source 632 pushes spring-biased ball 686a against valve seat 688a to thereby block the flow. Check valve 682a therefore permits fluid from fluid source 632 to flow into the fluid accumulating chamber, while concurrently prohibiting fluid from flowing out of the fluid accumulating chamber back towards fluid source 632.

Similarly, a suitable valve is provided proximate outlet port 680 to prevent fluid from flowing out of the fluid accumulating chamber until a given fluid pressure is obtained and to prevent fluid from flowing back into the fluid accumulating chamber. The flexible bellows 674 of FIG. 35 includes a check valve 682b, including a spring 684b, a spring-biased ball 686b, and a valve seat 688b. Check valve 682b is downstream of inlet port 678. In a closed position, spring 684b urges ball 686b against seat 688b. Pressurized fluid flowing out of fluid outlet port 680 opens valve 682b by forcing spring-biased ball 686b against spring 684b. Operation of the flexible bellows 674 during an endoscopic procedure will be described further herein.

Alternative structures of the fluid pressure device, and more particularly the contractible fluid accumulating chamber, are within the scope of this invention. For example, as illustrated in FIG. 36, the contractible fluid accumulating chamber of fluid pressure device may include a piston-and-cylinder device 690 including cylinder 694 and piston 692 slidably located within cylinder 694. This structure is similar in many respects to the bellows structure previously described. Piston-and-cylinder device 690 includes fluid inlet port 678, fluid outlet port 680, and check valves 682a, 682b. In the piston-and-cylinder device, fluid accumulates in cylinder 694. Depression of piston 692 causes a pressure surge through irrigation conduit 72. It is preferable to locate the piston-and-cylinder device on or adjacent proximal actuation handle 12 for ease of use by the surgeon.

As a further alternative of the fluid pressure device, and as illustrated in FIG. 37, the contractible fluid accumulating chamber may include a flexible membrane 696. Flexible membrane 696 is preferably made of rubber, polymers, or any other suitably flexible material known in the art. Flexible membrane 696 defines a fluid accumulating chamber therein. Like the bellows and piston structures previously described, the membrane structure includes fluid inlet port 678, fluid outlet port 680, and check valves 682a, 682b. Preferably, flexible membrane 696 is formed as a squeeze ball. Deforming the squeeze ball from its undeformed configuration imparts the contractibility attribute to flexible membrane 696, causing a pressure surge through irrigation conduit 72.

It will be apparent to those skilled in the art that means for selectively increasing the fluid pressure in irrigation conduit 72 could encompass purely mechanical pressurization devices and also electro-mechanical pressurization devices. It will also be apparent to those skilled in the art that the fluid pressure devices can be situated in various other positions relative to the surgeon. For example, the fluid pressure device may be positioned on the floor proximate the surgeon's foot for foot activation. Foot activation of the fluid pressure device keeps the surgeon's hand free for other activities.

Operation of the invention will now be described with reference to FIGS. 10, 11, 33 and 35. As in previously described embodiments, when a surgeon desires to take a tissue sample from within a patient's body without invasive surgery, the surgeon inserts distal end 13 of biopsy instrument 10 into an orifice of a patient under treatment. While retaining control of proximal actuation handle 12 at proximal end 11, the surgeon guides distal assembly 22 through the patient's body to a position adjacent a tissue to be sampled. In a preferred embodiment, the surgeon uses endoscopic technology to ensure proper positioning of the distal assembly 22. The surgeon inserts distal end 13 of biopsy instrument 10 into an endoscope already inserted and properly located within a patient's body. Distal assembly 22 is threaded through the endoscope until the surgical site is reached. The tissue to be sampled is then sited within opened jaw 90, as illustrated in FIG. 10. Once jaw 90 is properly positioned, the surgeon slides spool 34 along shaft 30 in the proximal direction. This, in turn, axially displaces pull wire 20 in the proximal direction causing movable jaw 90 to pivot about pivot pin 94. Distal assembly 22 is thereby closed, and tissue sample 112 is separated from the surrounding tissue when sharp cutting edge 98 of movable jaw 90 comes into contact with blunt edge 92 of stationary jaw 88. As illustrated in FIG. 11, severed tissue sample 112 is enclosed within the fluid passageway formed by cup-like body 95 of movable jaw 90 and concave cavity 101 of stationary jaw 88.

The surgeon then proceeds to initiate flow from fluid source 632 through the fluid pressure device and through irrigation conduit 72 by depressing irrigation valve 644. In response, fluid flows into the fluid pressure device and fills the contractible fluid accumulating chamber. Once filled, fluid flows to distal end 13 of irrigation conduit 72 to flush the surgical region under relatively low pressure. At the same time, or slightly later, the surgeon may initiate a vacuum effect in aspiration conduit 74 by depressing aspiration valve 648. This causes fluid flowing through distal end 13 of irrigation conduit 72 to return through aspiration conduit 74. Tissue sample 112 will be swept in the flow, and will begin traveling through aspiration conduit 74 from distal end 13 to proximal end 11 under the combined action of the fluid flow and the vacuum effect. As an alternative, the vacuum effect need not be initiated by the surgeon. Without the vacuum effect, tissue sample 112 may be flushed through aspiration conduit 74 under the action of the fluid flow alone.

However, on occasion, tissue sample 112 may become lodged in either distal assembly 22 or in aspiration conduit 74. When this happens, the surgeon may then actuate the fluid pressure device by compressing the fluid accumulating chamber. Compressing the accumulating chamber pressurizes the fluid flowing into irrigation conduit 72, causing a surge in fluid flow through distal end 13 of biopsy instrument 10. This surge in fluid flow augments the existing flow in the biopsy instrument, thus enabling the surgeon to more effectively and reliably retrieve tissue sample 112 through aspiration conduit 74 to sample chamber 642. If necessary, the surgeon may actuate the fluid pressure device multiple times to aid in the retrieval of tissue sample 112. Similarly, the surgeon may vary the pressure of the fluid flow surge, either by actuating the fluid pressure device slowly for a mild surge or actuating the fluid pressure device quickly for a sharp surge in the fluid flow. The surgeon then recovers tissue sample 112 from sample chamber 642.

The surgeon may then reposition distal end 13 proximate to the next tissue sample 112 to be collected, and proceed to obtain and recover a second tissue sample 112 by repeating the above process. In this manner, the surgeon may recover multiple tissue samples without the necessity of removing distal end 13 of biopsy instrument 10 from the body of the patient.

Figure 38:
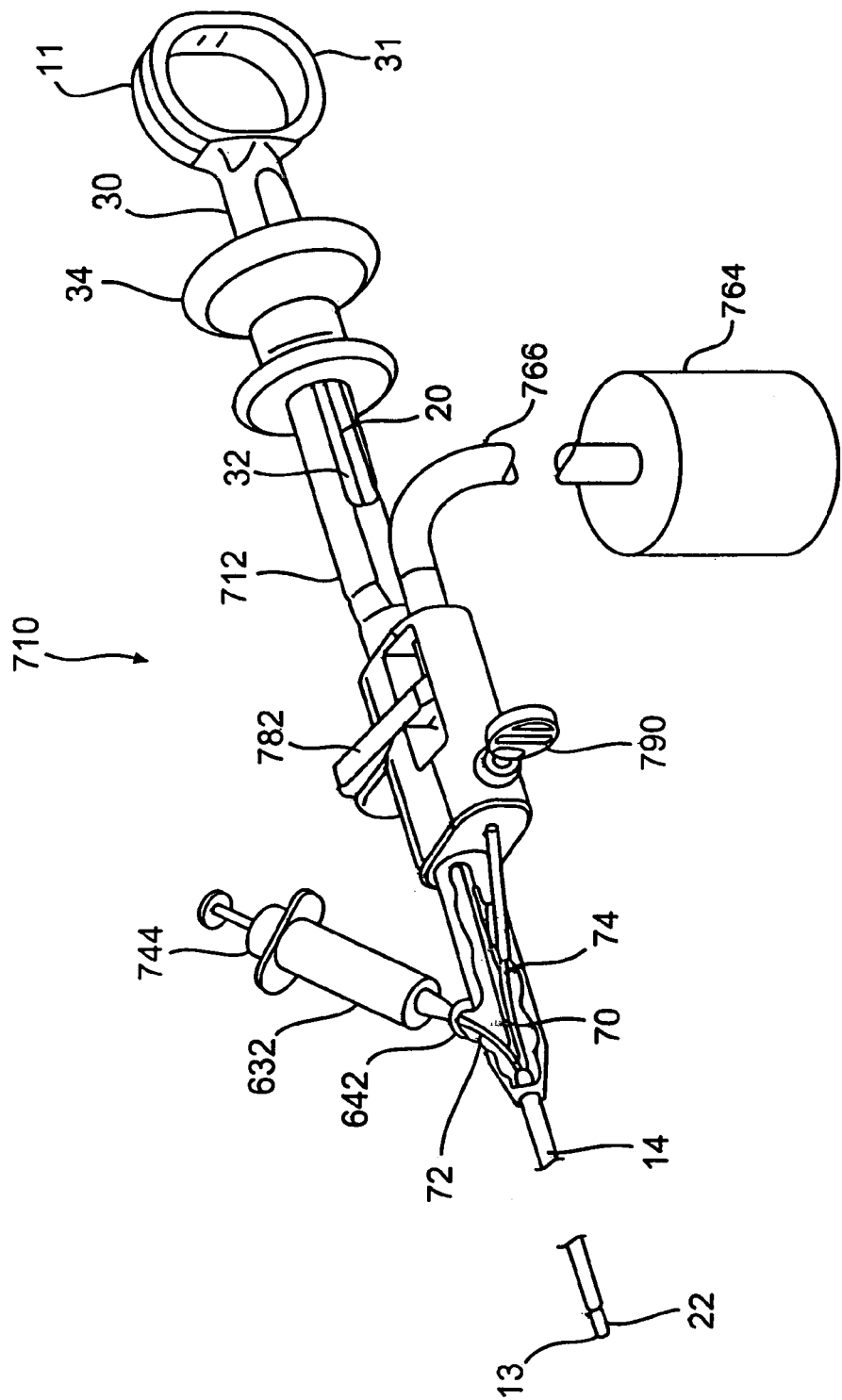
FIG. 38 is a perspective view of a biopsy instrument in accordance with a still further embodiment of the present invention.

A still further embodiment of a biopsy instrument according to the present invention is shown in FIG. 38. This embodiment generally relates to a method and an apparatus to minimize the manual handling and consequential degradation of biopsy tissue samples through the use of a biopsy instrument having irrigation and aspiration capabilities and including a removable, modular sample collector. The embodiment shown in FIG. 38 may be incorporated into any of the several embodiments of a biopsy instrument having irrigation and aspiration capabilities described herein.

A biopsy instrument according to the embodiment of FIG. 38 generally includes a distal assembly, a proximal actuation handle, and an elongate flexible member connecting the distal assembly to the proximal actuation handle. An aspiration biopsy instrument with proximal end sample collection capabilities according to the present embodiment further includes an aspiration conduit extending from the distal to the proximal end and in fluid connection with a suction passageway. The suction passageway, located within the proximal actuation handle, has an access opening for receiving a sample collector and is in fluid connection with a vacuum source. The sample collector is inserted into the suction passageway to stop and retain aspirated biopsy samples. These general portions of the biopsy instrument will now be more specifically described. The operation of the biopsy instrument will be described thereafter.

In accordance with the embodiment shown in FIG. 38, there is provided a biopsy instrument 710 having a proximal end 11 and a distal end 13. As in previously described embodiments, during a surgical procedure, proximal end 11 remains external to a patient's body and under the direct physical control of the surgeon. Distal end 13 is inserted into a passageway or cavity of the patient's body and is positioned proximate to the remote internal operation site. In the preferred embodiment, distal end 13 of biopsy instrument 710 is inserted into and threaded through an irrigation endoscope (not shown) which has previously been inserted into the patient's body and positioned proximate to the operation site.

The biopsy instrument according to the present embodiment includes a distal assembly for use in a surgical operation. As shown in FIG. 38, distal assembly 22 is located on the distal end of flexible member 14 opposite proximal actuation handle 712. Embodiments of distal assembly 22, shown in FIGS. 10-11 have been described above. Distal assembly 22 includes a movable jaw 90 and an opposing stationary jaw 88. Movable jaw 90 includes a cup-like body 95 and a sharp cutting edge 98. Movable jaw 90 pivots about pivot pin 94 to urge cutting edge 98 against the stationary jaw 88. Stationary jaw 88 includes a concave cavity 101 and a blunt edge 92.

Movable jaw 90 is connected to a distal end of pull wire 20. As shown in FIG. 38, the proximal end of pull wire 20 is connected to actuator spool 34. Actuation of actuator spool 34 moves movable jaw 90 relative to stationary jaw 88, and thereby moves the jaws from an open position to a closed position. Actuation spool 34 and the attachment of pull wire 20 to actuation spool 34, as shown in FIG. 29, has been described above. This configuration allows a surgeon to cut a biopsy sample by manipulating actuator spool 34.

The biopsy instrument according to the present embodiment also includes an elongate flexible member connected to and extending from the distal assembly. As illustrated in FIG. 38, elongate flexible member 14 is connected to distal assembly 22 and extends in a proximal direction to proximal actuation handle 712. Proximal actuation handle 712 will be described later in greater detail.

In accordance with the present embodiment, the elongate flexible member includes an aspiration conduit. As shown in FIG. 38, flexible member 14 includes an aspiration conduit 74 extending from distal end 13 toward proximal end 11. Aspiration conduit 74 provides a conduit for fluid, tissue samples, and/or other matter to pass from distal end 13 to proximal end 11. As embodied herein, and as best illustrated in FIGS. 10 and 11, at distal end 13 aspiration conduit 74 is coupled to stationary jaw 88 of distal assembly 22.

As also embodied herein and as illustrated in FIG. 38, elongate flexible member 14 may further include an irrigation conduit 72 for fluid connection with a fluid source 632 for supplying a fluid to distal end 13 of biopsy instrument 710. Flexible member 14 includes irrigation conduit 72 for flow-connecting fluid source 632 to distal end 13 of biopsy instrument 710. As best shown in FIGS. 10 and 11, at distal end 13, irrigation conduit 72 is coupled to and in fluid connection with movable jaw 90. As best shown in FIG. 38, irrigation conduit 72 is coupled to a Luer lock 642 for flow-connecting irrigation conduit 72 to fluid source 632.

Furthermore, as embodied herein, aspiration conduit 74 cooperates with and is in fluid communication with irrigation conduit 72 at distal end 13 of biopsy instrument 710. As described above and as shown in FIGS. 10-11 and 25-26, when stationary jaw 88 and movable jaw 90 of distal assembly 22 are in a closed position, a substantially fluid tight passage is formed therebetween. Because stationary jaw 88 is coupled to aspiration conduit 74 and movable jaw 90 is coupled over irrigation conduit 72, a substantially fluid tight coupling of aspiration conduit 74 and irrigation conduit 72 is achieved. Thus, fluid flowing distally through irrigation conduit 72 returns to proximal end 11 through aspiration conduit 74.

As embodied herein and as shown in FIG. 34, fluid source 632 may be a syringe 744 filled with a saline irrigation fluid, an anticoagulant, a tissue staining dye, or any other medically necessary or desirable fluid. Alternatively, a pump (not shown) may be provided in fluid connection with irrigation conduit 72 to provide a constant and/or intermittent flow of fluid from source 632 to distal end 13. Fluid source 632 may also be pressurized, or fluid may flow through irrigation conduit 72 via gravity, by suspending fluid source 632 at an elevation above the patient being operated upon. In these alternate embodiments, fluid flow through irrigation conduit 72 may be controlled by a valve (not shown) located on irrigation conduit 72 or on any other conduit flow-connecting irrigation conduit 72 to fluid source 632. The valve may be a spring-biased pinch valve as previously mentioned, although any valve known to persons skilled in the art would be sufficient.

In the embodiment shown in FIG. 38, flexible member 14 also includes control conduit 70. Control conduit 70 is connected to and extends from distal assembly 22 at distal end 13 to proximal actuation handle 712 at proximal end 11. Control conduit 70 provides a channel through which pull wire 20 extends.

In accordance with the present embodiment, the biopsy instrument 710 includes a proximal actuation handle 712. As described above and as shown in FIG. 38, proximal actuation handle 712 includes an elongate shaft 30 having a manipulation thumb ring 31 fixed to the end thereof. Manipulation thumb ring 31 enables a surgeon to better grip and control biopsy instrument 710.

Proximal actuation handle 712 includes suction passageway 762 (FIG. 39) in fluid connection with aspiration conduit 74. Suction passageway 762 is further in fluid connection with a vacuum reservoir 764 (FIG. 38) via a vacuum conduit 766. Vacuum reservoir 764, connected to a vacuum source (not shown) and under vacuum pressure, facilitates the flow of fluid, tissue samples, or other matter, through aspiration conduit 74 and suction passageway 762.

Figure 39:
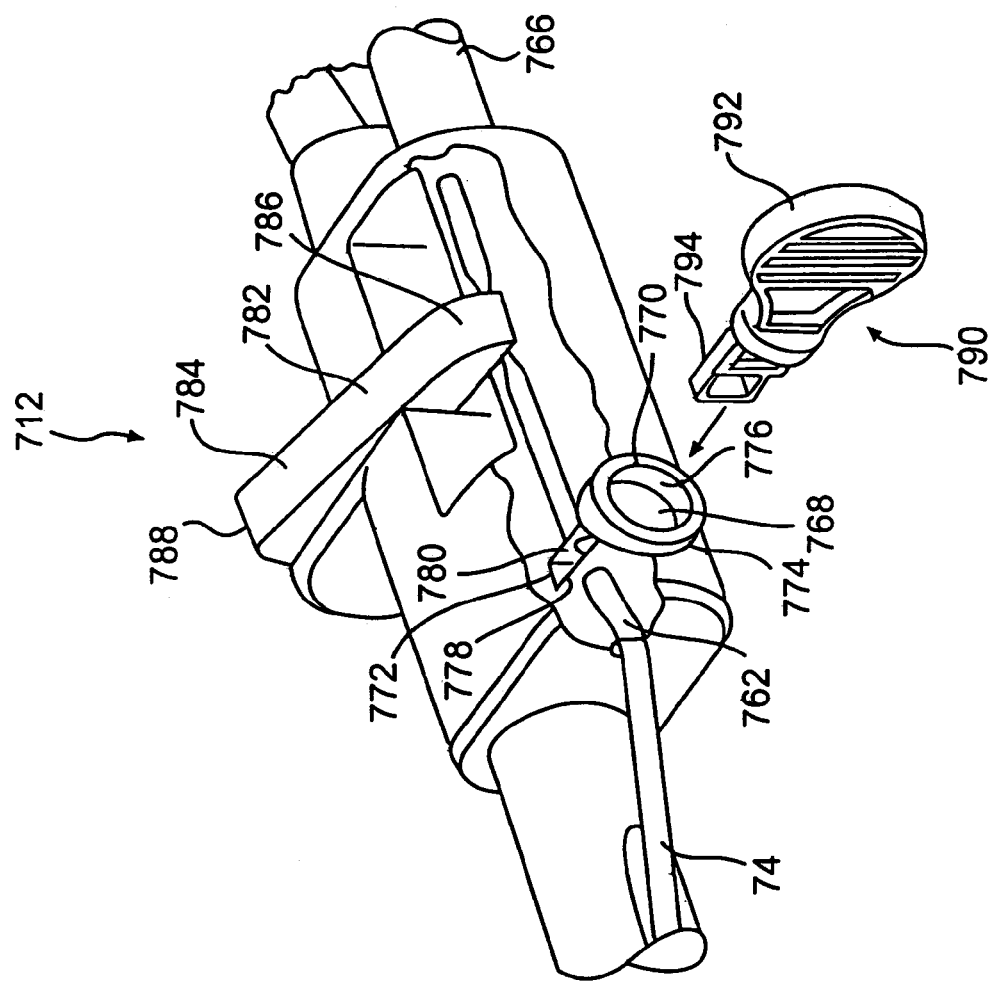
FIG. 39 is an exploded perspective view of the engagement of the sample collector with the proximal actuation handle of the biopsy instrument of FIG. 38.

As shown in FIGS. 38-39, suction passageway 762 has an access opening 768. In the preferred embodiment, access opening 768 provides a lateral access to the flow in suction passageway 762 and is composed of two portions, a securing portion 770 and a flow-passage portion 772. Securing portion 770 is configured to complement a sample collector handle 792, as will be described later in greater detail, that is partially inserted into securing portion 770 of access opening 768. In a preferred embodiment, securing portion 770 includes a circular flange 774 having a smooth, slightly tapered central bore 776. Flow-passage portion 772 is configured to complement a sample collector body 794, as will also be described later in greater detail, which is inserted into flow-passage portion 772. As embodied herein, flow-passage portion 772 includes a roughly rectangular slot 778, with an arcuate downstream wall 780, that transects the flow in suction passageway 762.

As embodied herein and best illustrated in FIG. 39, proximal actuation handle 712 includes an aspiration valve 782 provided on suction passageway 762, to permit a surgeon to start and stop a vacuum effect in suction passageway 762. Preferably, aspiration valve 782 is a spring-biased pinch valve, although any other valve also known to persons skilled in the art may be used. Aspiration valve 782 includes a pivot (not shown), a lever 784, and a spring (not shown) which causes the nose 786 of valve 782 to pinch suction passageway 762 shut. A surgeon pressing on heel 788 of lever 784 will cause the spring to compress, lever 784 to rotate around the pivot, nose 786 to release its pinch on suction passageway 762, and a vacuum effect to be established in aspiration conduit 74 and suction passageway 762.

The biopsy instrument according to the present embodiment includes a sample collector to trap and retain biopsy samples severed by operation of the distal assembly 22. As illustrated in FIG. 38, biopsy instrument 710 includes sample collector assembly 790 provided in-line with suction passageway 762. Sample collector assembly 790 acts as a filter to trap matter, such as biopsy samples, flowing through suction passageway 762. Matter trapped by sample collector assembly 790 may then be retrieved by the surgeon or nurse for subsequent pathological examination.

Figure 40A:
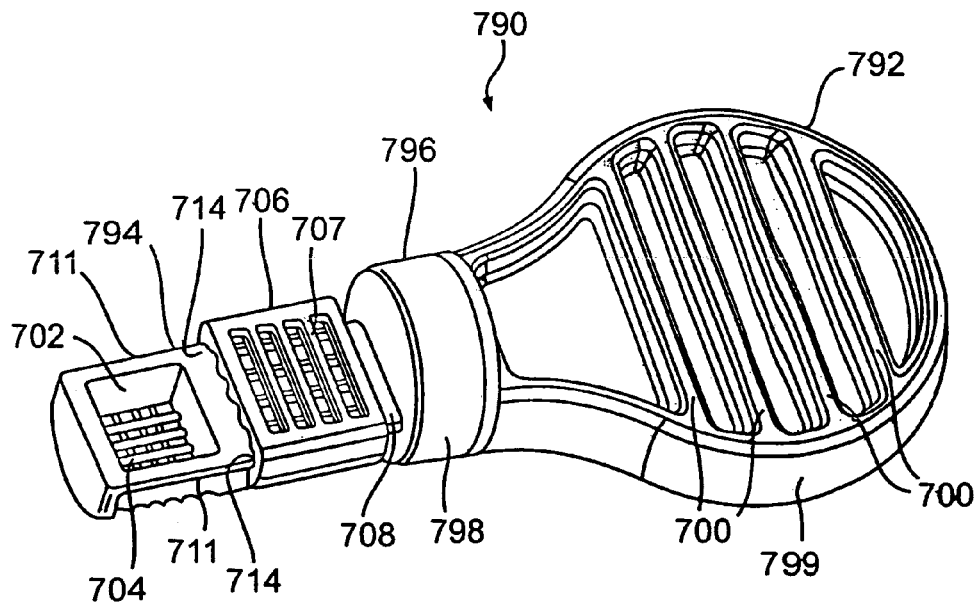
FIG. 40a is a perspective view of the sample collector of FIG. 38 with the cover in the open position.
Figure 40B:
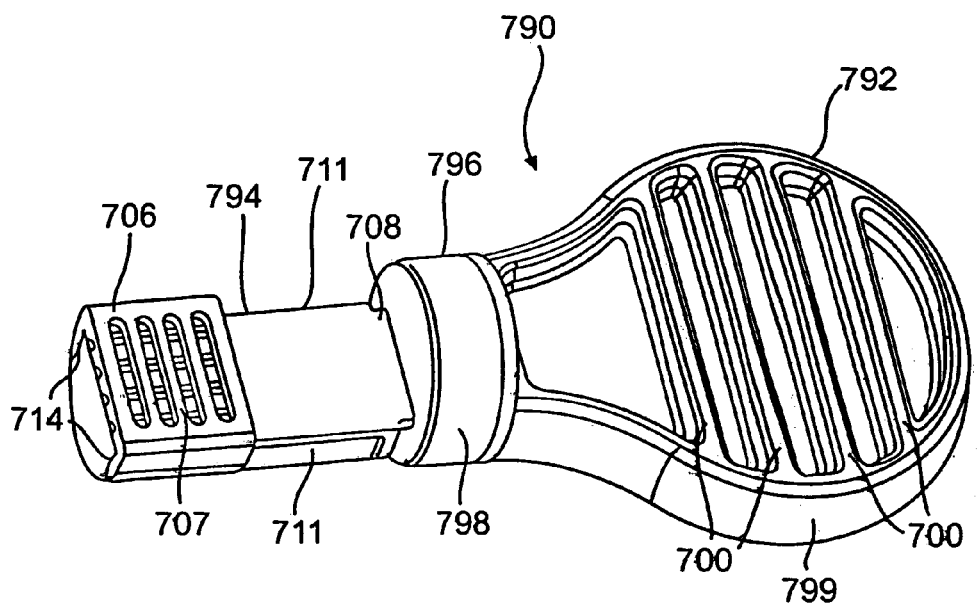
FIG. 40b is a perspective view of the sample collector of FIG. 38 with the cover in the closed position.

As illustrated in FIGS. 40a-40b, sample collector assembly 790 includes catcher handle 792 and catcher body 794. Catcher handle 792 has a securing end 796 for insertion into securing portion 770 of access opening 768. In the present embodiment, securing end 796 includes a cylindrical, slightly tapered plug 798 that complements the smooth, slightly tapered central bore of securing portion 770 to provide a seal therewith. As will be appreciated by persons skilled in the art, other access opening configurations and complementary catcher handle securing ends may be used without departing from the scope or spirit of the invention. For instance, the central bore 776 of access opening 768 might further include an o-ring seated in a circumferential slot, or access opening circular flange 774 might include external threads which couple to a mating, internally threaded collar on catcher handle 792.

Catcher handle 792 also has a gripping end 799, opposite to securing end 796, for enabling the nurse or surgeon to firmly grip and easily manipulate sample collector 790. Although the present embodiment of gripping end 799 includes a generally flat, circular tab with ribs 700 for improved gripping, it is to be understood that various other suitable gripping configurations known to persons skilled in the art may be used in connection with the present invention.

As further illustrated in FIGS. 40a-40b, catcher body 794 includes a flow opening 702, a screen 704, a cover 706, and a break-away tab 708. Catcher body 794 is insertable into and configured to complement flow-passage portion 772 of access opening 768. Catcher body 794 permits fluid flow in suction passageway 762 to continue downstream, while trapping and retaining any solid matter passing through suction passageway 762. Furthermore, as embodied herein, catcher body 794, with cover 706 in a closed position, is configured to fit into a standard pathology and histology processing cartridge.

In the present embodiment, catcher body 794 has a flow opening 702 on its upstream side and a screen 704 on its arcuate downstream side. As shown in FIG. 40a, flow opening 702 has a rectangular cross-section, although it could have any other cross-section and still be consistent with the scope of the invention. Screen 704 is located on the downstream side of catcher body 794 to trap matter, such as tissue samples, after such matter has entered flow opening 702. As shown in FIG. 40a, screen 704 may consist of a horizontal and vertical latticework. Alternatively, screen 704 may consist of an array of perforations such as holes or slots. A person skilled in the art could easily size the mesh or the holes in screen 704 to best accommodate a given flow and sample size. It is further understood that many other screen configurations are known to persons skilled in the art and may be used in connection with the present invention, including a single hole or slot, or multiple slots.

As further illustrated in FIGS. 40a-40b, catcher body 794 includes cover 706 positionable between an open position displaced from flow opening 702 of catcher body 794 (FIG. 40a) and a closed position overlaying flow opening 702 (FIG. 40b). As embodied herein, cover 706 may be slidably attached to catcher body via the interaction of a pair of flanges 711 on catcher body and a pair of channels 714 on cover 706. Alternatively, cover 706 may be pivotably attached to catcher body 794 (not shown). Cover 706 may also be completely detachable from catcher body 794, either sliding on or off the end of catcher body 794 furthest from catcher handle 792, or snapping on or off catcher body 794 by means of any of a variety of flexible snap elements (also not shown).

In the present embodiment, cover 706 includes a cover screen 707. If catcher body 794 and cover 706 are used to contain the biopsy samples during pathology processing, cover screen 707 enables the fluids involved in the pathology process to easily and completely gain access to the sample. Alternatively, cover 706 may be a solid plate.

Figure 41:
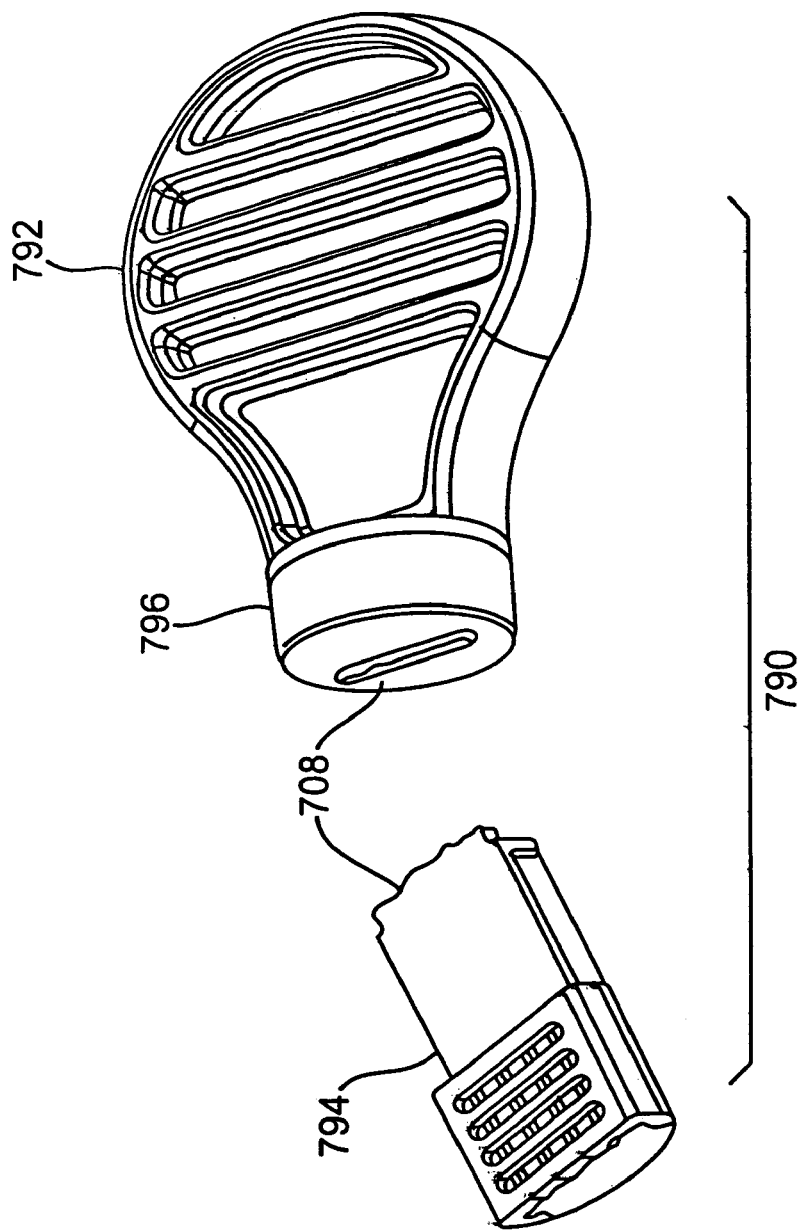
FIG. 41 is a perspective view of the sample collector of FIG. 38 with the catcher body detached from the catcher handle.

In accordance with the present invention and as illustrated in FIG. 40*b*, catcher body 794 is attached to securing end 96 of catcher handle 792 by means of break-away tab 708. As embodied herein, break-away tab 708 includes a short rectangular plate attached at one end to securing end 796 and at an opposite end to catcher body 794. As shown in FIG. 41, cleaving break-away tab 708, typically with a snapping motion, permits catcher body 794 to be detached from catcher handle 792. Sample collector 790 snaps apart at break-away tab 708 because the cross-sectional moment of inertia of tab 708 is less than the cross-sectional moment of inertia of securing end 796 or of catcher body 794. Similarly, catcher body 794 may be twisted off from catcher handle 792 if the rotational moment of inertia of break-away tab 708 is less than the rotational moment of inertia of body 794 and of handle 792.

Sample collector 790 is preferably made of plastic that is chemically inert to the chemicals used in pathology processing, specifically nylon, although other plastics such as polypropylene or polyethylene, or even a suitable glass or metal, may be used. A preferred method of manufacturing sample collector 790 is by injection-molding.

Figure 42B:
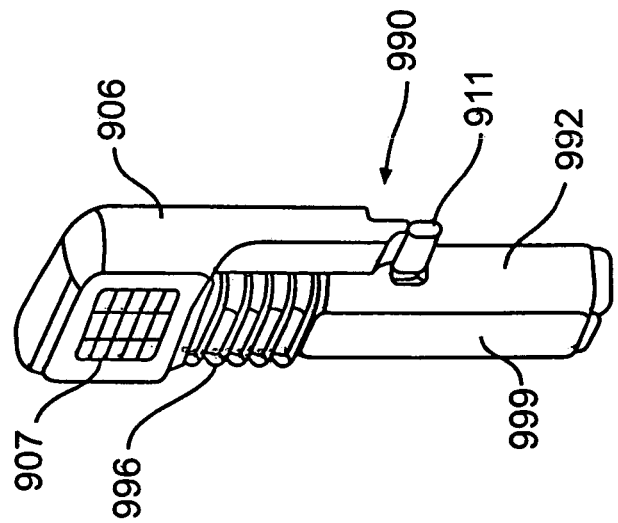
FIG. 42b is a perspective view of the sample collector of FIG. 42a with the cover in the closed position.
Figure 42A:
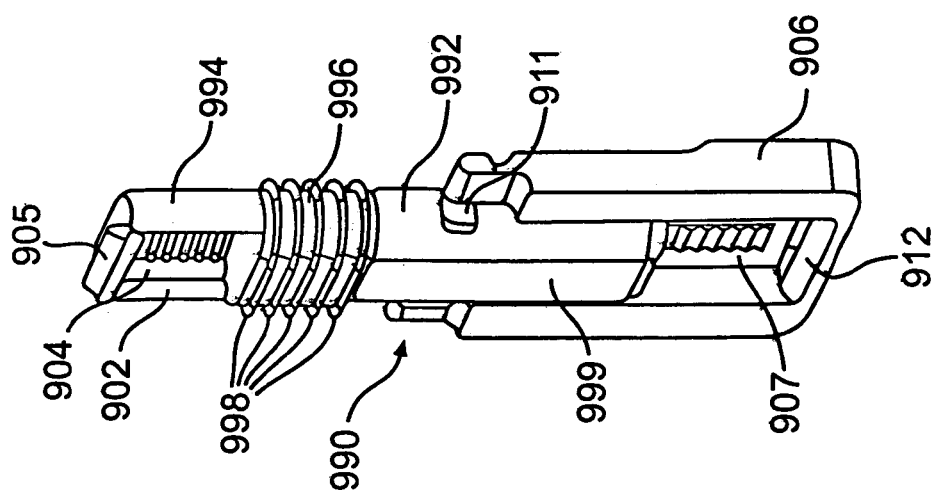
FIG. 42a is a perspective view of a further embodiment of a sample collector with the cover in the open position.
Figure 43:
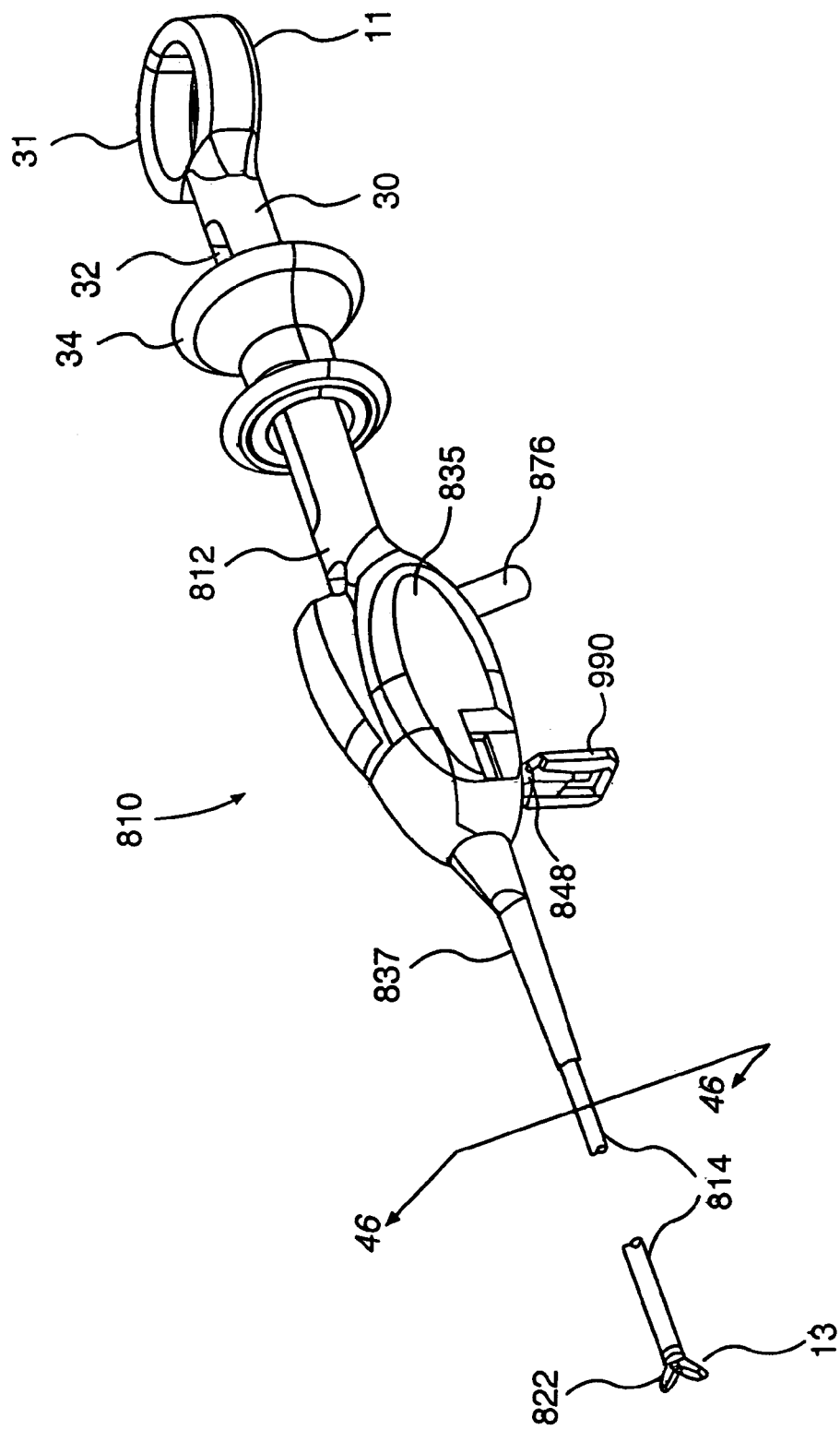
FIG. 43 is a perspective view of a biopsy instrument in accordance with still another embodiment of the present invention.

An alternative configuration of the sample collector for use in, for example, the biopsy instrument of FIG. 43, is shown in FIGS. 42*a* and 42*b*. As illustrated in FIGS. 42*a*-42*b*, sample collector assembly 990 includes catcher handle 992 and catcher body 994. Catcher handle 992 has a securing end 996 for insertion into a sample catcher port 848. In this configuration, securing end 996 includes a plug with an ovoid cross-section and multiple, flexible circumferential rings 998 that complement sample catcher port 848 to provide a seal therewith. Rings 998 are preferable integrally molded to catcher handle 992. As will be appreciated by persons skilled in the art, other access opening configurations and complementary catcher handle securing ends may be used without departing from the scope or spirit of the invention. For instance, a different cross-section of securing end 996, or a fewer or greater number of flexible rings 998, or flexible rings 998 that are not integrally molded to catcher handle 992 are all within the scope of the present invention.

Catcher handle 992 has a gripping end 999, opposite to securing end 996, for enabling the nurse or surgeon to firmly grip and easily manipulate sample collector 990. The present embodiment of gripping end 999 includes a shaft with a quasi-rectangular cross-section.

As illustrated in FIG. 42*a*, catcher body 994 includes a flow opening 902, a screen 904, and a projection 905. Catcher body 994 is insertable into and configured to complement the suction passageway portion of sample catcher port 848. Catcher body 994 permits fluid flow in a suction passageway 844 to continue downstream, while trapping and retaining any solid matter, such as a tissue sample, passing through suction passageway 844.

Similarly to previously described catcher body 794, catcher body 994 has a flow opening 902 on its upstream side and a screen 904 on its downstream side. Screen 904 is located on the downstream side of catcher body 994 to trap matter after such matter has entered flow opening 902. As shown in FIG. 42*a*, screen 904 may consist of a horizontal and vertical latticework.

As illustrated in FIGS. 42*a*-42*b*, sample collector 990 includes cover 906 positionable between an open position displaced from flow opening 902 of catcher body 994 (FIG. 42*a*) and a closed position overlaying flow opening 902 (FIG. 42*b*). In a closed position, a ridge 912 on cover 906 may snap over projection 905 on catcher body 994 to secure cover 906 in a closed position over catcher body 994.

As embodied herein, cover 906 may be rotatably attached to catcher handle 992 via hinge 911. Hinge 911 may be formed from material that deforms when cover 906 is rotated from the open position to the closed position. As such, hinge 911 requires no movable parts. The elastic or plastic deformation of the material of hinge 911 allows the rotational displacement of the hinge to occur. In a preferred embodiment, catcher body 994, catcher handle 992, cover 906, and hinge 911 are integrally molded as a single piece. Alternatively, hinge 911 may be conventionally formed from pivot pins and holes or detent assemblies without departing from the scope of the invention.

Furthermore, as embodied herein, catcher body 994, with cover 906 in a closed position, is configured to fit into a standard pathology and histology processing cartridge. Similar to cover 706, cover 906 may include a cover screen 907 to permit the fluids involved in the pathology process to easily and completely gain access to the sample.

As with sample collector 790, sample collector 990 is preferably made of plastic that is chemically inert to the chemicals used in pathology processing, specifically nylon, although other plastics such as polypropylene or polyethylene, or even a suitable glass or metal, may be used. Similarly, a preferred method of manufacturing sample collector 990 is by injection-molding.

Operation of a biopsy instrument according to the present invention will now be described with reference to FIGS. 10, 11 and 38-42. When a surgeon desires to take a tissue sample 112 from within a patient's body without invasive surgery, the surgeon inserts distal end 13 of biopsy instrument 710 into an orifice of a patient under treatment. While retaining control of proximal actuation handle 712, the surgeon guides distal assembly 22 through the patient's body to a position adjacent a tissue to be sampled. In a preferred embodiment, the surgeon uses endoscopic technology to ensure proper positioning of the distal assembly. The surgeon inserts distal end 13 of biopsy instrument 710 into an irrigation endoscope already inserted and properly located within a patient's body. Distal assembly 22 is threaded through the irrigation endoscope until the surgical site is reached.

At the surgical site, opened movable jaw 90 is then positioned around the tissue to be sampled, as illustrated in FIG. 10. In a preferred embodiment, once jaw 90 is properly positioned, the surgeon creates a vacuum effect in aspiration conduit 74 and within concave cavity 101 of stationary jaw 88 by depressing aspiration valve 682. This vacuum effect draws the tissue to be sampled into concave cavity 101 and aids the in the severance of the sample from the surrounding tissue.

The surgeon then proceeds to slide actuator spool 34 along shaft 30 of proximal actuation handle 712 in the proximal direction. This, in turn, axially displaces pull wire 20 in the proximal direction causing movable jaw 90 to pivot about pivot pin 94. Distal assembly 22 is thereby closed, and tissue sample 112 is separated from the surrounding tissue when sharp cutting edge 98 of movable jaw 90 comes into contact with blunt edge 92 of stationary jaw 88. As illustrated in FIG. 11, severed tissue sample 112 is enclosed within the passageway formed by cup-like body 95 of movable jaw 90 and concave cavity 101 of stationary jaw 88.

If not already established in aspiration conduit 74, the surgeon initiates a vacuum effect in aspiration conduit 74 by depressing aspiration valve 682. Tissue sample 112 is aspirated from distal end 13 through aspiration conduit 74 and suction passageway 662 and into sample collector 790 under the action of the vacuum effect.

However, on occasion, tissue sample 112 may become lodged in distal assembly 22, aspiration conduit 74 or in suction passageway 662. When this happens, the surgeon may then choose to provide fluid to the biopsy site at distal end 13. With a vacuum effect established in aspiration conduit 74, any fluid provided to distal end 13 will be aspirated through aspiration conduit 74, and thereby aid in the retrieval of tissue sample 112. In a preferred embodiment, irrigation fluid from an irrigation endoscope is provided to the biopsy site. Alternatively, the surgeon may initiate a flow from fluid source 632 through irrigation conduit 72 of biopsy instrument 710 to distal end 13 in order to aid in the aspiration of tissue sample 112 to sample collector 790. In addition, the pressure of fluid supplied from source 632 may be increased with the use of pressure increasing devices previously described.

Once tissue sample 112 is trapped by screen 704, the surgeon or nurse may disengage sample collector 790 from access opening 768 of proximal actuation handle 712. Cover 706 is then slid, rotated or snapped over flow opening 702 of catcher body 794 capturing sample 110 within catcher body 94. The surgeon or nurse then disconnects catcher body 794 from catcher handle 792 by snapping or twisting off break-away tab 708 from securing end 796. Catcher body 794 may be placed in a specimen collection jar for later processing and examination.

The surgeon may then reposition distal end 13 proximate to the next tissue sample 112 to be collected, and proceed to obtain and recover a second tissue sample 112 by repeating the above process. In this manner, the surgeon may recover multiple tissue samples without the necessity of removing distal end 13 of biopsy instrument 710 from the body of the patient.

Another embodiment of a biopsy instrument according to the present invention is shown in FIG. 43. This embodiment generally relates to a pinch biopsy apparatus with aspiration capabilities and a method of using such. In a pinch biopsy apparatus, as will be described below, it is preferred that both jaws of the distal assembly are manipulable and capable of rotating away from one another. With the jaws in an open position, i.e., rotated away from one another, the operator is able to site the tissue to be sampled deep within the jaws of the distal assembly. Closing the jaws, i.e., rotating the jaws towards each other, causes the tissue within the jaws to be disengaged from the surrounding tissue.

One advantage of having both jaws of the distal assembly capable of rotating away from one another is that larger tissue samples may be acquired. Because both jaws of a pinch biopsy instrument rotate away from one another, the jaws in their opened position may realize a relatively large included angle. The fully opened jaws may be more completely positioned around a portion of tissue to be sampled as compared to an end effector assembly wherein one of the jaws is stationary. Thus, a pinch biopsy instrument is capable of detaching relatively large tissue samples.

A second advantage of having both jaws of the distal assembly capable of rotating away from one another is that the tissue to be severed is located directly along the longitudinal axis of the pinch biopsy instrument. Thus, the operator may directly approach the tissue site rather than having to manipulate the biopsy instrument to approach the tissue site from an angle.

A biopsy instrument according to the embodiment of FIG. 43 generally includes a distal assembly 822 for use in a surgical operation, an elongated flexible member 814, and a proximal actuation handle 812. Biopsy instrument 810 has a distal end 13 and a proximal end 11.

Figure 44:
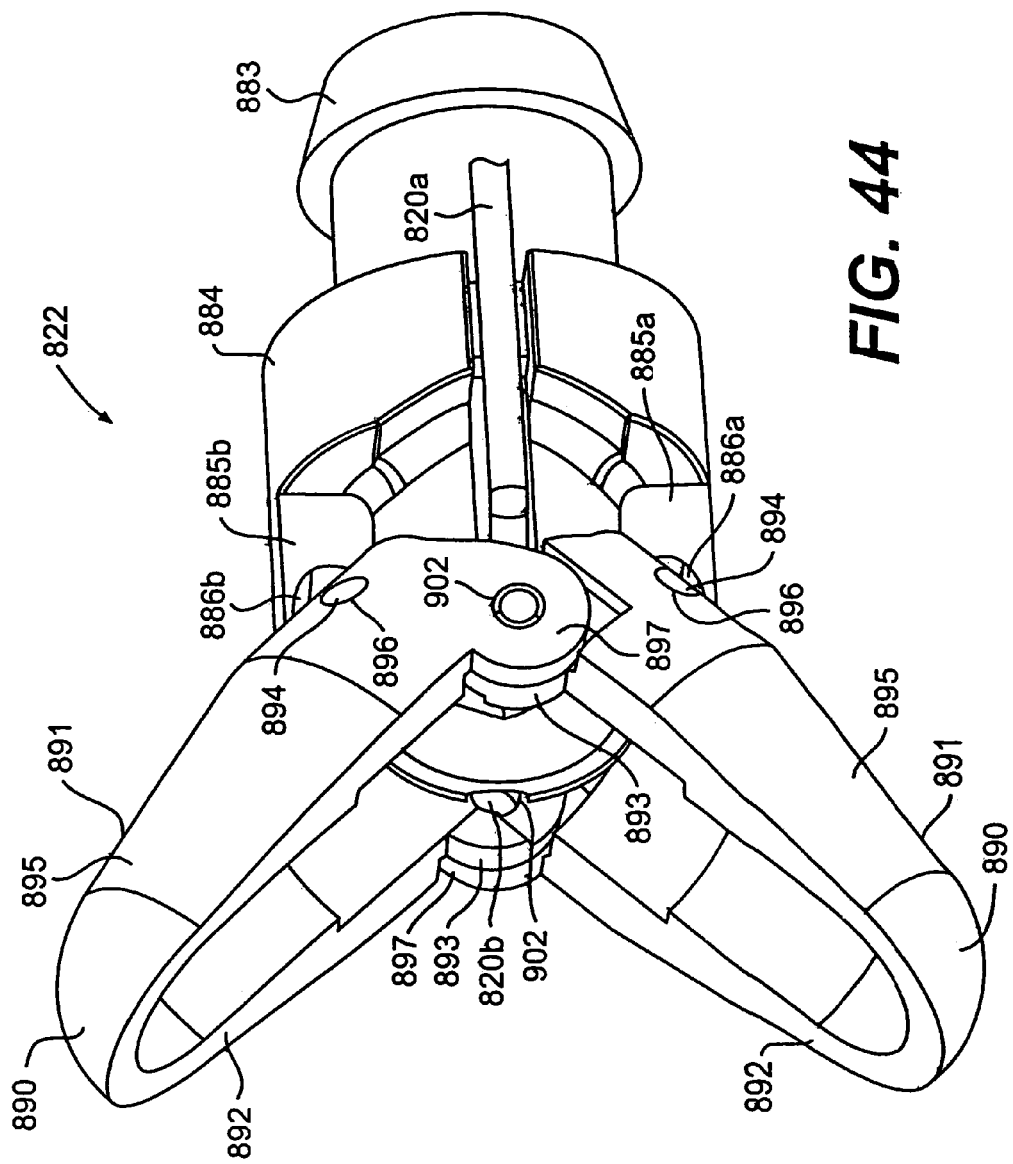
FIG. 44 is a perspective view of a distal assembly of the biopsy instrument of FIG. 43.

According to the present embodiment, distal assembly 822 includes first and second movable jaws. As shown in FIG. 43, distal assembly 822 is located on the distal end of flexible member 814 opposite proximal actuation handle 812. As shown in FIG. 44, distal assembly 822 includes first and second pivotably movable hermaphroditic jaws 890. Each jaw 890 includes a cup-like body 895 having a quasi-cylindrical back wall 891 and a mating edge 892. When distal assembly 822 is in a closed configuration, mating edge 892 of first jaw 890 contacts mating edge 892 of second jaw 890. Mating edge 892 may be used for cutting, crushing, grasping, or ripping a tissue sample from the surrounding tissue. Accordingly, mating edge 892 may be sharp, blunt, serrated, or notched. In a preferred embodiment, mating edges 892 include sharp, mating teeth for cutting a tissue sample.

Each jaw 890 is provided with an outer flange 897 and an inner flange 893, located at the proximal end of jaw 890 adjacent mating edge 892. Each outer flange 897 and each inner flange 893 is provided with a radially-directed through hole 902 for receiving one of pull wires 820a, 820b. In an assembled configuration, outer flange 897 of first jaw 890 lies adjacent inner flange 893 of second jaw 890, and through holes 902 are in-line. Similarly outer flange 897 of second jaw 890 lies adjacent inner flange 893 of first jaw 890 with through holes 902 lined up. As described below, the distal ends of pull wires 820a, 820b are inserted into through holes 902 in the assembled configuration.

Each jaw 890 is further provided with a pivot hole 896 located proximate the proximal end of jaw 890. Pivot hole 896 is transverse to, and proximate, the spine of quasi-cylindrical back wall 891.

Figure 45:
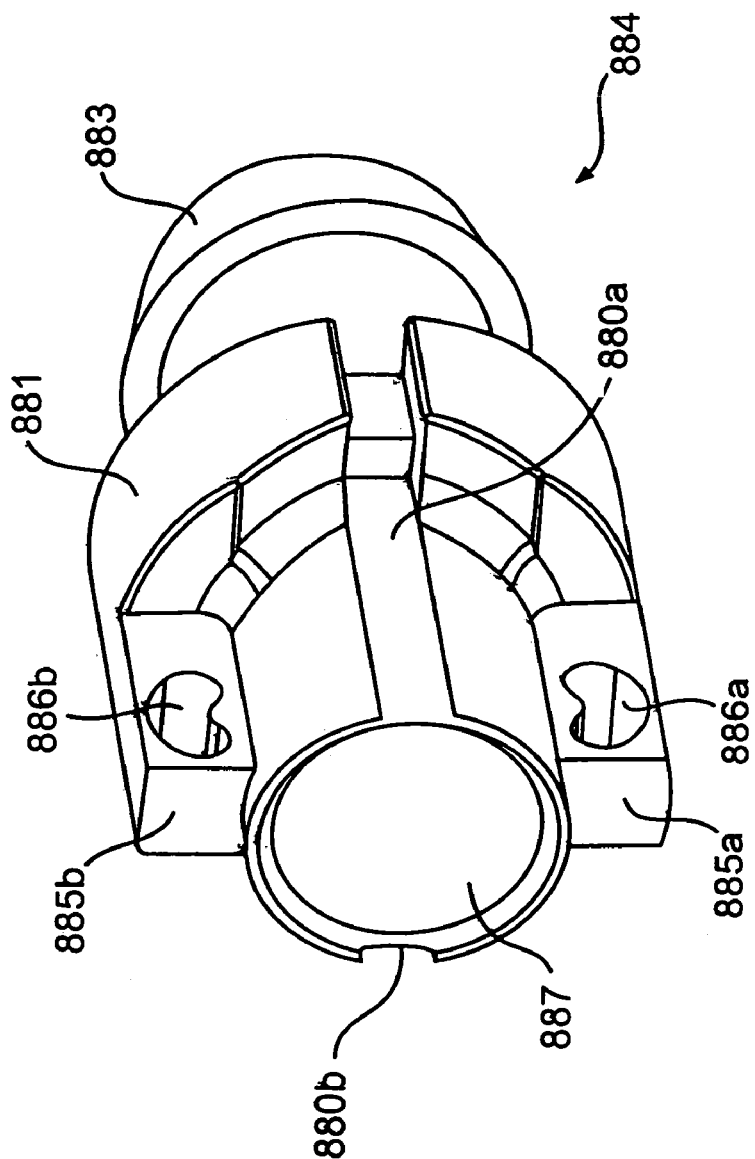
FIG. 45 is a perspective view of a portion of the distal assembly of the biopsy instrument of FIG. 43.

Distal assembly 822 further includes distal end conduit 884. According to the present embodiment and as shown in FIG. 45, distal end conduit 884 includes a central cylindrical passageway 887, a cylindrical body 881, a pair of longitudinal flanges 885a, 885b, a pair of channels 880a, 880b, and a cylindrical barbed connector 883. Central cylindrical passageway 887 extends through cylindrical body 881 from the distal to the proximal end of distal end conduit 884. Longitudinal flanges 885a, 885b are diametrically opposed, extend in a distal direction from cylindrical body 881 and in a radially outward direction from the outer wall of cylindrical passageway 887. Pivot holes 886a, 886b extend transversely through longitudinal flanges 885a, 885b, respectively. Diametrically opposed channels 880a, 880b extend longitudinally along the outer wall of cylindrical passageway 887 and are located ninety degrees from longitudinal flanges 885a, 885b. Cylindrical barbed connector 883, located at the proximal end of distal end conduit 884, is formed from a step increase in the outer diameter of the outer wall of cylindrical passageway 887.

Further according to the present embodiment, each jaw 890 of distal assembly 822 is pivotably coupled over the distal end conduit 884. Pivot pins 894 are inserted through pivot holes 896 of each jaw 890 and through pivot holes 886a or 886b of distal end conduit 884. Thus, each jaw 890 is pivotably coupled to distal end conduit 884. Furthermore, each jaw 890 is pivotably coupled to distal end conduit 884 in such a manner that central cylindrical passageway 887 is unobstructed whether distal assembly 822 is in an opened or closed configuration.

As shown in FIG. 45, pivot holes 886a, 886b of distal end conduit 884 are somewhat kidney-shaped, having a proximal end pivot pin seat and a distal end pivot pin seat. This profile enhances the extent to which jaws 890 may be rotated away from each other. When distal assembly 822 is in an opened configuration, pivot pins 894 are seated at the distal end of pivot holes 886a, 886b. In a closed configuration, pivot pins 894 are seated at the proximal end of pivot holes 886a, 886b.

Figure 46:
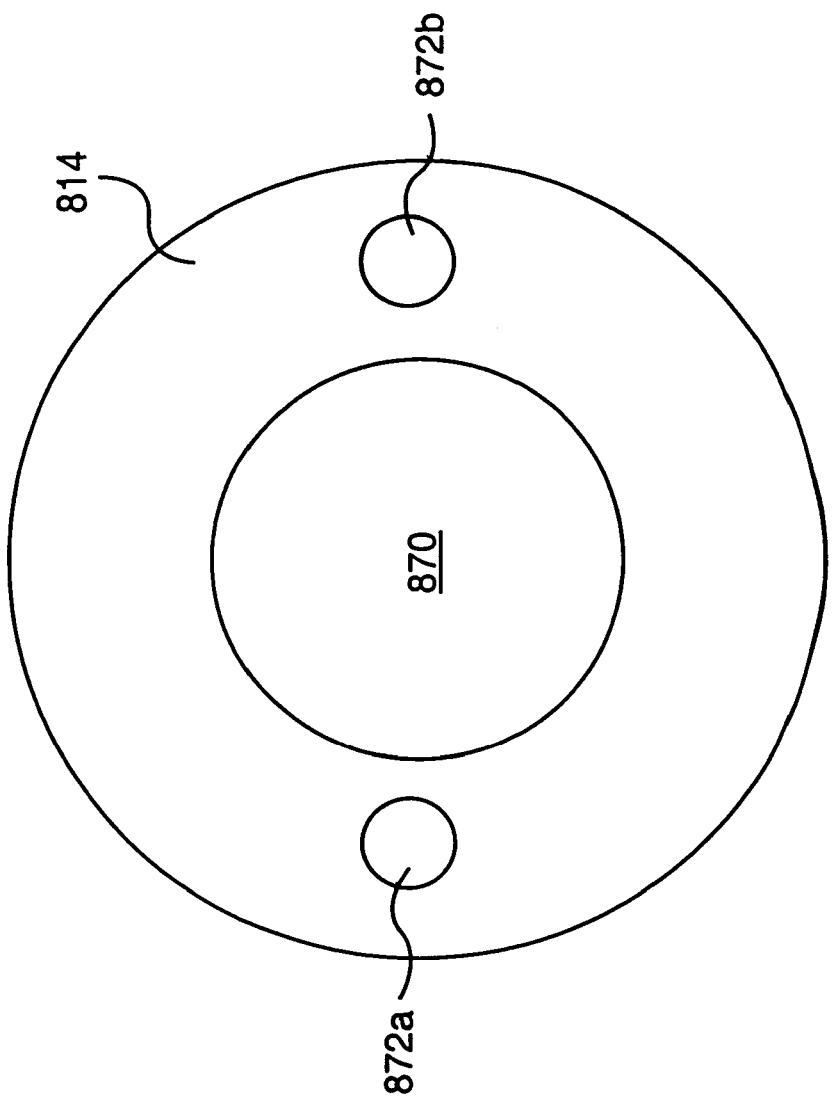
FIG. 46 is an enlarged cross-section across line 46-46 of FIG. 43.

The biopsy instrument according to the present embodiment further includes an elongate flexible member 814 connected to and extending from distal assembly 822 toward proximal end 11. As shown in FIG. 46, flexible member 814 includes an aspiration conduit 870 in fluid connection with distal end conduit 884 for permitting the passage of matter, and particularly, tissue samples, from distal end 13 toward proximal end 11. Aspiration conduit 870 may be concentric with elongate flexible member 814. The distal end of flexible member 814 may be press fit over barbed connector 883 of distal end conduit 884. Flexible member 814 may also be fitted over barbed connector 883 and held in place with a crimp band or other mechanical fastener. Alternatively, flexible member 814 may be bonded to the proximal end of distal end conduit 884. Flexible member 814 is also provided with diametrically opposed control conduits 872a, 872b. Pull wires 820a, 820b extend through control conduits 872a, 872b, respectively.

Figure 47:
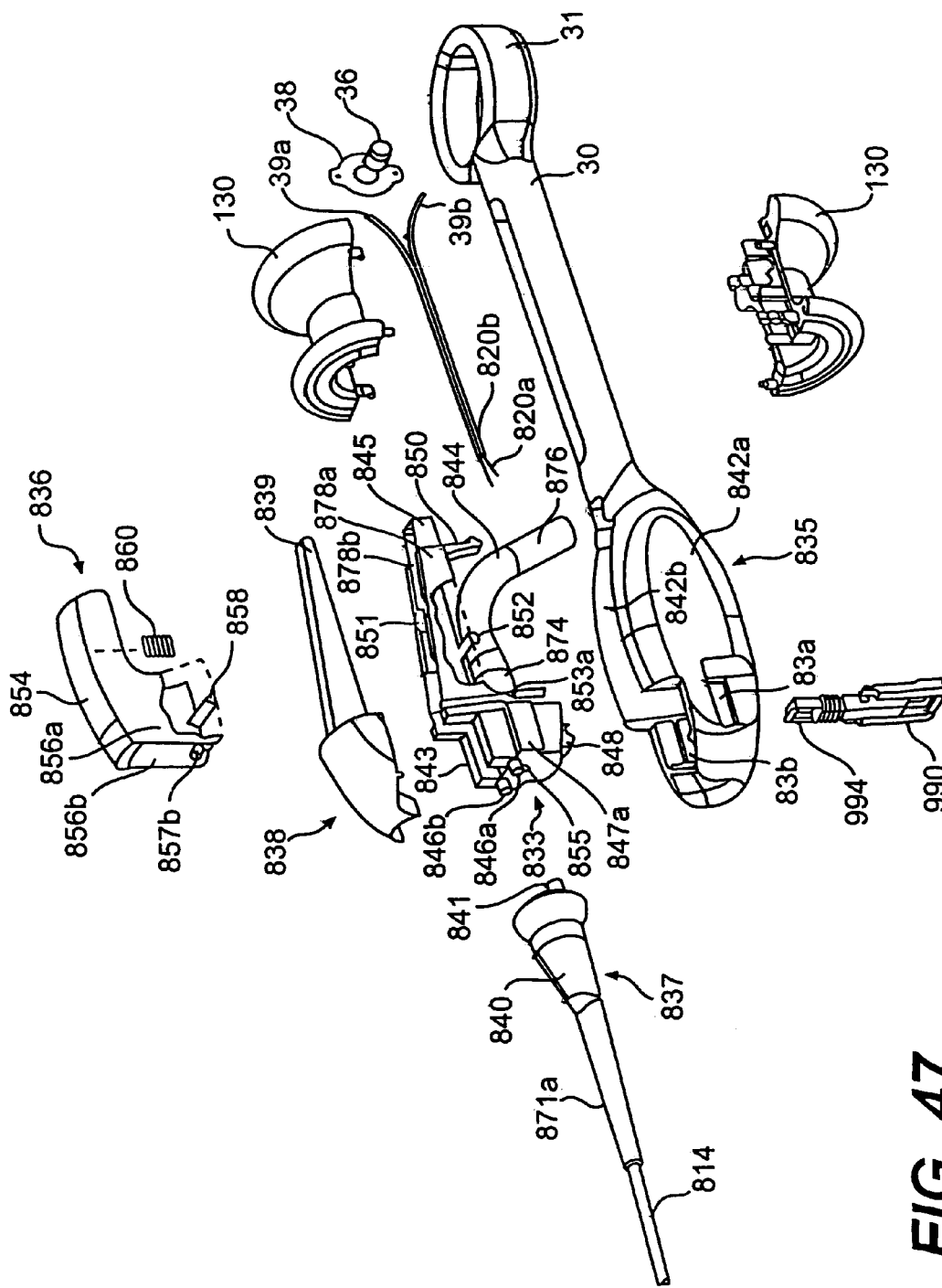
FIG. 47 is an exploded perspective view of a portion of the biopsy instrument of FIG. 43.

The biopsy instrument according to the present embodiment is further provided with a proximal actuation handle 812 including a stationary member and an actuation device. As shown in FIGS. 43 and 47, the stationary member includes nose member 837, outer body 835, inner body 833, cover 838, lever 836, shaft 30, and thumb ring 31. The stationary member is connected to the proximal end of flexible member 814. Furthermore, the stationary member has a suction passageway 844 in fluid connection with the aspiration conduit 870, wherein suction passageway 844 is for fluid connection with a vacuum source (not shown).

Nose member 837 couples flexible member 814 to a sample catcher chamber 843 of inner body 833. Nose member 837 includes a body 840 that is provided with a strain relief portion 871a at its distal end and a coupling portion at its proximal end. Strain relief portion 871a is an elongate, gradually tapering, conical section which prevents flexible member 814 from bending too abruptly and thereby becoming overstrained at the attachment of flexible member 814 to nose portion 837. Strain relief portion 871a permits flexible member 814 to gradually bend over the length of strain relief portion 871a.

As embodied herein, body 840 is insert-molded to the proximal end of flexible member 814 as follows: wires of approximately the same diameter as the aspiration conduits 870 and control conduits 872a, 872b are inserted into, and extend from, these conduits at the proximal end of flexible member 814; the proximal end of flexible member 814, with the wires, is placed into the mold for body 840; resin is injected into the closed mold; upon removing body 840 from the mold, the wires are pulled free. In this manner, body 840 is insert-molded to the proximal end of flexible member 814 and conduits 870, 872a and 872b are extended through body 840. As shown in FIG. 47, the proximal end of body 840 may be provided with a molded port 841 at the proximal end of aspiration conduit 870 for insertion into sample catcher chamber 843 of inner body 833. Body 840 may also be provided with mating slot's (not shown) at its proximal end for mating with mating tabs 846a, 846b of sample catcher chamber 843, as described below.

Figure 49:
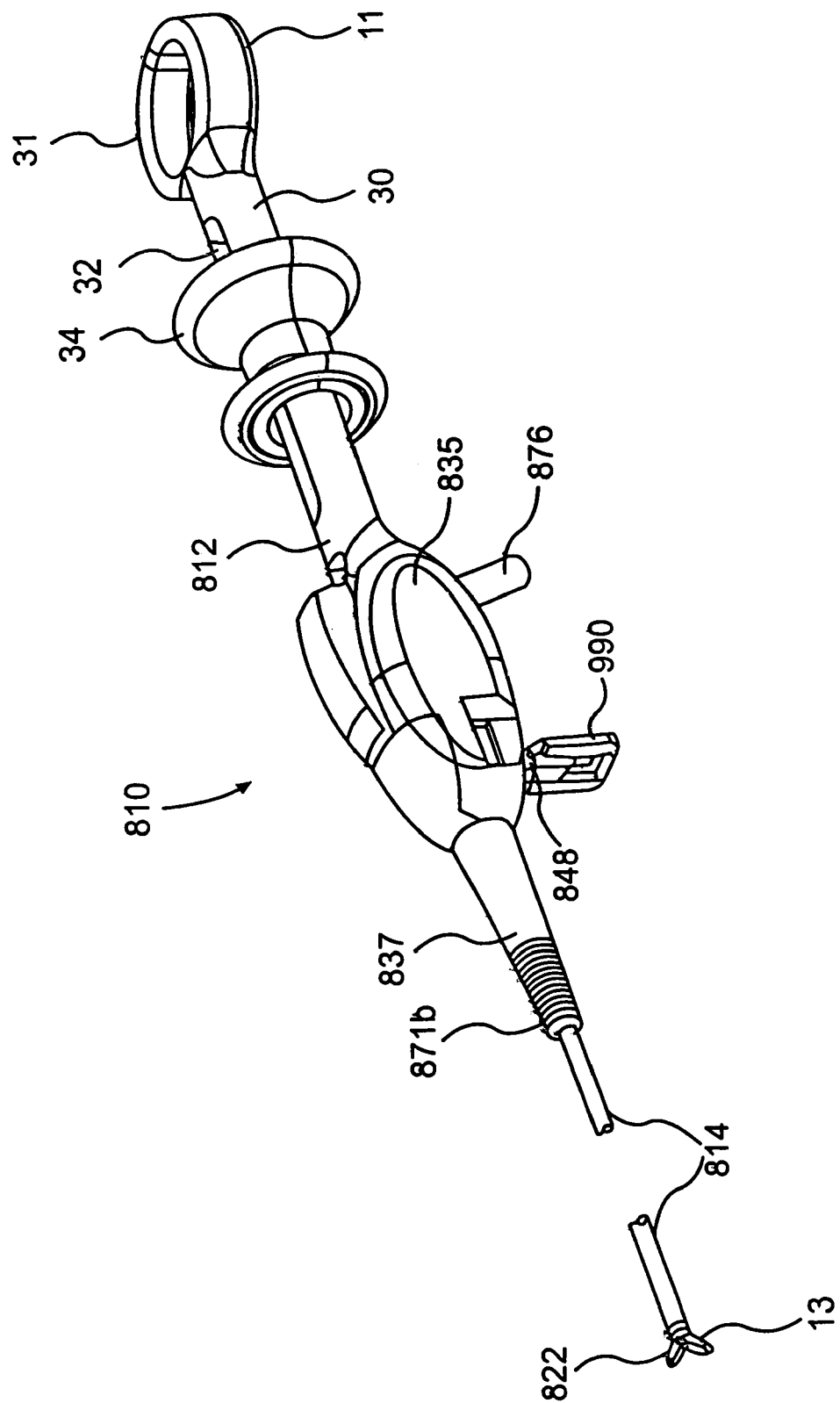
FIG. 49 is a perspective view of the biopsy instrument of FIG. 43 with an alternative strain relief portion on the nose member of the proximal actuation handle.

As shown in FIG. 49, nose member 837 may be provided with an alternative flexible strain relief portion at its distal end. Strain relief portion 871b resembles a graduated series of rings and may be formed by circumferentially cutting the outer surface of nose member 837, or alternatively, strain relief portion 871b may be integrally molded into nose member 837.

Outer body 835 is provided with sides 842a, 842b, which include viewing holes 83a, 83b, respectively. Viewing holes 83a, 83b permit the operator to view the interior of the sample catcher chamber 843. Alternatively, viewing holes 83a, 83b may be transparent windows. Outer body 835 is attached at its proximal end to shaft 30 by any suitable connection means, for example, adhesive bonding. Shaft 30 and thumb ring 31 have been previously described. Outer body 835 has an opening at its distal end for abutting the proximal end of body 840 of nose member 837, but is not necessarily directly attached to nose member 837.

As shown in FIG. 47, inner body 833 is provided with a sample catcher chamber 843, a suction passageway 844, and a pinch valve extension 845. Sample catcher chamber 843, located at the distal end of inner body 833, couples aspiration conduit 870 to suction passageway 844. At its distal end, sample catcher chamber 843 is provided with aspiration opening 855. Aspiration opening 855 complements aspiration port 841 of nose member 837. Aspiration port 841 press fits into aspiration opening 855. At its proximal end, sample catcher chamber 843 is provided with a connector (not shown) for coupling to suction passageway 844. Suction passageway 844 may be fitted over the connector and held in place with a crimp band or other mechanical fastener, or alternatively, suction passageway 844 may be bonded to the connector.

Sample catcher chamber 843 is further provided with a flow-passage portion (not shown) for flow-connecting aspiration conduit 870 to suction passageway 844. This flow-passage portion is configured to complement and receive catcher body 994 of sample collector 990.

Sample catcher chamber 843 further is provided with mating tabs 846a, 846b, viewing ports 847a, 847b, pin holes 853a, 853b, and sample catcher port 848. Mating tabs 846a, 846b extend in a distal direction from the distal end of sample catcher chamber 843, and are for mating with the complementary mating slots (not shown) of body 840. Viewing ports 847a, 847b are located on opposing sides of the flow-passage portion of sample catcher chamber 843 and are aligned with viewing holes 83a, 83b when inner body 833 is assembled with outer body 835. Viewing ports 847a, 847b are made of transparent material and permit the operator to view the interior of sample catcher chamber 843. Preferably, the entire sample catcher chamber 843 is molded from a transparent plastic. Pin seats 853a, 853b are provided on opposing sides of sample catcher chamber 834 proximal from and adjacent to viewing ports 847a, 847b. As described below, pin seats 853a, 853b permit lever 836 to be rotatably coupled to inner body 833. Sample catcher port 848 permits access to the flow-passage portion of sample catcher chamber 843 and, as will be described below, insertion of sample collector 990. Sample catcher port 848 extends transversely to viewing ports 847a, 847b and transversely to aspiration conduit 870 and suction passageway 844. As best shown in FIG. 43, when inner body 833 is assembled within outer body 835, sample catcher port 848 is positioned external to outer body 835.

Suction passageway 844 extends from sample catcher chamber 843 to a vacuum connector 876 that attaches suction passageway 844 to the vacuum source (not shown). Suction passageway 844 includes flexible vacuum tubing wherein the tubing may be elastically deformed to permit repeated blocking and unblocking of the passageway. As previously described, suction passageway 844 is coupled in a fluid-tight connection with sample catcher chamber 843 via a connector. Vacuum connector 876 provides a connectable and disconnectable fluid-tight coupling between suction passageway 844 and the vacuum source. As best shown in FIG. 43, when inner body 833 is assembled within outer body 835, vacuum connector 876 is positioned external to outer body 835.

As shown in FIG. 47, pinch valve extension 845 extends in a proximal direction from sample catcher chamber 843. Furthermore, pinch valve extension 845 extends approximately parallel to and adjacent the portion of suction passageway 844 adjacent sample catcher chamber 843. Pinch valve extension 845 includes sides 878a, 878b, latch 850, pinch valve upper bar 852, and spring seat 851. Sides 878a, 878b define the proximal portion of a slot therebetween, and flank extension 839 of nose member 837 when actuation handle 812 is assembled. Latch 850 snaps into a complementary keyway in outer body 835, thus securing inner body 833 to outer body 835. Pinch valve upper bar 852 extends from side 878a to side 878b, transverse to suction passageway 844, and is located on the edges of sides 878a, 878b adjacent suction passageway 844. As described below, pinch valve upper bar 852 provides part of the mechanism for starting and stopping the vacuum effect in aspiration conduit 870. Spring seat 851 is located approximately midway along the length of pinch valve extension 845. Also as described below, spring seat 851 provides a seat for a spring 860 which biases lever 836 away from pinch valve extension 845.

Cover 838 lays on top of sample catcher chamber 843 of inner body 833 and includes extension 839 extending in a proximal direction. Cover 838 and extension 839 retain and guide hypotubes 39a, 39b and pull wires 820a, 820b which slide back and forth when actuation spool 34 is actuated. Alternatively, cover 838 may be integrally attached to sample catcher chamber 843 by, for example, adhesive bonding.

Lever 836 includes lever handle 854, lever flanges 856a, 856b, pinch valve lower bar 858, and spring 860. Lever handle 854 provides a surface on which an operator may push to activate a vacuum effect in aspiration conduit 870. Lever flanges 856a, 856b extend from opposite sides of lever handle 854. Flanges 856a, 856b are separated such that when actuation handle 812 is assembled, flanges 856a, 856b lie outside of and adjacent to sides 878a, 878b of pinch valve extension 845 of inner body 833 and inside of and adjacent to sides 842a, 842b of outer body 835.

Flanges 856a, 856b are provided with pins 857a, 857b, respectively, located on the inner surfaces proximate the proximal end of lever 836. Pins 857a, 857b complement holes 853a, 853b located on sample catcher body 843, and are for rotatably coupling lever 836 to inner body 833.

Pinch valve lower bar 858 extends from flange 856a to flange 856b, transverse to suction passageway 844, and is located proximate the edges of flanges 856a, 856b opposite lever handle 854. In the assembled configuration, pinch valve lower bar 858 is located adjacent suction passageway 844 opposite pinch valve upper bar 852. Spring 860 is a compression spring located between flanges 856a, 856b. In the assembled configuration, spring 860 extends from the under surface of lever handle 854 to spring seat 851 of pinch valve extension 845 of inner body 833, and pushes lever handle 854 away from inner body 833. Pushing lever handle 854 away from inner body 833 causes pinch valve lower bar 858 to come towards pinch valve upper bar 852. Suction passageway 844, located between pinch valve lower bar 858 and pinch valve upper bar 852, is thus pinched flat and no vacuum is effected within aspiration conduit 870. When an operator presses on lever handle 854, spring 860 is compressed and pinch valve lower bar 858 is moved away from pinch valve upper bar 852. In this manner, suction passageway 844 is opened and a vacuum effect is introduced into aspiration conduit 870.

It is to be understood that alternative devices for starting and stopping the vacuum effect in aspiration conduit 870 may be used. For instance, an arrangement may be envisioned whereby the spring biases suction passageway 644 open. As a further example, spring 860 could be a torque spring or other spring element rather than a compression spring. These and other variations are within the scope of the invention.

As shown in FIGS. 43 and 47, proximal actuation handle 812 further is provided with an actuation device. As previously described, the actuation device includes actuation spool 34, swash plate 38 and swash plate axle 36.

The biopsy instrument according to the present embodiment includes a control member coupled to the actuation device. As embodied herein and as shown in FIGS. 44 and 47, the control member includes pull wires 820a, 820b. As best shown in FIG. 47 and as described in relation to a previously disclosed embodiment, the proximal end of pull wires 820a, 820b are coupled to actuation spool 34, comprised of hermaphroditic spool halves 130, via swash plate 38 and swash plate axis 36.

Also according to the present embodiment, the control member is coupled to the first and second movable jaws of the distal assembly. As shown in FIG. 44, the distal end of pull wires 820a, 820b are coupled to first and second jaws 890. Specifically, with distal assembly 822 in an assembled configuration, the distal end of pull wire 820a is inserted into the aligned, radially-directed holes 902 of outer flange 897 of first jaw 890 and inner flange 893 of second jaw 890. Similarly, the distal end of pull wire 820b is inserted into the aligned, radially-directed holes 902 of outer flange 897 of second jaw 890 and inner flange 893 of first jaw 890. It should be noted that due to the geometric constraints imposed upon the distal ends of pull wires 820a, 820b when in the assembled configuration, no secondary operations or additional parts are required to retain pull wires 820a, 820b in holes 902.

Figure 48:
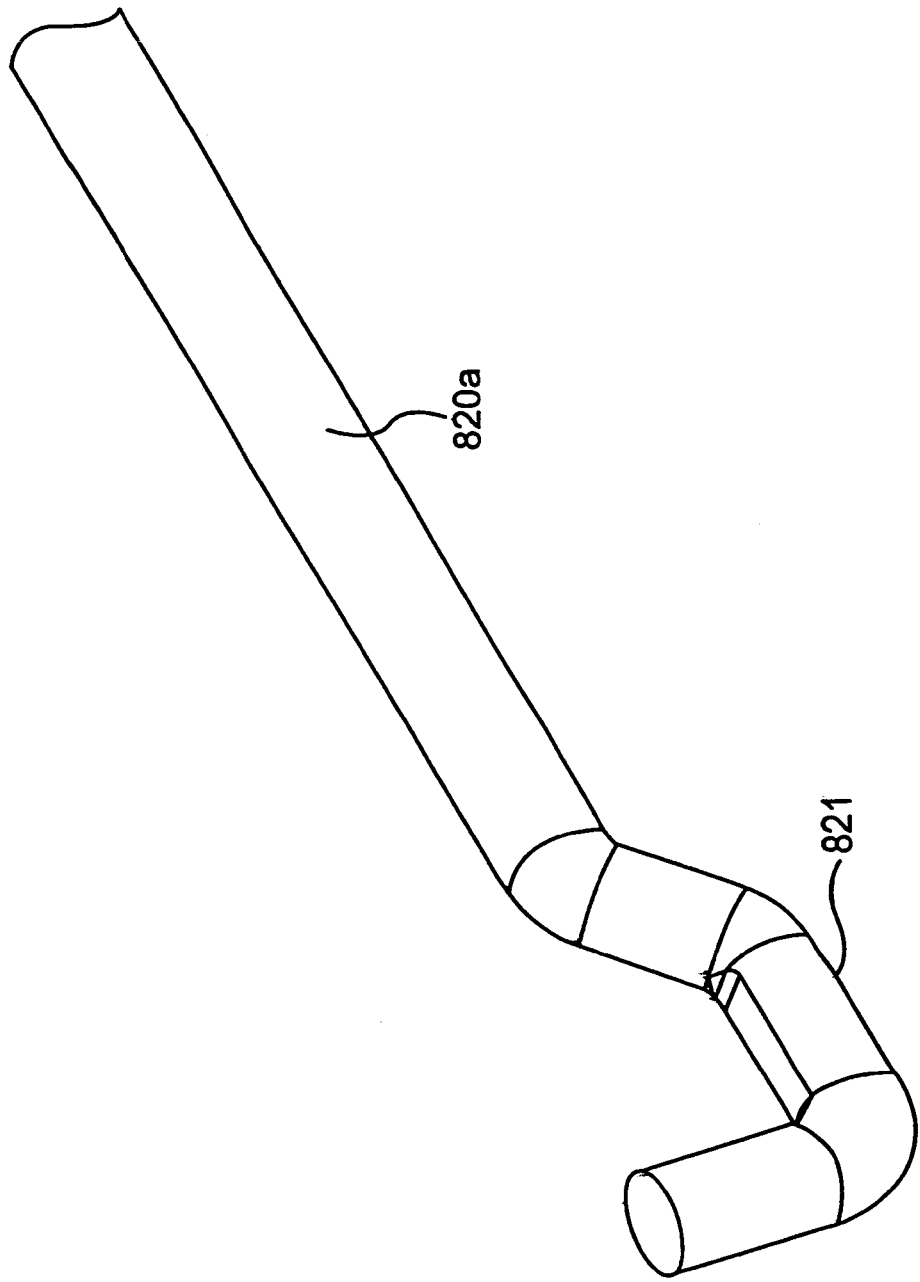
FIG. 48 is a perspective view of the distal end of a pull wire for use in connection with the biopsy instrument of FIG. 43.

As shown in FIG. 48, the distal ends of pull wires 820a, 820b are shaped to accommodate the geometry of distal assembly 822. Bend portions 821 provide clearance for inner flanges 893 and outer flanges 897. Furthermore, bend portions 821 slide within channels 880a, 880b, respectively, of distal end conduit 884.

According to the present embodiment, actuation of the actuation device pivots the first and second movable jaws relative to the flexible member. Pull wires 820a, 820b are coupled to and extend from holes 902 of jaws 890 at distal assembly 822 through control conduits 870a, 870b, respectively, of flexible member 814. Pull wires 820a, 820b then extend through actuation handle 812 and are coupled to actuation spool 34. Moving actuation spool 34 in a distal direction relative to shaft 30 causes pull wires 820a, 820b to move in a distal direction relative to flexible member 814 and distal end conduit 884. This, in turn, causes holes 902 of jaws 890 to move in a distal direction relative to pivot pin 894 which is coupled to distal end conduit 884. Mating edges 892 of jaws 890 are thereby rotated away from each other and distal assembly 822 assumes an opened configuration. Similarly, moving actuation spool 34 in a proximal direction relative to shaft 30 causes mating edges 892 of jaws 890 to rotate towards one another, whereby distal assembly 822 assumes a closed configuration.

The biopsy instrument of the present embodiment includes a sample collector to trap and retain biopsy samples severed by operation of the distal assembly 822. As illustrated in FIG. 43, biopsy instrument 810 includes sample collector assembly 990 provided in-line with suction passageway 844. Sample collector assembly 990 acts as a filter to trap matter, such as biopsy samples, flowing through suction passageway 844. Matter trapped by sample collector assembly 990 may then be retrieved by the surgeon or nurse for subsequent pathological examination. Sample collector 990, as shown in FIGS. 42a and 42b, has been previously described.

The above descriptions of the embodiments of the invention have been presented for purposes of illustration and description. It is not intended to be exhaustive or to limit the invention to the precise forms disclosed. Modifications and variations are possible in light of the above teachings, or may be acquired from practice of the invention. For example, it is contemplated that features of an embodiment may be combined with features of other embodiments, resulting in combinations of features not specifically disclosed herein. The specific embodiments disclosed were described in order to explain the principles of the invention, and its practical application was described to enable one skilled in the art to utilize the invention in various embodiments and with various modifications as are suited to the particular use contemplated. Thus, it is intended that the present invention cover the modifications and variations of this invention provided they come within the scope of the appended claims and their equivalents.

We claim:

1. A biopsy instrument having a proximal end and a distal end, comprising:
    a distal assembly for performing a surgical operation;
    an elongate flexible member connected to and extending in a proximal direction from the distal assembly, the flexible member including a conduit therethrough;
    a proximal actuation handle coupled to a proximal end of the flexible member, the proximal actuation handle including an access opening in fluid connection with the conduit; and
    a sample collector including a catcher handle and a catcher body, wherein the catcher body is configured for insertion into the access opening and is removably attached to the catcher handle.

2. The biopsy instrument of claim 1, wherein the conduit is an aspiration conduit and the proximal actuation handle includes an aspiration port in fluid connection with a proximal end of the aspiration conduit and for fluid connection to a suction device.

3. The biopsy instrument of claim 2, further comprising an irrigation conduit through the elongate flexible member, and the proximal actuation handle includes an irrigation port in fluid connection with a proximal end of the irrigation conduit and for fluid connection to a fluid source.

4. The biopsy instrument of claim 2, wherein the sample collector is disposed in-line with the aspiration conduit and the suction device and located therebetween.

5. The biopsy instrument of claim 1, wherein the catcher body includes a screen.

6. The biopsy instrument of claim 5, wherein the proximal actuation handle includes a suction passageway with the access opening at a proximal end of the suction passageway, wherein the screen is positionable within the suction passageway upon insertion into the access opening.

7. The biopsy instrument of claim 5, wherein the catcher handle includes a securing end;
    wherein the screen is removably attached to the securing end of the catcher handle.

8. The biopsy instrument of claim 1, wherein at least one flexible ring encircles one of the catcher handle or the catcher body for providing a seal with the access opening.

9. The biopsy instrument of claim 1, wherein the sample collector includes a screen and a cover positionable between an open position displaced from the screen and a closed position overlaying the screen.

10. The biopsy instrument of claim 9, wherein the cover is slidably attached to one of the catcher body or the catcher handle.

11. The biopsy instrument of claim 9, Wherein the cover is rotatably attached to one of the catcher body or the catcher handle.

12. The biopsy instrument of claim 9, wherein the catcher body with the cover in a closed position overlaying the screen fits a pathology or histology processing cartridge.

13. The biopsy instrument of claim 9, wherein the catcher handle, the catcher body, the cover and a cover hinge are integrally molded.

14. The biopsy instrument of claim 13, wherein deformation of the material of the cover hinge preferably permits the cover to rotate from an open position to a closed position.

15. The biopsy instrument of claim 1, wherein the sample collector includes a screen including a plurality of perforations.

16. The biopsy instrument of claim 1, wherein the catcher handle includes a securing end configured for insertion into the access opening and complements the access opening to provide a seal therewith.

17. The biopsy instrument of claim 16, wherein at least one flexible ring encircles the securing end for providing a seal with the access opening.

18. The biopsy instrument of claim 1, wherein a portion of the catcher body complements the access opening to provide a seal therewith.

19. The biopsy instrument of claim 1, wherein the sample collector includes a flow opening on an upstream side and a screen on a downstream side.

20. The biopsy instrument of claim 9, wherein the cover is removably attached to one of the catcher body or the catcher handle.

21. The biopsy instrument of claim 9, wherein the cover includes a screen.

22. The biopsy instrument of claim 1, wherein the catcher body is removably attached to the catcher handle via a break-away tab.

* * * * *